(12) United States Patent
Zhang et al.

(10) Patent No.: US 11,629,130 B2
(45) Date of Patent: Apr. 18, 2023

(54) LYMPHOID-SPECIFIC TYROSINE PHOSPHATASE (LYP) INHIBITORS

(71) Applicant: Purdue Research Foundation, West Lafayette, IN (US)

(72) Inventors: Zhong-Yin Zhang, West Lafayette, IN (US); Jianping Lin, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 76 days.

(21) Appl. No.: 17/168,212

(22) Filed: Feb. 5, 2021

(65) Prior Publication Data

US 2021/0323926 A1 Oct. 21, 2021

Related U.S. Application Data

(60) Provisional application No. 63/009,505, filed on Apr. 14, 2020.

(51) Int. Cl.
| | | |
|---|---|---|
| *C07D 215/56* | (2006.01) | |
| *C07D 401/12* | (2006.01) | |
| *C07D 405/12* | (2006.01) | |
| *C07D 409/06* | (2006.01) | |
| *C07D 471/04* | (2006.01) | |
| *A61P 35/00* | (2006.01) | |
| *A61K 31/662* | (2006.01) | |
| *A61K 31/16* | (2006.01) | |
| *A61K 31/165* | (2006.01) | |

(52) U.S. Cl.
CPC ............ *C07D 215/56* (2013.01); *A61P 35/00* (2018.01); *C07D 401/12* (2013.01); *C07D 405/12* (2013.01); *C07D 409/06* (2013.01); *C07D 471/04* (2013.01)

(58) Field of Classification Search
CPC ............... C07D 215/56; C07D 401/12; C07D 405/12; C07D 409/06; C07D 471/04; A61P 35/00; A61K 31/662; A61K 31/16; A61K 31/165
See application file for complete search history.

(56) References Cited

FOREIGN PATENT DOCUMENTS

WO    WO 2021007491     *  1/2021

\* cited by examiner

*Primary Examiner* — Bruck Kifle
(74) *Attorney, Agent, or Firm* — Purdue Research Foundation

(57) ABSTRACT

The present disclosure relates to novel lymphoid-specific tyrosine phosphatase (LYP, encoded by the PTPN22 gene) inhibitors, and to methods of making and using the novel LYP inhibitors. Thus, the compounds according to the disclosure may be used for treating diseases or disorders associated with PTPN22 genetic polymorphism, including type 1 diabetes, rheumatoid arthritis, systemic lupus erythematosis, Graves' disease, Addison's disease, vitiligo, juvenile arthritis, Hashimoto thyroiditis, and other rarer diseases. Furthermore, these LYP inhibitors may be served for a novel class of cancer immunotherapy. The compounds can be injected or orally administered.

10 Claims, 4 Drawing Sheets

| PTP | IC$_{50}$ (µM) | PTP | IC$_{50}$ (µM) |
|---|---|---|---|
| LYP | 1.4 ± 0.2 | PTPε | > 50 |
| PTP1B | > 25 | LAR | > 50 |
| SHP2 | 10.6 ± 0.6 | CD45 | > 25 |
| TC-PTP | > 25 | VHR | 13.9 ± 3.2 |
| PTP-Meg2 | > 50 | VHX | > 25 |
| PTP-PEST | 15.2 ± 2.0 | CDC14 | > 25 |
| PTPD1 | > 50 | Laforin | > 50 |
| PTPα | > 25 | LMWPTP | 11.6 ± 5.2 |
| PTPγ | > 50 | | |

LYMPHOID-SPECIFIC TYROSINE PHOSPHATASE (LYP) INHIBITORS

CROSS-REFERENCE TO RELATED APPLICATION

This patent application claims the priority of benefit of U.S. Provisional Patent Application No. 63/009,505, which was filed, Apr. 14, 2020, and which is hereby incorporated by reference in its entirety.

GOVERNMENT RIGHTS

This invention was made with government support under Award No, RO1 CA207288 awarded by the National Institutes of Health (NIH). The government has certain rights in the invention.

TECHNICAL FIELD

The present disclosure relates to novel lymphoid-specific tyrosine phosphatase (LYP) inhibitors, and to methods of making and using the novel lymphoid-specific tyrosine phosphatase (LYP) inhibitors.

BACKGROUND

This section introduces aspects that may help facilitate a better understanding of the disclosure. Accordingly, these statements are to be read in this light and are not to be understood as admissions about what is or is not prior art.

The lymphoid-specific tyrosine phosphatase (LYP) is a non-receptor protein tyrosine phosphatase (PTP), encoded by the PTPN22 gene. It is a 110-kDa protein consisting of a N-terminal PTP domain and a noncatalytic C-terminal segment with several Pro-rich motifs. Human genetics studies have shown that a single-nucleotide polymorphism in PTPN22 is often mutated in patients suffering from autoimmune diseases such as type 1 diabetes, rheumatoid arthritis, systemic lupus erythematosus, Graves' disease, Addison's disease, vitiligo, juvenile arthritis, Hashimoto thyroiditis. Biochemical studies suggest that LYP inhibits T cell activation, likely through dephosphorylation of the T cell receptor (TCR)-associated Lck and ZAP-70 kinases. Because of its critical role in the regulation of TCR signaling pathways, LYP recently emerged as a potential target for therapy of a broad spectrum of autoimmune diseases.

LYP is also found to be a key negative regulator of anti-tumor T cell responses. Adoptive cell therapy studies demonstrated that CD8+ T cells lacking PTPN22 are superior in clearing established tumors. The major impact of PTPN22-deficiency is to endow both effector and memory phenotype CD8+ T cells with an enhanced capacity to produce inflammatory cytokines and kill tumors expressing low affinity tumor-associated antigens. Furthermore, lack of PTPN22 promotes polarization of macrophages toward inflammatory M1 phenotype increases CD40 expression in dendritic cells (leading to higher proliferation of co-cultured CD4+ T cells). This evidence provides a strong rationale for targeting LYP in T cells for cancer immunotherapy.

Thus, given the strong linkage of LYP to autoimmunity, small-molecule LYP inhibitors may have therapeutic value for treating diseases or disorders associated with PTPN22 genetic polymorphism. In addition, successful development of small molecule inhibitors of LYP would also provide a novel class of cancer immunotherapies and encourage development of new combination strategies with LYP inhibitors.

However, the design and synthesis of inhibitors for LYP with optimal potency, selectivity, and pharmacological properties remain a challenging endeavor.

SUMMARY

The present disclosure relates to novel lymphoid-specific tyrosine phosphatase (LYP) inhibitors, and to methods of making and using the novel lymphoid-specific tyrosine phosphatase (LYP) inhibitors.

In one embodiment, the present disclosure provides a compound of formula I:

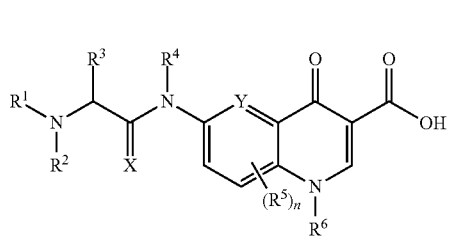

or a stereoisomer, tautomer, solvate, derivative, pharmaceutically acceptable salt thereof, wherein:

$R^1$ and $R^2$ independently represents hydrogen, optionally substituted alkyl, optionally substituted cycloalkyl, optionally substituted cycloalkylalkyl, alkylcarbonyl provided that said alkylcarbonyl is not methylcarbonyl, optionally substituted cycloalkylcarbonyl, optionally substituted cycloalkylalkylcarbonyl, optionally substituted aryl, optionally substituted aralkyl, optionally substituted arylcarbonyl, optionally substituted aralkylcarbonyl, optionally substituted alkoxyalkyl, optionally substituted hydroxyalkyl, optionally substituted heterocyclyl, optionally substituted heterocyclylalkyl, optionally substituted heterocyclycarbonyl, optionally substituted heterocyclyalkylcarbonyl, optionally substituted carbocyclyl, optionally substituted carbocyclylalkyl, optionally substituted amino, optionally substituted alkyl-$SO_2$—, optionally substituted aryl-$SO_2$—, optionally substituted heterocyclyl-$SO_2$—, optionally substituted amino-$SO_2$—, or $R^1$ and $R^2$ together with the N atom to which they are attached form a 5-10 membered heterocyclic ring which optionally comprise a second heteroatom selected from nitrogen or oxygen and, wherein the heterocyclic ring is optionally substituted;

$R^3$ is H, optionally substituted alkyl, optionally substituted alkenyl, optionally substituted alkynyl, optionally substituted cycloalkyl, optionally substituted aryl, optionally substituted heteroaryl, or optionally substituted heterocyclyl;

$R^4$ and $R^6$ independently represents hydrogen, optionally substituted alkyl, optionally substituted cycloalkyl, optionally substituted heterocycloalkyl, optionally substituted aryl and heteroaryl; optionally substituted aralkyl, or optionally substituted heteroaralkyl;

$(R^5)_n$, when n is 1 or 2, represents 1 to 2 —H, —F, —Cl, —Br, —I, —$CFH_2$, —$CF_2H$, —$CF_3$, —CN, —OH, —$NO_2$, —$NH_2$, —$SO_2CH_3$, $SO_2NH_2$, —$SO_2NHCH_3$, optionally substituted —$CO_2$-alkyl, optionally substituted NH(alkyl) or N(alkyl)$_2$, optionally substituted alkyl, optionally substituted alkenyl, optionally substituted alkoxy, optionally substituted S-alkyl, optionally substituted cycloalkyl, optionally substituted heterocycle, optionally substituted aryl or optionally substituted heteroaryl;

X is O or H, wherein —C=X— is —CH$_2$— when X is H, and wherein at least one of R$^1$ and R$^2$ is optionally substituted arylcarbonyl when X is H, and one of R$^1$ and R$^2$ can join R$^3$ to form a ring; and Y is C—R$^5$ or N.

DETAILED DESCRIPTION

Figure 1:
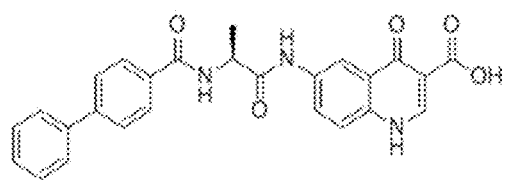
FIG. 1 illustrates data for the selectivity of Example 1 for LYP, and its inhibitory activity toward a panel of 16 mammalian PTPs. Selectivity profiling revealed that Example 1 exhibits over 7-10 folds selectivity for LYP over similar phosphatases.
Figure 2:
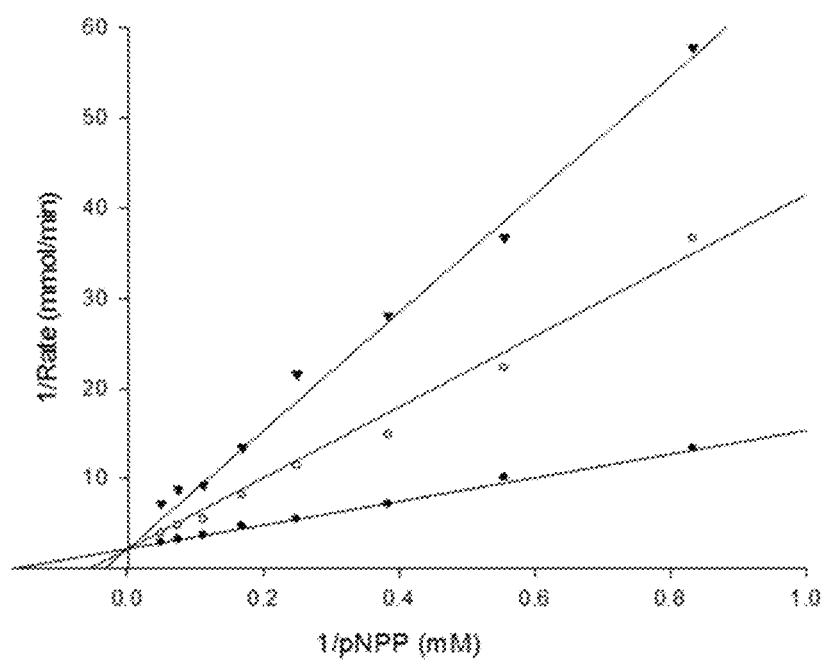
FIG. 2 illustrates kinetic analysis demonstrated Example 1 as a competitive inhibition for LYP with Ki=0.50±0.03 µM.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched-chain C$_1$-C$_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of C$_3$-C$_5$ cycloalkyl are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and particularly cyclopentyl.

The term "alkoxyl", alone or in combination, signifies a group of the Formula alkyl-O— in which the term "alkyl" has the previously given significance, such as methoxy, ethoxy, n-propoxy, isopropoxy, n-butoxy, isobutoxy, sec-butoxy and tert-butoxy, 2-hydroxyethoxy, 2-methoxyethoxy, preferably methoxy and ethoxy, and most preferred methoxy.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons (C$_6$-C$_{14}$) or from 6 to 10 carbon atoms (C$_6$-C$_{10}$) in the ring portions of the groups. Aryl groups can be unsubstituted or substituted, as defined herein. The term "aryl", alone or in combination, further signifies a phenyl or naphthyl group, preferably a phenyl group which optionally carries one or more, particularly one to three substituents each independently selected from halogen, trifluoromethyl, amino, alkyl, alkoxy, aryloxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxyl, nitrol and the like. Preferred substituents of aryl, preferably phenyl are independently selected from halogen, trifluoromethyl, alkyl, alkoxy, cyano and nitro. Examples of aryl are phenyl, cyanophenyl, methoxyphenyl, fluorophenyl and methylphenyl.

The term "aralkyl", alone or in combination, signifies an alkyl or cycloalkyl group as previously defined, which is substituted with one or more, preferably one or two, particularly preferred one aryl group and, wherein the term aryl is defined as before. Examples are benzyl, benzyl substituted with hydroxyl, alkoxy or halogen, preferably fluorine.

The term "heterocyclyl", alone or in combination, signifies a saturated, partially unsaturated or aromatic 4- to 10-membered heterocycle which contains one or more, preferably one or two hetero atoms selected from nitrogen, oxygen and sulfur, wherein oxygen and particularly nitrogen are preferred. If desired, it can be substituted one or more carbon atoms by halogen, alkyl, alkoxy, oxo, alloxyalkyl, hydroxyalkyl etc. and/or on a secondary nitrogen atom (i.e. —NH—) by alkyl, cycloalkyl, arakoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyridinyl, furyl, pyrrolidinyl, piperidinyl, morpholinyl, piperazinyl, 3,4-dihydro-1H-isoquinolinyl, thiophenyl and azepanyl, wherein each of these rings can be optionally substituted by one or more, preferably one substituent independently selected from alkyl and halogen. Particularly preferred are pyrrolidinyl, pyridinyl, furyl, thiophenyl and chloro-pyridinyl.

The term "carbocyclyl", alone or in combination, signifies partially unsaturated 4- to 10-membered carbocyclic ring, wherein optionally one or more carbon atoms are substituted by halogen, alkyl, cycloalkyl, alkoxy, oxo, aryl, with alkyl being preferred. An example of carbocyclyl is indanyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methyl-ethylamino, pyrrolidinyl and piperidino. Particularly preferred primary amino.

The term "cycloalkylalkyl", alone or in combination, signifies an alkyl group which is substituted with one or more, preferably one cycloalkyl group and, wherein the terms alkyl and cycloalkyl have the previously given significance.

The term "cycloalkylalkylcarbonyl", alone or in combination, signifies a cycloalkylalkyl-C(O)— group, wherein cycloalkylalkyl is defined as before.

The term "cycloalkylalkoxy", alone or in combination, signifies an alkoxy group which is substituted with one or more, preferably one cycloalkyl group and, wherein the terms alkoxy and cycloalkyl have the previously given significance.

The term "cycloalkylalkoxyalkyl", alone or in combination, signifies an alkyl group which is substituted with one or more, preferably one cycloalkylalkoxy group and, wherein the terms alkyl and cycloalkylalkoxy have the previously given significance.

The term "heterocyclylalkylcarbonyl", alone or in combination, signifies a heterocyclylalkyl-C(O)— group, wherein heterocyclyalkyl is defined as before.

The term "aralkylcarbonyl", alone or in combination, signifies an aralkyl-C(O)— group, wherein aralkyl is defined as before.

The term "alkylcarbonyl", alone or in combination, signifies an alkyl-C(O)— group, wherein alkyl is defined as before.

The term "cycloalkylcarbonyl", alone or in combination, signifies cycloalkyl-C(O)— group, wherein cycloalkyl is defined as before.

The term "arylcarbonyl", alone or in combination, signifies an aryl-C(O)— group, wherein aryl is defined as before.

The term "alkoxyalkyl", alone or in combination, signifies an alkyl group which is substituted with one or more, preferably one alkoxy group and, wherein the terms alkyl and alkoxy have the previously given significance.

The term "hydroxyalkyl", alone or in combination, signifies an alkyl group which is substituted with one or more, preferably one hydroxy group and, wherein the terms alkyl and hydroxy have the previously given significance.

The term "heterocyclyalkyl", alone or in combination, signifies an alkyl group which is substituted with one or more, preferably one heterocyclyl group and, wherein the terms alkyl and heterocyclyl have the previously given significance.

The term "heterocyclylcarbonyl", alone or in combination, signifies a heterocyclyl-C(O)— group, wherein heterocyclyl is defined as before.

The term "carbocyclyalkyl", alone or in combination, signifies an alkyl group which is substituted with one or more, preferably one carbocyclyl group and, wherein the terms alkyl and carbocyclyl have the previously given significance.

The term "halogen" signifies fluorine, chlorine, bromine or iodine and preferably fluorine, chlorine or bromine and particularly chlorine.

The compounds of formula I can also be solvated, e.g. hydrated. The salvation can be effected in the course of the manufacturing process or can take place e.g. as a consequence of hygroscopic properties of an initially anhydrous compound of (formula I) (hydration). The term pharmaceutically acceptable salts also includes pharmaceutically usable solvates.

In more detail, for example, the —COOH groups of compounds according to formula I can be esterified. The alkyl and aralkyl esters are examples of suitable esters. The methyl, ethyl, propyl, butyl and benzyl esters are preferred esters. The methyl and ethyl ester are especially preferred.

Further examples of pharmaceutically suitable esters are compounds of formula I, wherein the hydroxyl groups can be esterified. Examples of such esters are formate, acetate, propionate, butyrate, isobutyrate, valerate, 2-methylbutyate, isovalerate and N, N-dimethylaminooacetate. Preferred esters are acetate and N, N-dimethylaminoacetate.

A "heteroaryl" represents aromatic ring comprising at least one hetero atom such as N, S, O, or Se. Hetero aryl in the present disclosure may be any hetero aryl. Hetero aryl in the present disclosure may be but is not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, benzimidazolinyl groups, or any combination thereof.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The present invention relates to novel compounds capable of inhibiting the activity of LYP. Thus, the compounds according to the invention may be used for treating diseases or disorders associated with PTPN22 genetic polymorphism, including type 1 diabetes, rheumatoid arthritis, systemic lupus erythematosis, Graves' disease, Addison's disease, vitiligo, juvenile arthritis, Hashimoto thyroiditis, and other rarer diseases. Furthermore, these LYP inhibitors may be served for a novel class of cancer immunotherapy. The compounds can be injected or orally administered.

Experimental Sections

The present invention also includes processes for the preparation of the compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

General synthetic procedures and reagents: Unless otherwise specified, all reagents were purchased from commercial suppliers and used directly without further purification. Analytical thin layer chromatography (TLC) was performed on 0.25 mm silica gel 60-$F_{254}$. Column chromatography was performed using KP-SIL silica gel (Biotage, USA), and flash column chromatography was performed on Biotage pre-packed columns using the automated flash chromatography system Biotage Isolera One. The $^1$H and $^{13}$C NMR spectra were recorded on a Bruker AVANCE 500 MHz instrument. Chemical shifts for Proton magnetic resonance spectra ($^1$H NMR) were quoted in parts per million (ppm) referenced to the appropriate solvent peak or 0.0 ppm for tetramethylsilane (TMS). The following abbreviations were used to describe peak splitting patterns when appropriate: br=broad, s=singlet, d=doublet, t=triplet, q=quartet, m=multiplet, dd=doublet of doublet. Coupling constants, J, were reported in hertz unit (Hz). Chemical shifts for 13C NMR were reported in ppm referenced to the center line at 39.52 of DMSO-d. Low-resolution mass spectra and purity data were obtained using an Agilent Technologies 6470 series, triple quadrupole LC/MS. High-resolution mass spectra (HRMS) were recorded on an Agilent Mass spectrometer using ESI-TOF (electrospray ionization-time of flight).

Compounds of formula I were prepared according to the following general synthetic as illustrated in Scheme 1. When appropriate, protecting groups are used as needed according to established synthetic procedures known to those of skill in the art, and may or may not be removed upon completion of synthesis. Starting materials are synthesized according to methods known in the art or are commercially available.

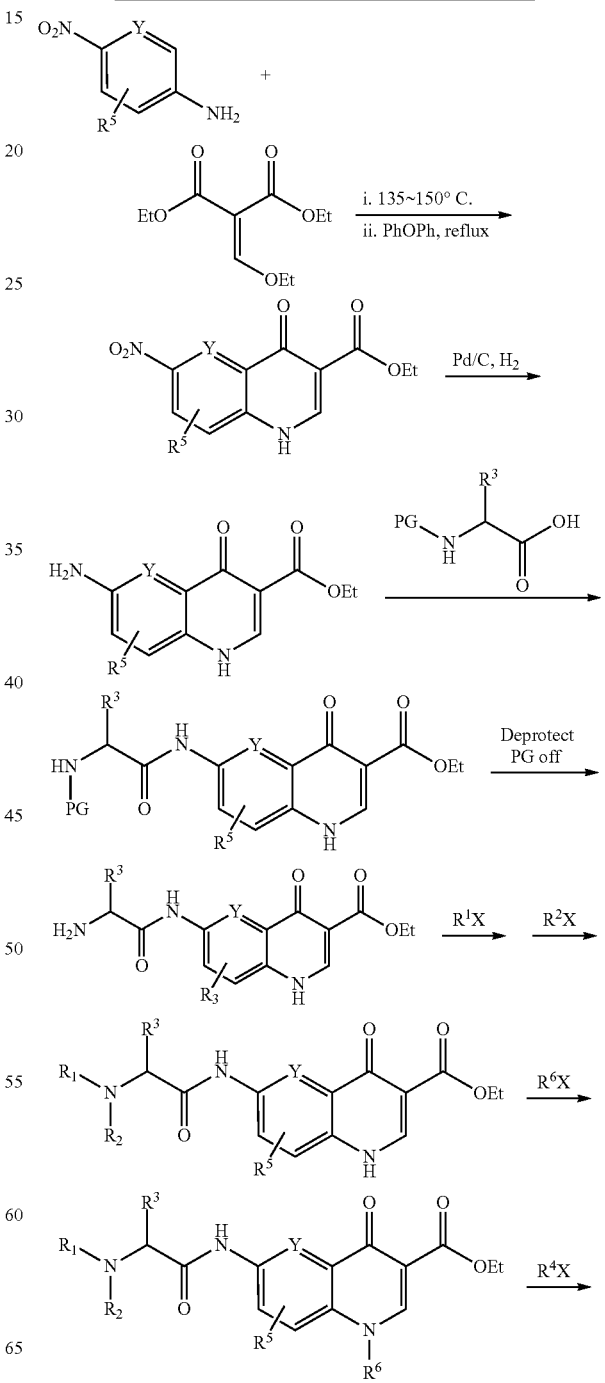

Scheme 1 General synthesis for compound of formula I

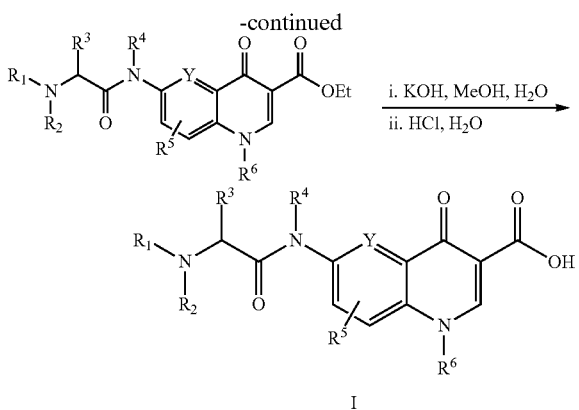

Example 1: (S)-6-(2-([1,1'-biphenyl]-4-ylcarboxamido)propanamido)-4-oxo-1,4-dihydroquinoline-3-carboxylic acid

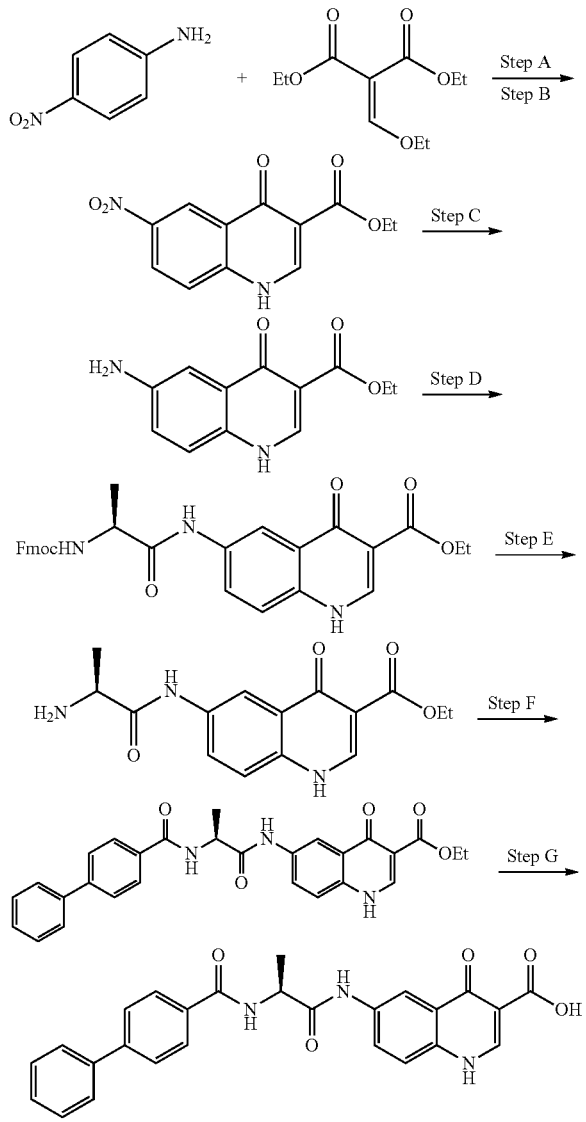

Step A & Step B: Ethyl 6-nitro-4-oxo-1,4-dihydroquinoline-3-carboxylate

Starting from p-nitroaniline and diethyl ethoxymethylenemalonate, advanced intermediate ethyl 6-nitro-4-oxo-1,4-dihydroquinoline-3-carboxylate was obtained following a previously reported protocol. See Al-As'ad, R. M., Elabadelah, M. M., Sabri, S. S., Zahra, J. A. & Voelter, W. Synthesis of 6-Ethyl-1,2,9-trioxopyrrolo[3,2-f]quinoline-8-carboxylic Acid. Z Naturforsch B 68, 700-706, doi:10.5560/Znb.2013-3009 (2013).

Step C: Ethyl 6-amino-4-oxo-1,4-dihydroquinoline-3-carboxylate

To a solution of 6-nitro-4-oxo-1,4-dihydroquinoline-3-carboxylate (2.0 g, 7.63 mmol) in dimethylformamide (DMF, 40 ml), was added 10% Pd/C (0.2 g). Hydrogenation was carried out under a pressure of 1 atm at 100° C. After stirring for 12 hours, removal of the catalyst and solvent gave a solid residue, which was then washed by ethyl acetate (40 ml) to afford ethyl 6-amino-4-oxo-1,4-dihydroquinoline-3-carboxylate (1.5 g, 85% yield). $^1$H NMR (500 MHz, DMSO) δ 12.03 (s, 1H), 8.32 (s, 1H), 7.33 (d, J=8.7 Hz, 1H), 7.26 (d, J=2.6 Hz, 1H), 6.99 (dd, J=8.7, 2.6 Hz, 1H), 5.45 (s, 2H), 4.18 (q, J=7.1 Hz, 2H), 1.26 (t, J=7.1 Hz, 3H). LC-MS (ESI): m/z [M+H]$^+$ calcd. For $C_{12}H_{13}N_2O_3$: 233.09, found: 233.10.

Step D: (S)-Ethyl 6-(2-((((9H-fluoren-9-yl)methoxy)carbonyl)amino) propanamido)-4-oxo-1,4-dihydroquinoline-3-carboxylate Fmoc-L-Ala-OH (2.0 g, 6.42 mmol), HOBt (1.13 g, 8.35 mmol) and HBTU (3.17 g, 8.35 mmol) were dissolved in dry dimethylformamide (DMF, 40 ml). The mixture was stirred at room temperature for 15 min. Ethyl 6-amino-4-oxo-1,4-dihydroquinoline-3-carboxylate (1.34 g, 5.78 mmol) and N,N-Diisopropylethylamine (3.4 ml, 19.27 mmol) were then added and the resulting mixture was stirred at room temperature overnight. DMF was removed by rotary evaporator, Ethyl acetate and water were then added. The formed precipitate was collected by filtration and purified by column chromatography eluting with dichloromethane/methanol 10:1 v/v to give the Fmoc-protected intermediate as a light brown solid (2.2 g, 65% yield). 1H NMR (500 MHz, DMSO) δ 12.28 (d, J=6.4 Hz, 1H), 10.27 (s, 1H), 8.47 (d, J=6.5 Hz, 1H), 8.39 (d, J=2.1 Hz, 1H), 7.95 (dd, J=8.9, 2.3 Hz, 1H), 7.88 (d, J=7.6 Hz, 2H), 7.75-7.68 (m, 3H), 7.57 (d, J=8.9 Hz, 1H), 7.44-7.37 (m, 2H), 7.35-7.28 (m, 2H), 4.28-4.26 (m, 2H), 4.21-4.17 (m, 4H), 1.32 (d, J=7.1 Hz, 3H), 1.26 (t, J=7.1 Hz, 3H). LC-MS (ESI): m/z [M+H]$^+$ calcd. For $C_{30}H_{28}N_3O_6$: 526.20, found: 526.30.

Step E: (S)-Ethyl 6-(2-aminopropanamido)-4-oxo-1,4-dihydroquinoline-3-carboxylate The Fmoc-protected intermediate (S)-ethyl 6-(2-((((9H-fluoren-9-yl)methoxy)carbonyl)amino) propanamido)-4-oxo-1,4-dihydroquinoline-3-carboxylate (2.1 g, 4.0 mmol) was dissolved in DMF (30 ml). Piperidine (7.5 ml) was added and the reaction mixture stirred at room temperature for 1 hour. Concentration in vacuo gave a brown solid which was washed by ethyl acetate to afford the title compound (0.83 g, 69% yield). $^1$H NMR (500 MHz, DMSO) δ 8.49 (s, 1H), 8.43 (d, J=2.4 Hz, 1H), 7.98 (dd, J=8.9, 2.4 Hz, 1H), 7.58 (d, J=8.9 Hz, 1H), 4.21 (q, J=7.1 Hz, 2H), 3.52-3.47 (m, 1H), 1.27 (t, J=7.1 Hz, 3H), 1.25 (d, J=6.9 Hz, 3H). LC-MS (ESI): m/z [M+H]$^+$ calcd. For $C_{15}H_{18}N_3O_4$: 304.13, found: 304.20.

Step F: (S)-Ethyl 6-(2-([1,1'-biphenyl]-4-ylcarboxamido) propanamido)-4-oxo-1,4-dihydroquinoline-3-carboxylate Biphenyl-4-carboxylic acid (0.40 g, 2.02 mmol), HOBt (0.35 g, 2.62 mmol) and HBTU (1.0 g, 2.62 mmol) were dissolved in dry dimethylformamide (DMF, 20 ml). The mixture was stirred at room temperature for 15 min. (S)-ethyl 6-(2-aminopropanamido)-4-oxo-1,4-dihydroquinoline-3-carboxylate (0.55 g, 1.82 mmol) and N,N-Diisopropylethylamine (1.07 ml, 6.05 mmol) were then added and the resulting mixture was stirred at room temperature over night. DMF was removed by rotary evaporator, Ethyl acetate and water were then added. The formed precipitate was collected by filtration and washed by ethyl acetate to give (S)-ethyl 6-(2-([1,1'-biphenyl]-4-ylcarboxamido)propanamido)-4-oxo-1,4-dihydroquinoline-3-carboxylate (0.76 g, 78% yield). $^1$H NMR (500 MHz, DMSO) δ 12.30 (d, J=6.7 Hz, 1H), 10.36 (s, 1H), 8.74 (d, J=7.0 Hz, 1H), 8.48 (d, J=6.7 Hz, 1H), 8.41 (d, J=2.3 Hz, 1H), 8.03 (d, J=8.4 Hz, 2H), 8.00 (dd, J=8.9, 2.4 Hz, 1H), 7.79 (d, J=8.4 Hz, 2H), 7.75 (d, J=7.2 Hz, 2H), 7.59 (d, J=8.9 Hz, 1H), 7.50 (t, J=7.6 Hz, 2H), 7.41 (t, J=7.4 Hz, 1H), 4.67-4.61 (m, 1H), 4.21 (q, J=7.1 Hz, 2H), 1.48 (d, J=7.2 Hz, 3H), 1.28 (t, J=7.1 Hz, 3H). LC-MS (ESI): m/z [M+H]$^+$ calcd. For $C_{28}H_{26}N_3O_5$: 484.19, found: 484.20.

Step G: (S)-6-(2-([1,1'-Biphenyl]-4-ylcarboxamido)propanamido)-4-oxo-1,4-dihydroquinoline-3-carboxylic acid (Example 1)

To a solution of compound (S)-ethyl 6-(2-([1,1'-biphenyl]-4-ylcarboxamido)propanamido)-4-oxo-1,4-dihydroquinoline-3-carboxylate (500 mg, 1.03 mmol) in Methanol (20 ml) and H$_2$O (20 ml), KOH (580 mg, 10.34 mmol) was added. The obtained mixture was stirred at 60° C. for 16 hours. The mixture was brought to 0° C., carefully acidified with 1N HCl until pH=1. The formed precipitate was collected by filtration and purified by HPLC to furnish the desired product as an off-white solid (422 mg, 90% yield). $^1$H NMR (500 MHz, DMSO) δ 10.53 (s, 1H), 8.83 (d, J=6.8 Hz, 1H), 8.78 (d, J=6.8 Hz, 1H), 8.65 (d, J=2.4 Hz, 1H), 8.10 (dd, J=9.1, 2.4 Hz, 1H), 8.04 (d, J=8.5 Hz, 2H), 7.84-7.77 (m, 3H), 7.76-7.70 (m, 2H), 7.50 (t, J=7.6 Hz, 2H), 7.45-7.39 (m, 1H), 4.68-4.61 (m, 1H), 1.49 (d, J=7.2 Hz, 3H). $^{13}$C NMR (126 MHz, DMSO) δ 177.99 (s), 172.03 (s), 166.55 (s), 166.08 (s), 144.05 (s), 142.89 (s), 139.15 (s), 137.34 (s), 135.40 (s), 132.67 (s), 129.04 (s), 128.30 (s), 128.08 (s), 126.88 (s), 126.41 (s), 126.19 (s), 124.95 (s), 120.41 (s), 113.21 (s), 107.07 (s), 50.13 (s), 17.61 (s). LC-MS (ESI): m/z [M–H]$^-$ calcd. For $C_{26}H_{20}N_3O_5$: 454.14, found: 454.30. HRMS (ESI-TOF): m/z [M–H]$^-$ calcd. For $C_{26}H_{20}N_3O_5$: 454.1403, found: 454.1413; Purity: >95% (UV, λ=254 nm).

Examples 2 to 51 were prepared according to the procedure described above for Example 1. All Examples 1-51 are listed in Table 1.

TABLE 1

Examples 1-51

| Example No. | Structure | Analytical Data | IC$_{50}$ (μm) |
|---|---|---|---|
| 1 | 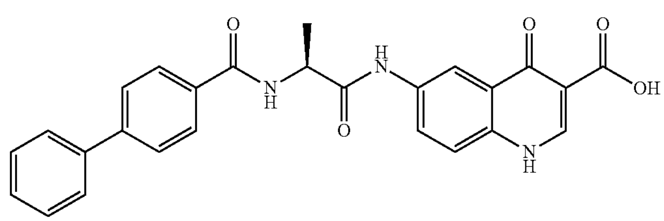 [SMILES: C[C@H](NC(=O)c1ccc(-c2ccccc2)cc1)C(=O)Nc1ccc2[nH]cc(C(=O)O)c(=O)c2c1] | MS: 454 (M – H)$^-$ | 1.4 |
| 2 | 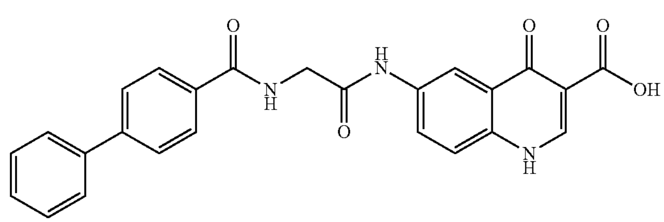 [SMILES: O=C(CNC(=O)c1ccc(-c2ccccc2)cc1)Nc1ccc2[nH]cc(C(=O)O)c(=O)c2c1] | MS: 440 (M – H)$^-$ | 8.7 |
| 3 | 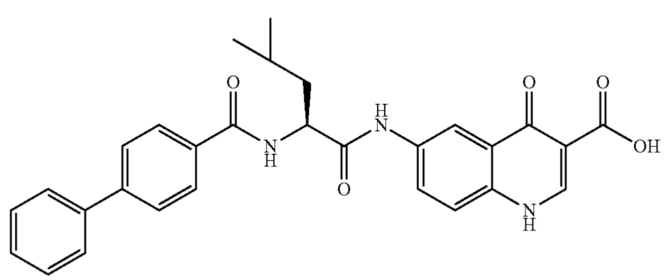 [SMILES: CC(C)C[C@H](NC(=O)c1ccc(-c2ccccc2)cc1)C(=O)Nc1ccc2[nH]cc(C(=O)O)c(=O)c2c1] | MS: 496 (M – H)$^-$ | 9.6 |

TABLE 1-continued

Examples 1-51

| Example No. | Structure | Analytical Data | IC$_{50}$ (μm) |
|---|---|---|---|
| 4 | 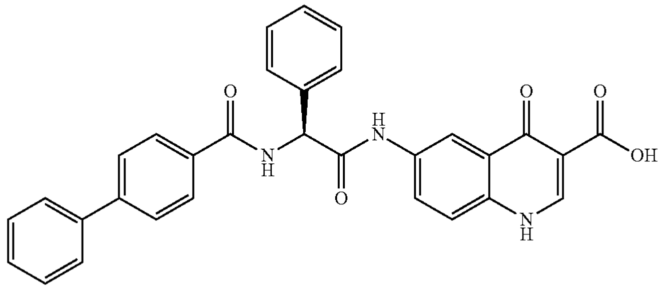 [SMILES: O=C(N[C@H](C(=O)Nc1ccc2[nH]cc(C(=O)O)c(=O)c2c1)c1ccccc1)c1ccc(-c2ccccc2)cc1] | MS: 516 (M − H)⁻ | 4.3 |
| 5 | 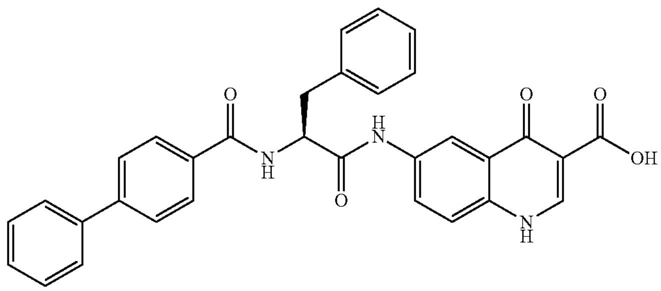 [SMILES: O=C(N[C@@H](Cc1ccccc1)C(=O)Nc1ccc2[nH]cc(C(=O)O)c(=O)c2c1)c1ccc(-c2ccccc2)cc1] | MS: 530 (M − H)⁻ | n.d. |
| 6 | 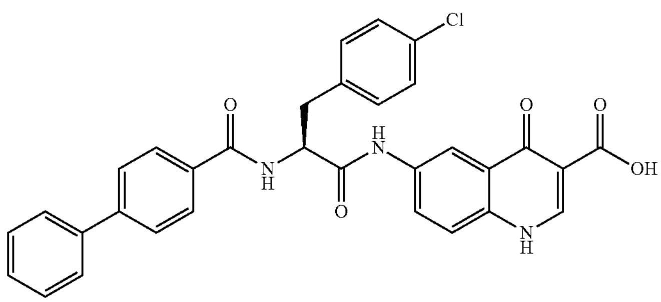 [SMILES: O=C(N[C@@H](Cc1ccc(Cl)cc1)C(=O)Nc1ccc2[nH]cc(C(=O)O)c(=O)c2c1)c1ccc(-c2ccccc2)cc1] | MS: 564 (M − H)⁻ | 4.3 |
| 7 | 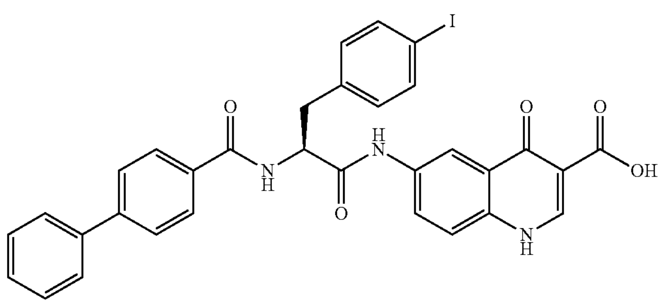 [SMILES: O=C(N[C@@H](Cc1ccc(I)cc1)C(=O)Nc1ccc2[nH]cc(C(=O)O)c(=O)c2c1)c1ccc(-c2ccccc2)cc1] | MS: 656 (M − H)⁻ | 1.5 |
| 8 | 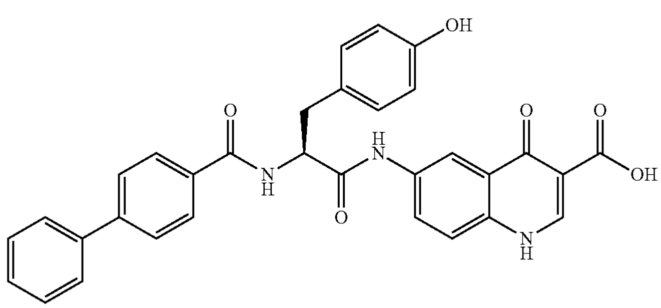 [SMILES: O=C(N[C@@H](Cc1ccc(O)cc1)C(=O)Nc1ccc2[nH]cc(C(=O)O)c(=O)c2c1)c1ccc(-c2ccccc2)cc1] | MS: 546 (M − H)⁻ | n.d. |

TABLE 1-continued

Examples 1-51

| Example No. | Structure | Analytical Data | IC$_{50}$ (μm) |
|---|---|---|---|
| 9 | 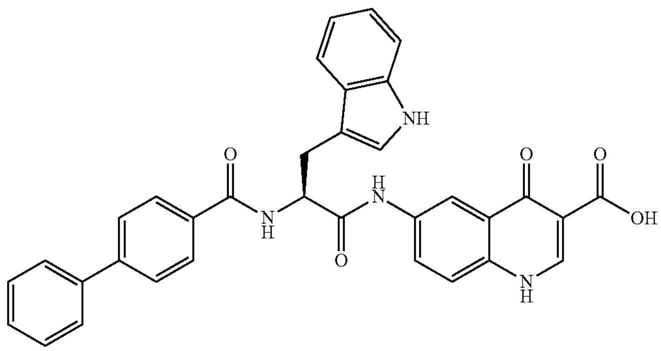 [SMILES: O=C(N[C@@H](Cc1c[nH]c2ccccc12)C(=O)Nc1ccc2[nH]cc(C(=O)O)c(=O)c2c1)c1ccc(-c2ccccc2)cc1] | MS: 569 (M − H)$^-$ | 9.5 |
| 10 | 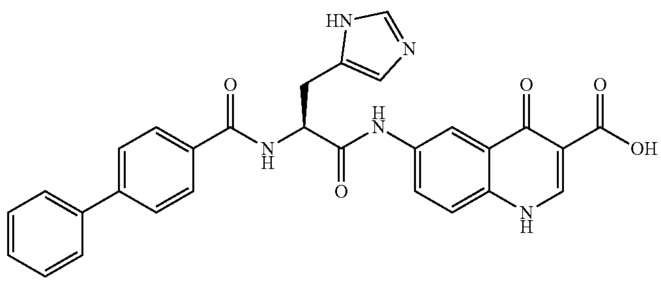 [SMILES: O=C(N[C@@H](Cc1cnc[nH]1)C(=O)Nc1ccc2[nH]cc(C(=O)O)c(=O)c2c1)c1ccc(-c2ccccc2)cc1] | MS: 520 (M − H)$^-$ | n.d. |
| 11 | 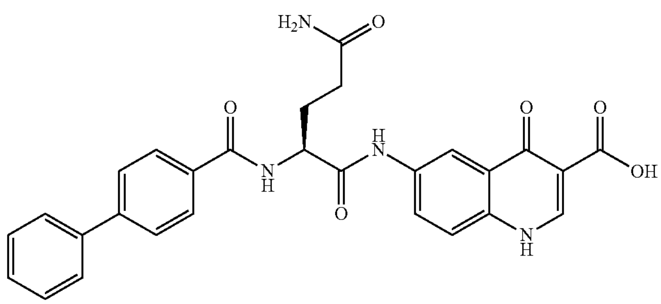 [SMILES: NC(=O)CC[C@H](NC(=O)c1ccc(-c2ccccc2)cc1)C(=O)Nc1ccc2[nH]cc(C(=O)O)c(=O)c2c1] | MS: 511 (M − H)$^-$ | n.d. |
| 12 | 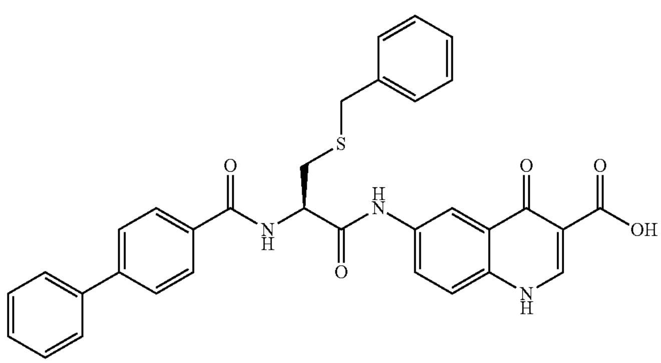 [SMILES: O=C(N[C@@H](CSCc1ccccc1)C(=O)Nc1ccc2[nH]cc(C(=O)O)c(=O)c2c1)c1ccc(-c2ccccc2)cc1] | MS: 576 (M − H)$^-$ | 4.3 |
| 13 | 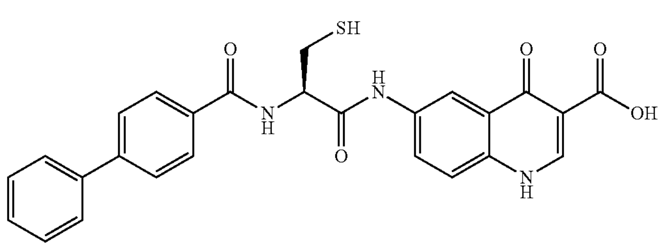 [SMILES: O=C(N[C@@H](CS)C(=O)Nc1ccc2[nH]cc(C(=O)O)c(=O)c2c1)c1ccc(-c2ccccc2)cc1] | MS: 486 (M − H)$^-$ | n.d. |

TABLE 1-continued

Examples 1-51

| Example No. | Structure | Analytical Data | IC$_{50}$ (μm) |
|---|---|---|---|
| 14 | 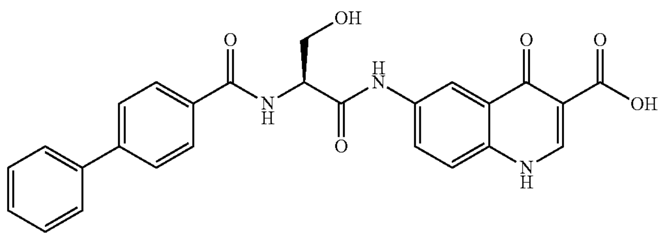 [SMILES: O=C(N[C@@H](CO)C(=O)Nc1ccc2[nH]cc(C(=O)O)c(=O)c2c1)c1ccc(-c2ccccc2)cc1] | MS: 470 (M − H)⁻ | n.d. |
| 15 | 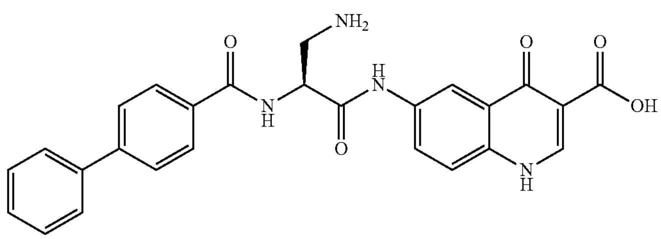 [SMILES: NC[C@H](NC(=O)c1ccc(-c2ccccc2)cc1)C(=O)Nc1ccc2[nH]cc(C(=O)O)c(=O)c2c1] | MS: 469 (M − H)⁻ | 9.2 |
| 16 | 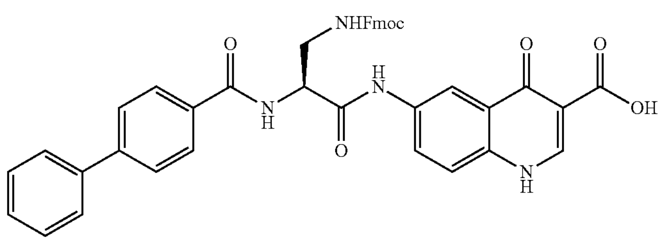 | MS: 691 (M − H)⁻ | 2.8 |
| 17 | 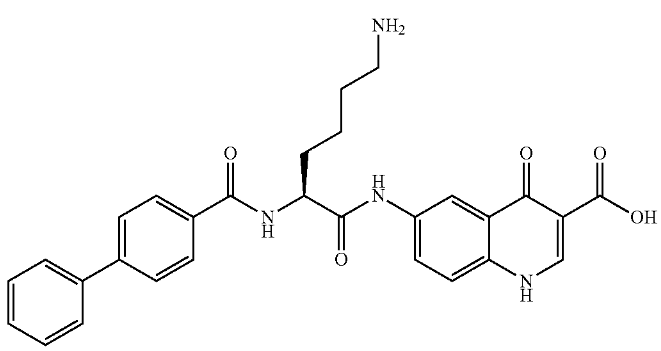 [SMILES: NCCCC[C@H](NC(=O)c1ccc(-c2ccccc2)cc1)C(=O)Nc1ccc2[nH]cc(C(=O)O)c(=O)c2c1] | MS: 511 (M − H)⁻ | >50 |
| 18 | 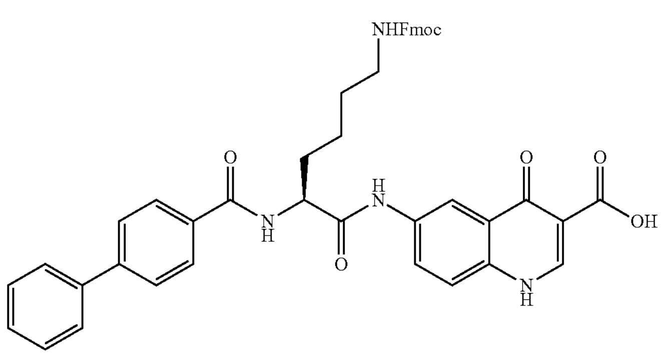 | MS: 733 (M − H)⁻ | >50 |

TABLE 1-continued

Examples 1-51

| Example No. | Structure | Analytical Data | IC$_{50}$ (μm) |
|---|---|---|---|
| 19 | 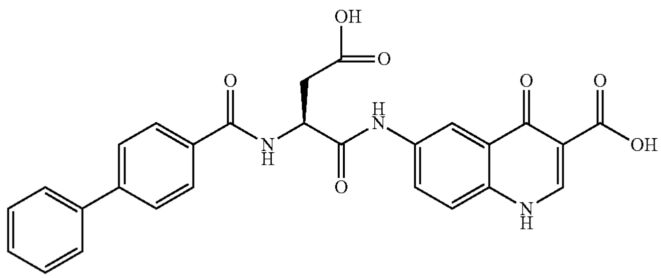 [SMILES: O=C(O)C[C@H](NC(=O)c1ccc(-c2ccccc2)cc1)C(=O)Nc1ccc2[nH]cc(C(=O)O)c(=O)c2c1] | MS: 498 (M − H)⁻ | >50 |
| 20 | 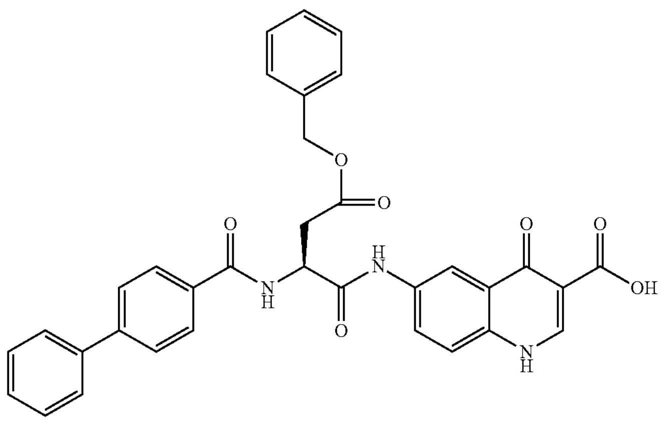 [SMILES: O=C(C[C@H](NC(=O)c1ccc(-c2ccccc2)cc1)C(=O)Nc1ccc2[nH]cc(C(=O)O)c(=O)c2c1)OCc1ccccc1] | MS: 588 (M − H)⁻ | 6.0 |
| 21 | 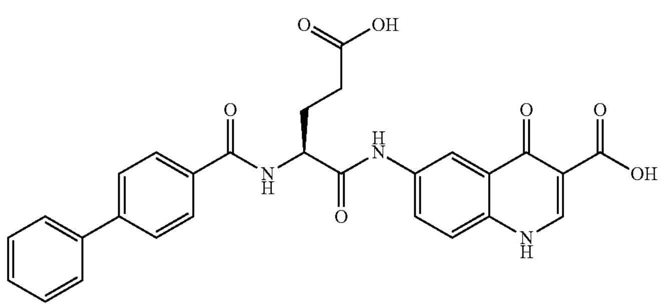 [SMILES: O=C(O)CC[C@H](NC(=O)c1ccc(-c2ccccc2)cc1)C(=O)Nc1ccc2[nH]cc(C(=O)O)c(=O)c2c1] | MS: 512 (M − H)⁻ | >50 |
| 22 | 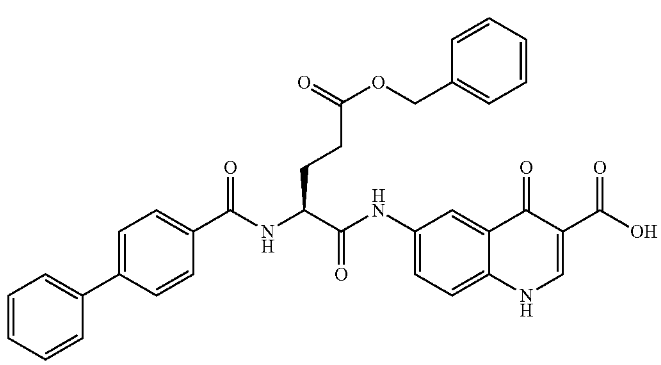 [SMILES: O=C(CC[C@H](NC(=O)c1ccc(-c2ccccc2)cc1)C(=O)Nc1ccc2[nH]cc(C(=O)O)c(=O)c2c1)OCc1ccccc1] | MS: 602 (M − H)⁻ | 20.7 |

TABLE 1-continued

Examples 1-51

| Example No. | Structure | Analytical Data | IC$_{50}$ (μM) |
|---|---|---|---|
| 23 | 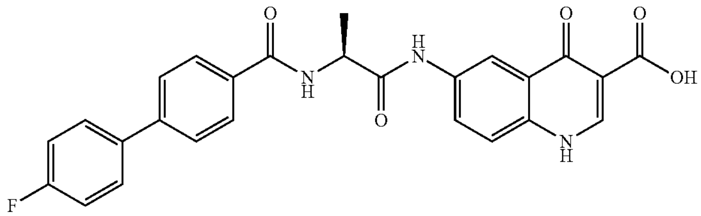 [SMILES: C[C@H](NC(=O)c1ccc(-c2ccc(F)cc2)cc1)C(=O)Nc1ccc2[nH]cc(C(=O)O)c(=O)c2c1] | MS: 472 (M − H)⁻ | 1.5 |
| 24 | 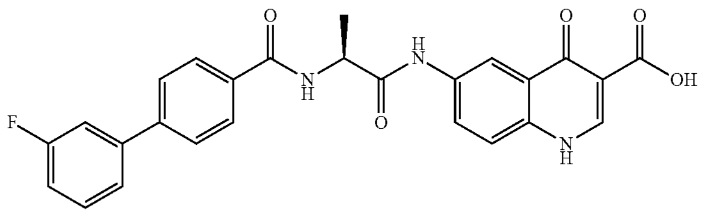 [SMILES: C[C@H](NC(=O)c1ccc(-c2cccc(F)c2)cc1)C(=O)Nc1ccc2[nH]cc(C(=O)O)c(=O)c2c1] | MS: 472 (M − H)⁻ | 2.1 |
| 25 | 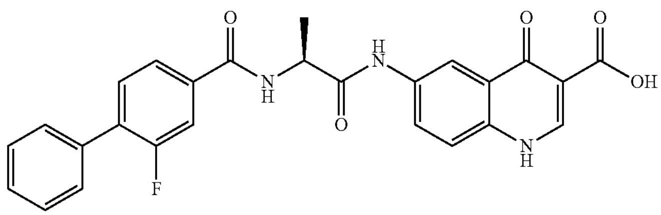 [SMILES: C[C@H](NC(=O)c1ccc(-c2ccccc2)c(F)c1)C(=O)Nc1ccc2[nH]cc(C(=O)O)c(=O)c2c1] | MS: 472 (M − H)⁻ | 0.43 |
| 26 | 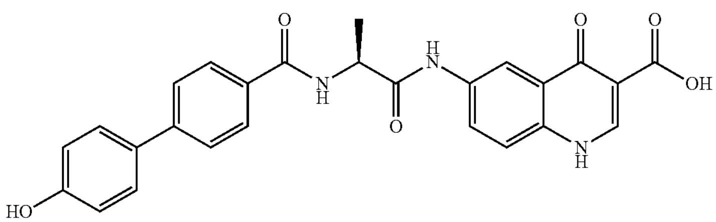 [SMILES: C[C@H](NC(=O)c1ccc(-c2ccc(O)cc2)cc1)C(=O)Nc1ccc2[nH]cc(C(=O)O)c(=O)c2c1] | MS: 470 (M − H)⁻ | 1.4 |
| 27 | 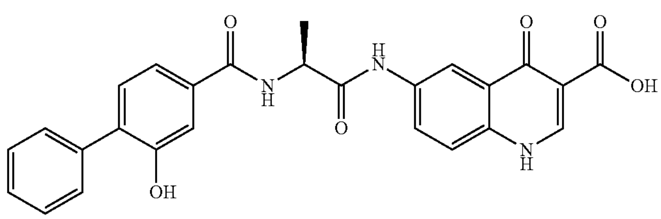 [SMILES: C[C@H](NC(=O)c1ccc(-c2ccccc2)c(O)c1)C(=O)Nc1ccc2[nH]cc(C(=O)O)c(=O)c2c1] | MS: 470 (M − H)⁻ | n.d. |
| 28 | 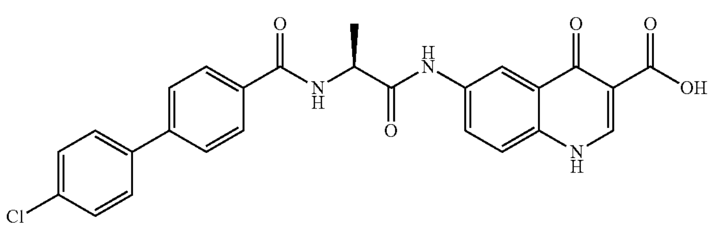 [SMILES: C[C@H](NC(=O)c1ccc(-c2ccc(Cl)cc2)cc1)C(=O)Nc1ccc2[nH]cc(C(=O)O)c(=O)c2c1] | MS: 488 (M − H)⁻ | 3.7 |
| 29 | 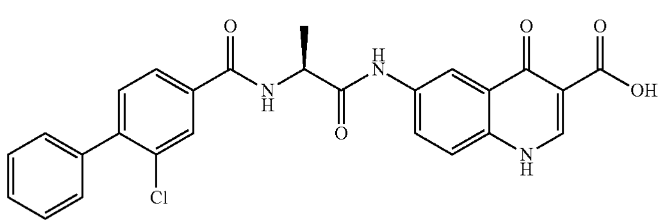 [SMILES: C[C@H](NC(=O)c1ccc(-c2ccccc2)c(Cl)c1)C(=O)Nc1ccc2[nH]cc(C(=O)O)c(=O)c2c1] | MS: 488 (M − H)⁻ | n.d. |

TABLE 1-continued

Examples 1-51

| Example No. | Structure | Analytical Data | IC$_{50}$ (μm) |
|---|---|---|---|
| 30 | 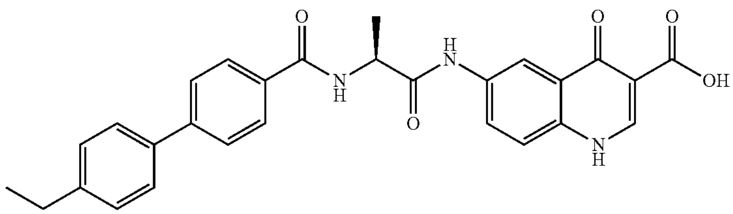 [SMILES: CCc1ccc(-c2ccc(C(=O)N[C@@H](C)C(=O)Nc3ccc4[nH]cc(C(=O)O)c(=O)c4c3)cc2)cc1] | MS: 482 (M − H)$^-$ | 0.54 |
| 31 | 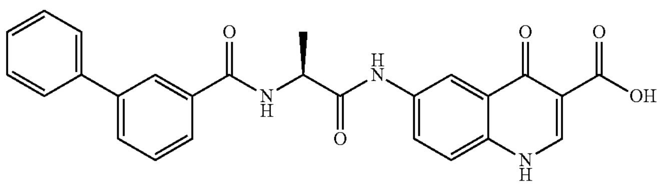 [SMILES: C[C@H](NC(=O)c1cccc(-c2ccccc2)c1)C(=O)Nc1ccc2[nH]cc(C(=O)O)c(=O)c2c1] | MS: 454 (M − H)$^-$ | 11.0 |
| 32 | 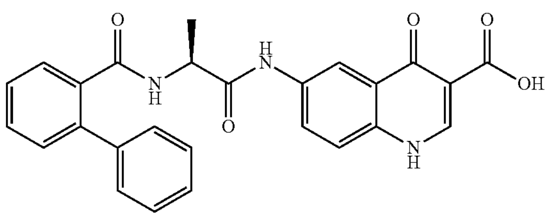 [SMILES: C[C@H](NC(=O)c1ccccc1-c1ccccc1)C(=O)Nc1ccc2[nH]cc(C(=O)O)c(=O)c2c1] | MS: 454 (M − H)$^-$ | 16.4 |
| 33 | 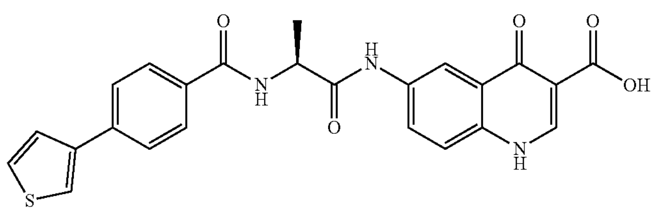 [SMILES: C[C@H](NC(=O)c1ccc(-c2ccsc2)cc1)C(=O)Nc1ccc2[nH]cc(C(=O)O)c(=O)c2c1] | MS: 460 (M − H)$^-$ | 2.9 |
| 34 | 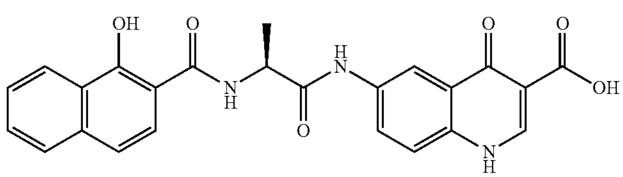 [SMILES: C[C@H](NC(=O)c1ccc2ccccc2c1O)C(=O)Nc1ccc2[nH]cc(C(=O)O)c(=O)c2c1] | MS: 444 (M − H)$^-$ | 31.9 |
| 35 | 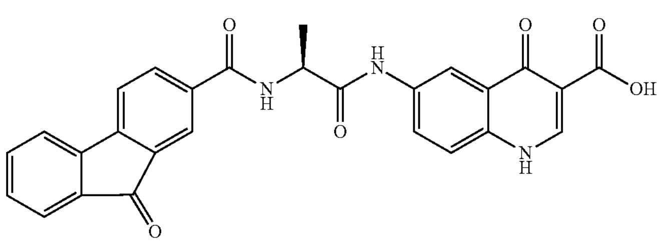 [SMILES: C[C@H](NC(=O)c1ccc2c(c1)C(=O)c1ccccc1-2)C(=O)Nc1ccc2[nH]cc(C(=O)O)c(=O)c2c1] | MS: 480 (M − H)$^-$ | 0.47 |
| 36 | 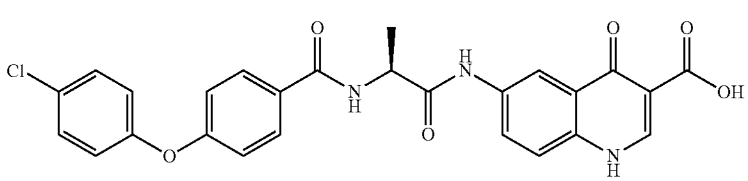 [SMILES: C[C@H](NC(=O)c1ccc(Oc2ccc(Cl)cc2)cc1)C(=O)Nc1ccc2[nH]cc(C(=O)O)c(=O)c2c1] | MS: 504 (M − H)$^-$ | 1.6 |

TABLE 1-continued

Examples 1-51

| Example No. | Structure | Analytical Data | IC$_{50}$ (μm) |
|---|---|---|---|
| 37 | 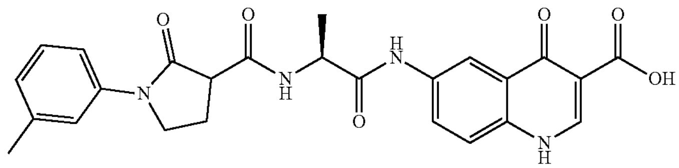 [SMILES: Cc1cccc(N2CCC(C(=O)N[C@@H](C)C(=O)Nc3ccc4[nH]cc(C(=O)O)c(=O)c4c3)C2=O)c1] | MS: 475 (M − H)⁻ | n.d. |
| 38 | 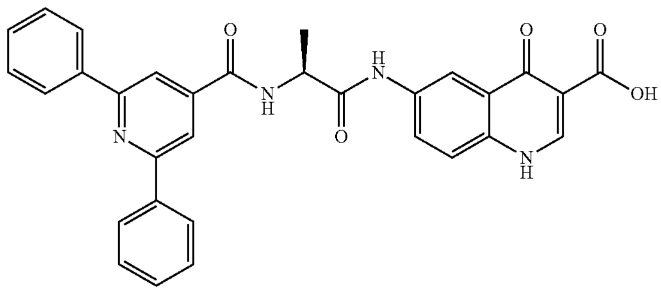 [SMILES: C[C@H](NC(=O)c1cc(-c2ccccc2)nc(-c2ccccc2)c1)C(=O)Nc1ccc2[nH]cc(C(=O)O)c(=O)c2c1] | MS: 531 (M − H)⁻ | >20 |
| 39 | 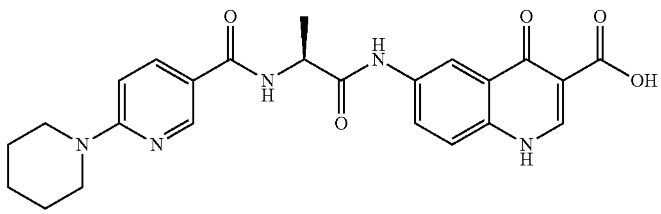 | MS: 562 (M − H)⁻ | >20 |
| 40 | 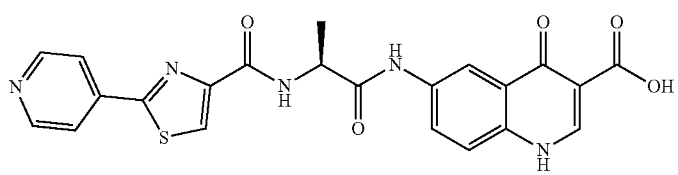 [SMILES: C[C@H](NC(=O)c1csc(-c2ccncc2)n1)C(=O)Nc1ccc2[nH]cc(C(=O)O)c(=O)c2c1] | MS: 462 (M − H)⁻ | n.d. |
| 41 | 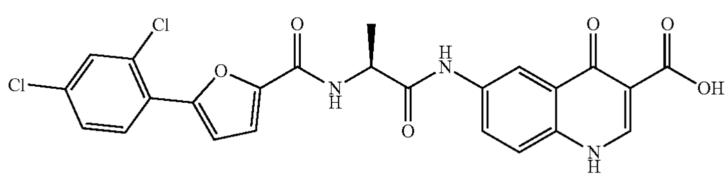 [SMILES: C[C@H](NC(=O)c1ccc(-c2ccc(Cl)cc2Cl)o1)C(=O)Nc1ccc2[nH]cc(C(=O)O)c(=O)c2c1] | MS: 512 (M − H)⁻ | 1.2 |
| 42 | 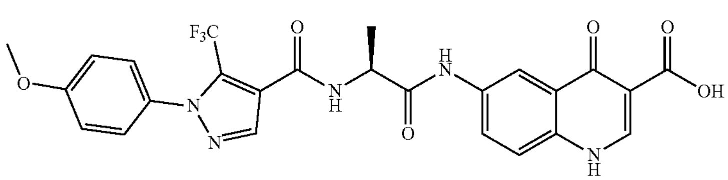 [SMILES: COc1ccc(-n2ncc(C(=O)N[C@@H](C)C(=O)Nc3ccc4[nH]cc(C(=O)O)c(=O)c4c3)c2C(F)(F)F)cc1] | MS: 542 (M − H)⁻ | n.d. |
| 43 | 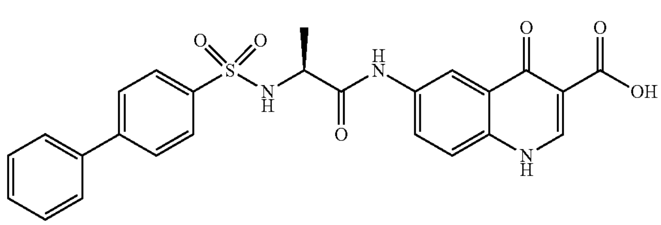 [SMILES: C[C@H](NS(=O)(=O)c1ccc(-c2ccccc2)cc1)C(=O)Nc1ccc2[nH]cc(C(=O)O)c(=O)c2c1] | MS: 490 (M − H)⁻ | 8.9 |

TABLE 1-continued

Examples 1-51

| Example No. | Structure | Analytical Data | IC$_{50}$ (μm) |
|---|---|---|---|
| 44 | 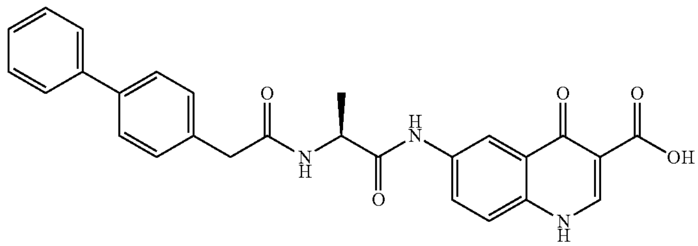 [SMILES: C[C@H](NC(=O)Cc1ccc(-c2ccccc2)cc1)C(=O)Nc1ccc2[nH]cc(C(=O)O)c(=O)c2c1] | MS: 468 (M − H)$^-$ | 2.2 |
| 45 | 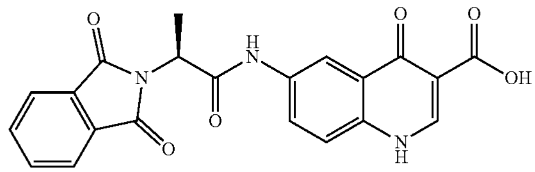 [SMILES: C[C@@H](C(=O)Nc1ccc2[nH]cc(C(=O)O)c(=O)c2c1)N1C(=O)c2ccccc2C1=O] | MS: 404 (M − H)$^-$ | 12.6 |
| 46 | 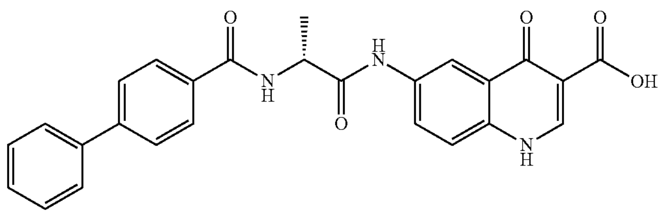 [SMILES: C[C@@H](NC(=O)c1ccc(-c2ccccc2)cc1)C(=O)Nc1ccc2[nH]cc(C(=O)O)c(=O)c2c1] | MS: 454 (M − H)$^-$ | 1.1 |
| 47 | 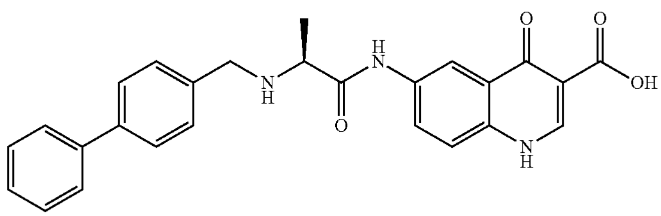 [SMILES: C[C@H](NCc1ccc(-c2ccccc2)cc1)C(=O)Nc1ccc2[nH]cc(C(=O)O)c(=O)c2c1] | MS: 440 (M − H)$^-$ | n.d. |
| 48 | 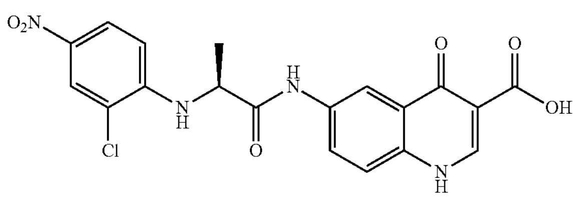 | MS: 368 (M − H)$^-$ | n.d. |
| 49 | 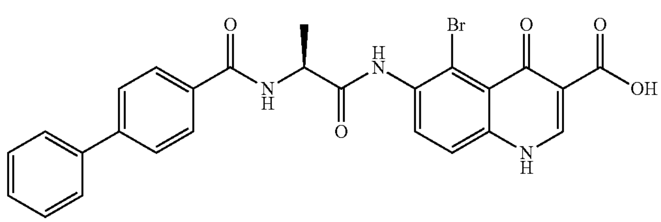 [SMILES: C[C@H](NC(=O)c1ccc(-c2ccccc2)cc1)C(=O)Nc1ccc2[nH]cc(C(=O)O)c(=O)c2c1Br] | MS: 532 (M − H)$^-$ | n.d. |
| 50 | 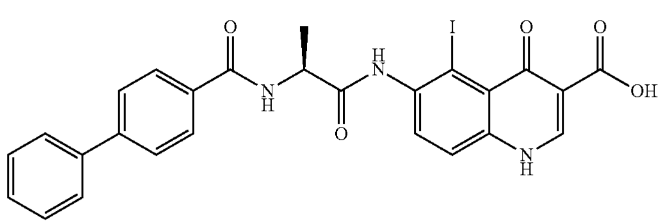 [SMILES: C[C@H](NC(=O)c1ccc(-c2ccccc2)cc1)C(=O)Nc1ccc2[nH]cc(C(=O)O)c(=O)c2c1I] | MS: 580 (M − H)$^-$ | n.d. |

TABLE 1-continued

Examples 1-51

| Example No. | Structure | Analytical Data | IC$_{50}$ (μm) |
|---|---|---|---|
| 51 | 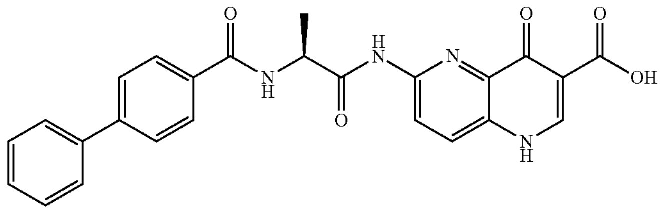 [SMILES: C[C@H](NC(=O)c1ccc(-c2ccccc2)cc1)C(=O)Nc1ccc2[nH]cc(C(=O)O)c(=O)c2n1] | MS: 455 (M − H)⁻ | n.d. |

Example 52: (S)-6-(2-([1,1'-biphenyl]-4-ylcarboxamido)propanamido)-1-(3,4-dichlorobenzyl)-4-oxo-1,4-dihydroquinoline-3-carboxylic acid

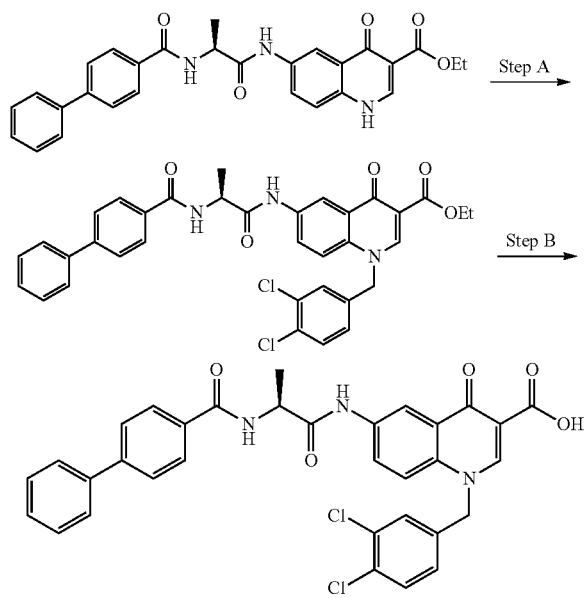

Scheme 2. Synthetic method for Example 52

Step A: (S)-ethyl 6-(2-([1,1'-biphenyl]-4-ylcarboxamido)propanamido)-1-(3,4-dichlorobenzyl)-4-oxo-1,4-dihydroquinoline-3-carboxylate To a solution of compound (S)-ethyl 6-(2-([1,1'-biphenyl]-4-ylcarboxamido) propanamido)-4-oxo-1,4-dihydroquinoline-3-carboxylate (200 mg, 0.41 mmol) in DMF (20 ml), K$_2$CO$_3$ (172 mg, 1.24 mmol) and 4-(bromomethyl)-1,2-dichlorobenzene (110 mg, 0.45 mmol) were added. And the solution was kept at 80° C. for 2 h. After cooling to room temperature, the surplus of K$_2$CO$_3$ was then filtered and the solvent evaporated. The oily residue was purified by column to furnish the desired product as an off-white solid (232 mg, 87% yield). LC-MS (ESI): m/z [M+H]⁺ calcd. For C$_{35}$H$_{30}$C$_{12}$N$_3$O$_5$: 642.16, found: 642.10.

Step B: (S)-6-(2-([1,1'-biphenyl]-4-ylcarboxamido)propanamido)-1-(3,4-dichlorobenzyl)-4-oxo-1,4-dihydroquinoline-3-carboxylic acid To a solution of compound (S)-ethyl 6-(2-([1,1'-biphenyl]-4-ylcarboxamido) propanamido)-1-(3,4-dichlorobenzyl)-4-oxo-1,4-dihydroquinoline-3-carboxylate (100 mg, 0.15 mmol) in Methanol (4 ml) and H$_2$O (4 ml), KOH (87 mg, 1.56 mmol) was added. The obtained mixture was stirred at 60° C. for 16 hours. The mixture was brought to 0° C., carefully acidified with 1N HCl until pH=1. The formed precipitate was collected by filtration and purified by HPLC to furnish the desired product as an off-white solid (81 mg, 84% yield). LC-MS (ESI): m/z [M−H]⁻ calcd. For C$_{33}$H$_{24}$C$_{12}$N$_3$O$_5$: 612.11, found: 612.20. HRMS (ESI-TOF): m/z [M−H]⁻ calcd. For C$_{26}$H$_{20}$N$_3$O$_5$: 612.1093, found: 612.1101; Purity: >95% (UV, λ=254 nm).

Examples 53 to 74 were prepared according to the procedure described above for Example 52. All Examples 52-74 are listed in Table 2.

TABLE 2

Examples 52-74

| Example No. | Structure | Analytical Data | IC$_{50}$ (μm) |
|---|---|---|---|
| 52 | 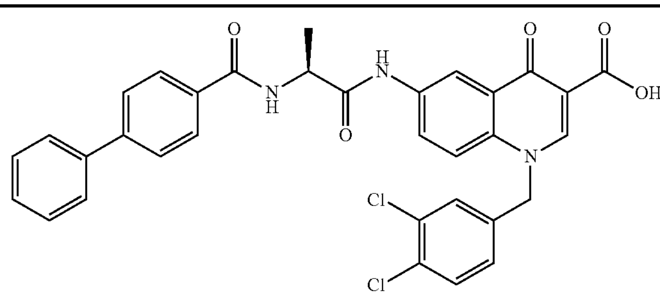 | MS: 612 (M − H)⁻ | n.d. |

TABLE 2-continued

Examples 52-74

| Example No. | Structure | Analytical Data | IC$_{50}$ (μm) |
|---|---|---|---|
| 53 | 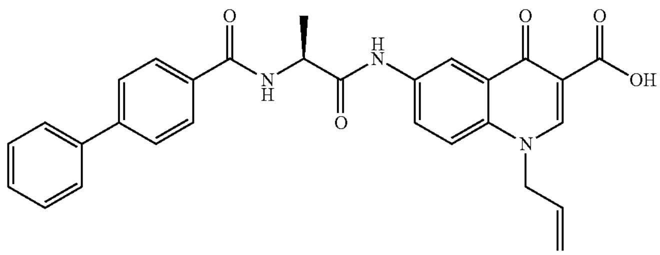 [SMILES: C=CCn1cc(C(=O)O)c(=O)c2cc(NC(=O)[C@H](C)NC(=O)c3ccc(-c4ccccc4)cc3)ccc21] | MS: 494 (M − H)⁻ | n.d. |
| 54 | 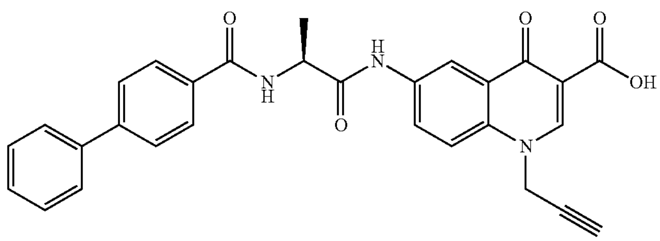 [SMILES: C#CCn1cc(C(=O)O)c(=O)c2cc(NC(=O)[C@H](C)NC(=O)c3ccc(-c4ccccc4)cc3)ccc21] | MS: 492 (M − H)⁻ | n.d. |
| 55 | 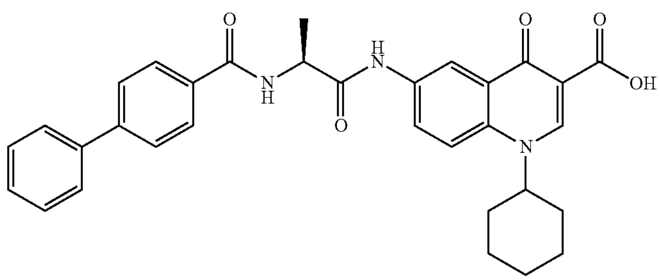 [SMILES: C[C@H](NC(=O)c1ccc(-c2ccccc2)cc1)C(=O)Nc1ccc2c(c1)c(=O)c(C(=O)O)cn2C1CCCCC1] | MS: 536 (M − H)⁻ | n.d. |
| 56 | 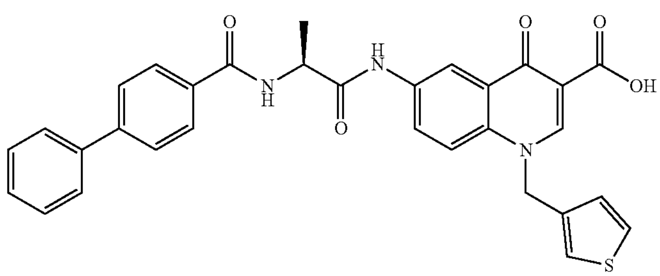 [SMILES: C[C@H](NC(=O)c1ccc(-c2ccccc2)cc1)C(=O)Nc1ccc2c(c1)c(=O)c(C(=O)O)cn2Cc1ccsc1] | MS: 550 (M − H)⁻ | n.d. |
| 57 | 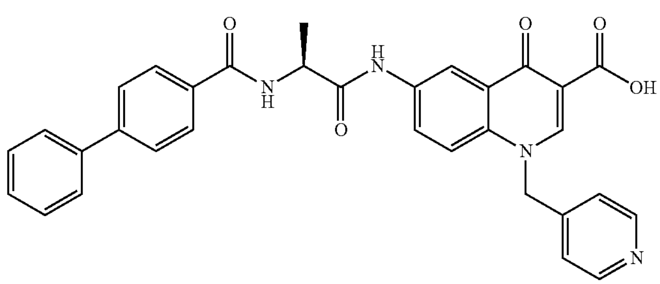 [SMILES: C[C@H](NC(=O)c1ccc(-c2ccccc2)cc1)C(=O)Nc1ccc2c(c1)c(=O)c(C(=O)O)cn2Cc1ccncc1] | MS: 545 (M − H)⁻ | n.d. |

TABLE 2-continued

Examples 52-74

| Example No. | Structure | Analytical Data | IC$_{50}$ (μm) |
|---|---|---|---|
| 58 | 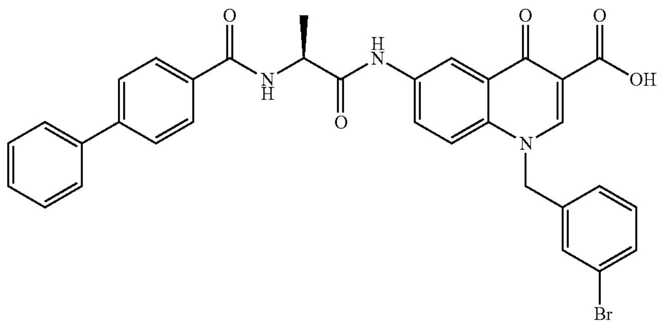 [SMILES: C[C@H](NC(=O)c1ccc(-c2ccccc2)cc1)C(=O)Nc1ccc2c(c1)c(=O)c(C(=O)O)cn2Cc1cccc(Br)c1] | MS: 622 (M − H)⁻ | n.d. |
| 59 | 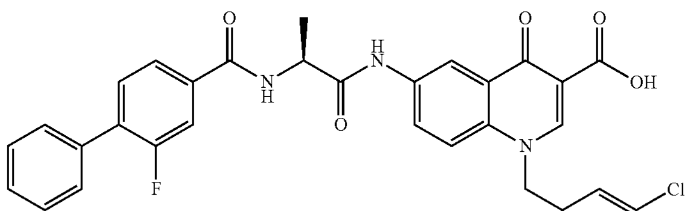 | MS: 630 (M − H)⁻ | n.d. |
| 60 | 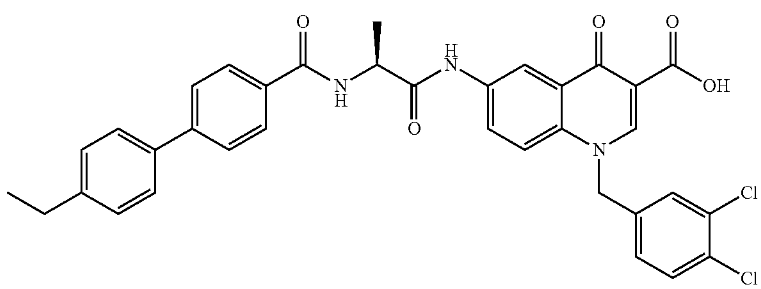 [SMILES: CCc1ccc(-c2ccc(C(=O)N[C@@H](C)C(=O)Nc3ccc4c(c3)c(=O)c(C(=O)O)cn4Cc3ccc(Cl)c(Cl)c3)cc2)cc1] | MS: 640 (M − H)⁻ | n.d. |
| 61 | 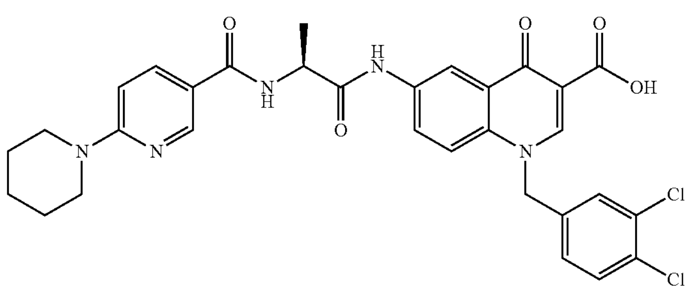 [SMILES: C[C@H](NC(=O)c1ccc(N2CCCCC2)nc1)C(=O)Nc1ccc2c(c1)c(=O)c(C(=O)O)cn2Cc1ccc(Cl)c(Cl)c1] | MS: 620 (M − H)⁻ | n.d. |
| 62 | 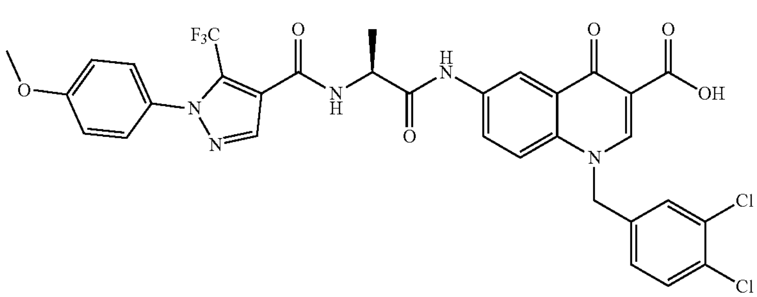 [SMILES: COc1ccc(-n2ncc(C(=O)N[C@@H](C)C(=O)Nc3ccc4c(c3)c(=O)c(C(=O)O)cn4Cc3ccc(Cl)c(Cl)c3)c2C(F)(F)F)cc1] | MS: 700 (M − H)⁻ | n.d. |

TABLE 2-continued

Examples 52-74

| Example No. | Structure | Analytical Data | IC$_{50}$ (μm) |
|---|---|---|---|
| 63 | 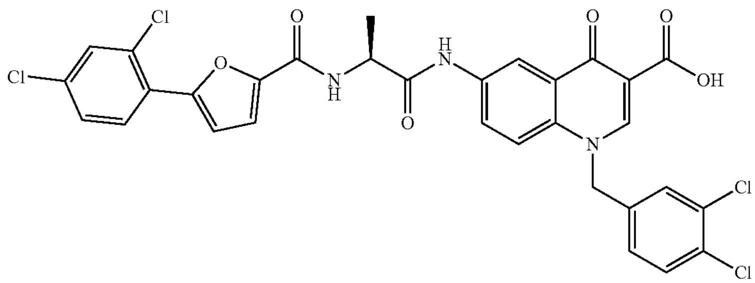 [SMILES: C[C@H](NC(=O)c1ccc(-c2ccc(Cl)cc2Cl)o1)C(=O)Nc1ccc2c(c1)c(=O)c(C(=O)O)cn2Cc1ccc(Cl)c(Cl)c1] | MS: 672 (M − H)$^-$ | n.d. |
| 64 | 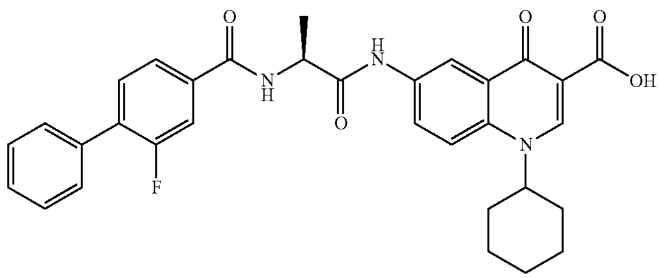 [SMILES: C[C@H](NC(=O)c1ccc(-c2ccccc2)c(F)c1)C(=O)Nc1ccc2c(c1)c(=O)c(C(=O)O)cn2C1CCCCC1] | MS: 554 (M − H)$^-$ | n.d. |
| 65 | 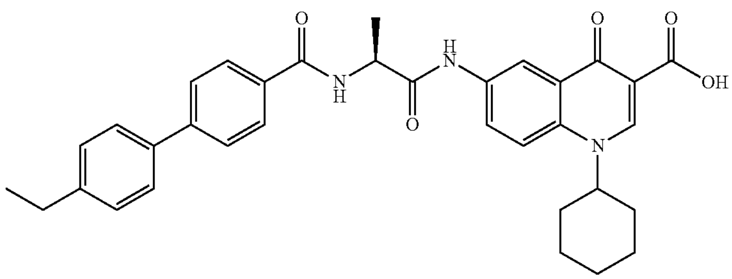 [SMILES: CCc1ccc(-c2ccc(C(=O)N[C@@H](C)C(=O)Nc3ccc4c(c3)c(=O)c(C(=O)O)cn4C3CCCCC3)cc2)cc1] | MS: 564 (M − H)$^-$ | n.d. |
| 66 | 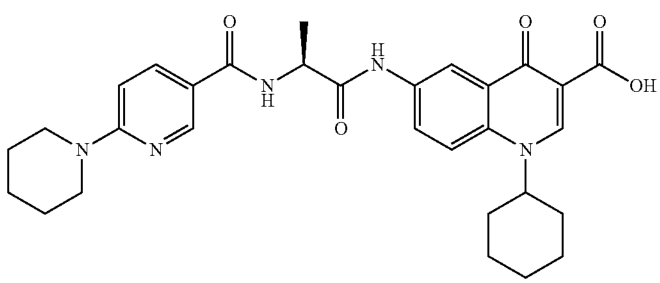 [SMILES: C[C@H](NC(=O)c1ccc(N2CCCCC2)nc1)C(=O)Nc1ccc2c(c1)c(=O)c(C(=O)O)cn2C1CCCCC1] | MS: 544 (M − H)$^-$ | n.d. |
| 67 | 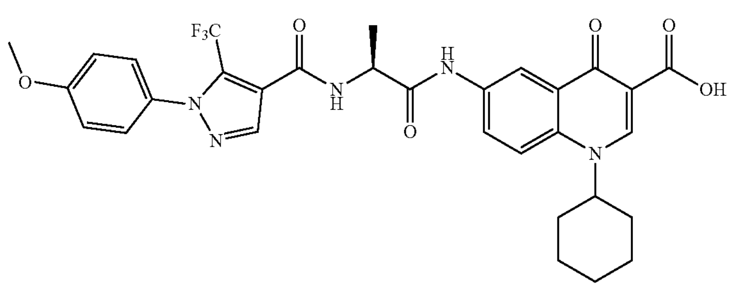 [SMILES: COc1ccc(-n2ncc(C(=O)N[C@@H](C)C(=O)Nc3ccc4c(c3)c(=O)c(C(=O)O)cn4C3CCCCC3)c2C(F)(F)F)cc1] | MS: 624 (M − H)$^-$ | n.d. |

TABLE 2-continued

Examples 52-74

| Example No. | Structure | Analytical Data | IC$_{50}$ (μm) |
|---|---|---|---|
| 68 | 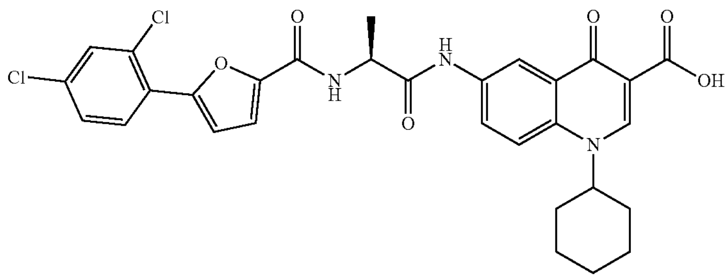 [SMILES: C[C@H](NC(=O)c1ccc(-c2ccc(Cl)cc2Cl)o1)C(=O)Nc1ccc2c(c1)c(=O)c(C(=O)O)cn2C1CCCCC1] | MS: 594 (M − H)⁻ | n.d. |
| 69 | 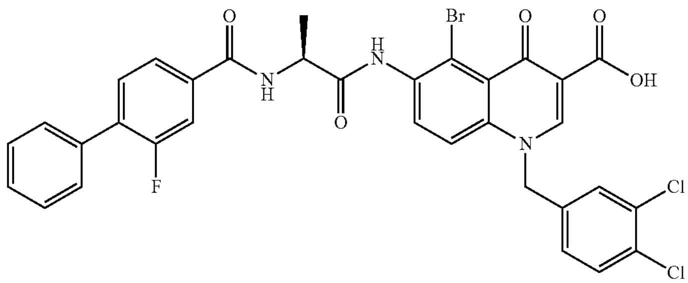 [SMILES: C[C@H](NC(=O)c1ccc(-c2ccccc2)c(F)c1)C(=O)Nc1ccc2c(c1Br)c(=O)c(C(=O)O)cn2Cc1ccc(Cl)c(Cl)c1] | MS: 708 (M − H)⁻ | n.d. |
| 70 | 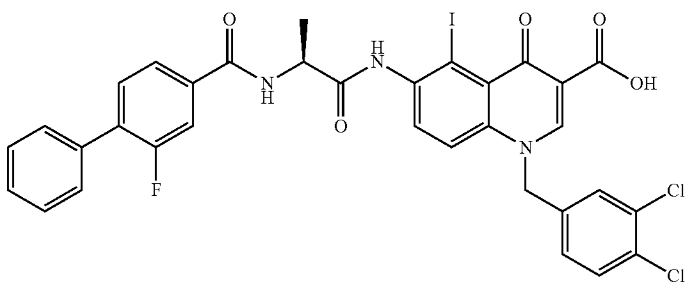 [SMILES: C[C@H](NC(=O)c1ccc(-c2ccccc2)c(F)c1)C(=O)Nc1ccc2c(c1I)c(=O)c(C(=O)O)cn2Cc1ccc(Cl)c(Cl)c1] | MS: 756 (M − H)⁻ | n.d. |
| 71 | 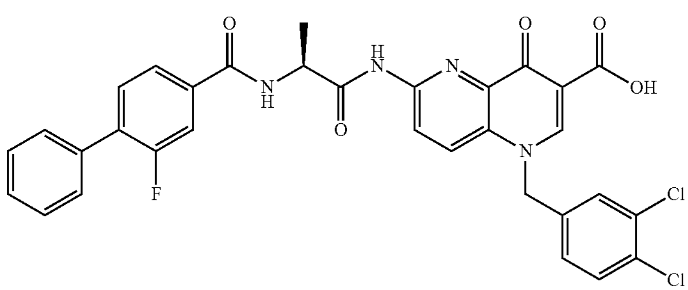 [SMILES: C[C@H](NC(=O)c1ccc(-c2ccccc2)c(F)c1)C(=O)Nc1ccc2c(n1)c(=O)c(C(=O)O)cn2Cc1ccc(Cl)c(Cl)c1] | MS: 631 (M − H)⁻ | n.d. |
| 72 | 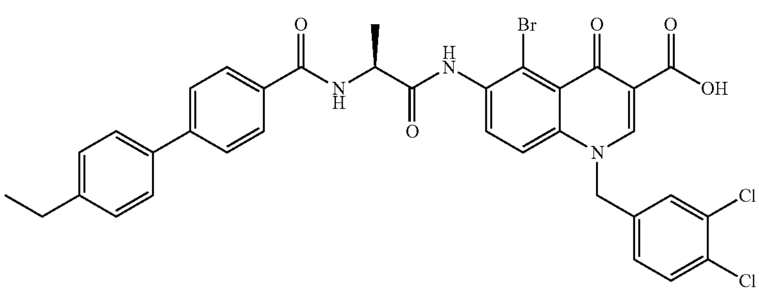 [SMILES: CCc1ccc(-c2ccc(C(=O)N[C@@H](C)C(=O)Nc3ccc4c(c3Br)c(=O)c(C(=O)O)cn4Cc3ccc(Cl)c(Cl)c3)cc2)cc1] | MS: 718 (M − H)⁻ | n.d. |

TABLE 2-continued

Examples 52-74

| Example No. | Structure | Analytical Data | IC$_{50}$ (μm) |
|---|---|---|---|
| 73 | 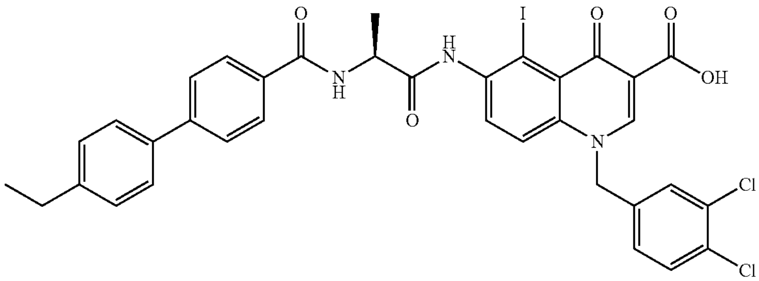 [SMILES: CCc1ccc(-c2ccc(C(=O)N[C@@H](C)C(=O)Nc3ccc4c(c3I)c(=O)c(C(=O)O)cn4Cc3ccc(Cl)c(Cl)c3)cc2)cc1] | MS: 766 (M − H)⁻ | n.d. |
| 74 | 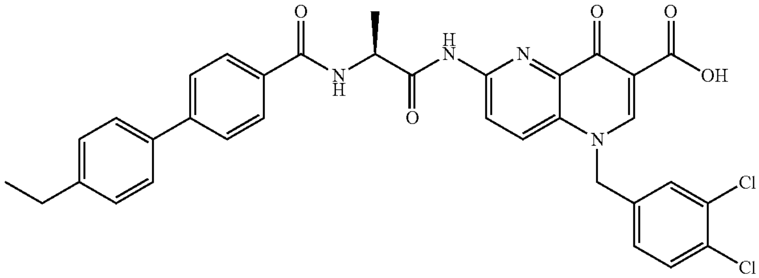 [SMILES: CCc1ccc(-c2ccc(C(=O)N[C@@H](C)C(=O)Nc3ccc4c(n3)c(=O)c(C(=O)O)cn4Cc3ccc(Cl)c(Cl)c3)cc2)cc1] | MS: 641 (M − H)⁻ | n.d. |

Compounds of formula I when X is H were prepared according to the following general synthetic Scheme 3. When appropriate, protecting groups are used as needed according to established synthetic procedures known to those of skill in the art, and may or may not be removed upon completion of synthesis. Starting materials are synthesized according to methods known in the art or are commercially available.

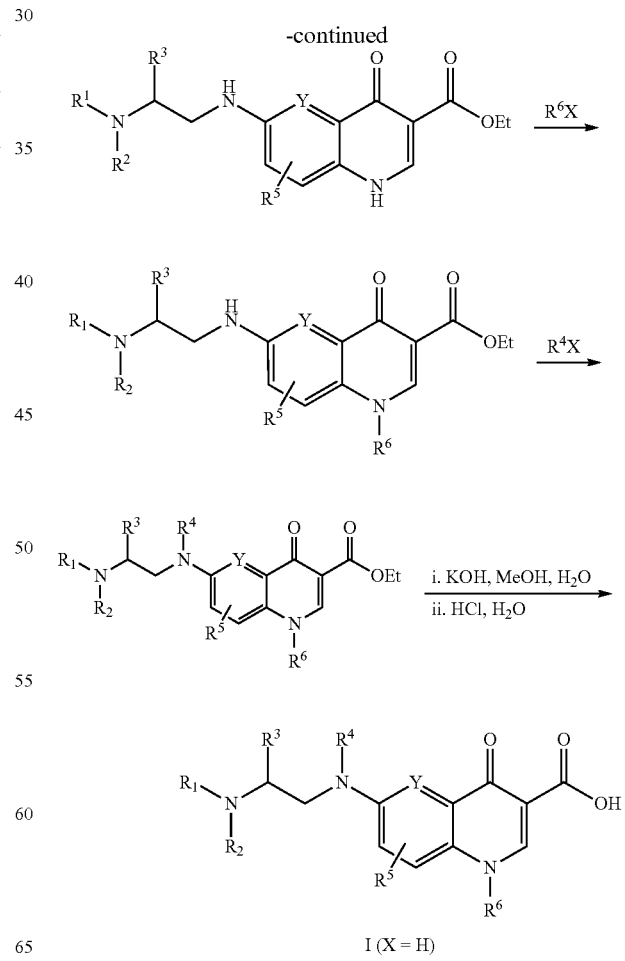

Scheme 3. Synthetic method compounds of formula I when X is H.

Example 75: (S)-6-(2-([1,1'-biphenyl]-4-ylcarboxamido)propanamido)-4-oxo-1,4-dihydroquinoline-3-carboxylic acid

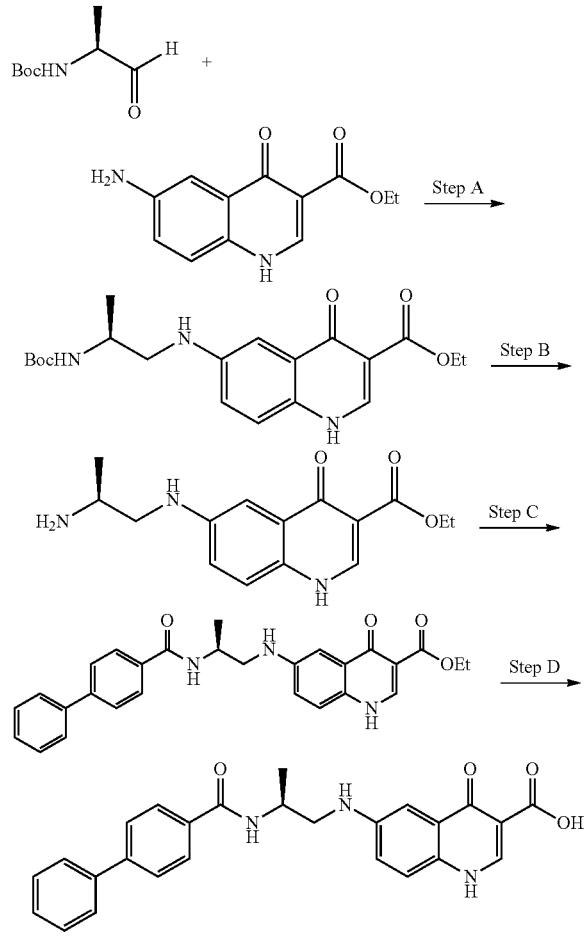

Step A: (S)-ethyl 6-((2-((tert-butoxycarbonyl)amino)propyl)amino)-4-oxo-1,4-dihydroquinoline-3-carboxylate A mixture of ethyl 6-amino-4-oxo-1,4-dihydroquinoline-3-carboxylate (200 mg, 0.86 mmol), (S)-tert-butyl (1-oxopropan-2-yl)carbamate (150 mg, 0.86 mmol) and acetic acid (1 ml) in anhydrous methanol (15 ml) was refluxed for 16 h with stirring. After cooling, NaBH$_3$CN (109 mg, 1.72 mmol) was added, and the mixture was stirred in an ice-water bath for 1 h, then further refluxed for 3 h. The solvent was evaporated and the residue was added methanol (15 ml) again. The formed precipitate was collected by filtration and purified by column chromatography eluting with dichloromethane/methanol 10:1 v/v to give the Boc-protected intermediate (S)-ethyl 6-((2-(((tert-butoxycarbonyl)amino)propyl)amino)-4-oxo-1,4-dihydroquinoline-3-carboxylate as a light brown solid (320 mg, 95% yield). LC-MS (ESI): m/z [M+H]$^+$ calcd. For C$_{20}$H$_{28}$N$_3$O$_5$: 390.20, found: 390.30.

Step B: (S)-ethyl 6-((2-aminopropyl)amino)-4-oxo-1,4-dihydroquinoline-3-carboxylate The Boc-protected intermediate (S)-ethyl 6-((2-(((tert-butoxycarbonyl)amino)propyl)amino)-4-oxo-1,4-dihydroquinoline-3-carboxylate (250 mg, 0.64 mmol) was dissolved in DCM (20 ml). CF$_3$COOH (5 ml) was added and the reaction mixture stirred at room temperature for 1 hour. Concentration in vacuum gave a brown solid which was dissolved in ethyl acetate and washed by aq. NaHCO$_3$. Collect the organic solvent and concentrate in vacuum to give a brown solid which was then purified by column chromatography eluting with dichloromethane/methanol 10:1 v/v to afford the title compound (170 mg, 91% yield). LC-MS (ESI): m/z [M+H]$^+$ calcd. For C$_{15}$H$_{20}$N$_3$O$_3$: 290.15, found: 290.20.

Step C: (S)-ethyl 6-((2-([1,1'-biphenyl]-4-ylcarboxamido)propyl)amino)-4-oxo-1,4-dihydroquinoline-3-carboxylate Biphenyl-4-carboxylic acid (50 mg, 0.25 mmol), HOBt (38 mg, 0.28 mmol) and HBTU (106 mg, 0.28 mmol) were dissolved in dry dimethylformamide (DMF, 10 ml). The mixture was stirred at room temperature for 15 min. (S)-ethyl 6-((2-aminopropyl)amino)-4-oxo-1,4-dihydroquinoline-3-carboxylate (73 mg, 0.25 mmol) and N,N-Diisopropylethylamine (0.134 ml, 0.76 mmol) were then added and the resulting mixture was stirred at room temperature overnight. DMF was removed by rotary evaporator, Ethyl acetate and water were then added. The formed precipitate was collected by filtration and washed by ethyl acetate to give (S)-ethyl 6-((2-([1,1'-biphenyl]-4-ylcarboxamido)propyl)amino)-4-oxo-1,4-dihydroquinoline-3-carboxylate (85 mg, 71% yield). LC-MS (ESI): m/z [M+H]$^+$ calcd. For C$_{28}$H$_{28}$N$_3$O$_4$: 470.21, found: 484.20.

Step D: (S)-6-((2-([1,1'-biphenyl]-4-ylcarboxamido)propyl)amino)-4-oxo-1,4-dihydroquinoline-3-carboxylic acid To a solution of compound (S)-ethyl 6-((2-([1,1'-biphenyl]-4-ylcarboxamido)propyl)amino)-4-oxo-1,4-dihydroquinoline-3-carboxylate (80 mg, 0.17 mmol) in Methanol (4 ml) and H$_2$O (4 ml), KOH (116 mg, 2.06 mmol) was added. The obtained mixture was stirred at 60° C. for 16 hours. The mixture was brought to 0° C., carefully acidified with 1N HCl until pH=1. The formed precipitate was collected by filtration and purified by HPLC to furnish the desired product Example 75 as an off-white solid (58 mg, 77% yield). LC-MS (ESI): m/z [M−H]$^−$ calcd. For C$_{26}$H$_{22}$N$_3$O$_4$: 440.16, found: 440.20. Purity: >95% (UV, λ=254 nm).

Examples 76 to 98 were prepared according to the procedure described above for Example 75.

TABLE 3

Examples 75-98

| Compound | Structure | Analytical Data | IC$_{50}$ (μm) |
|---|---|---|---|
| 75 | 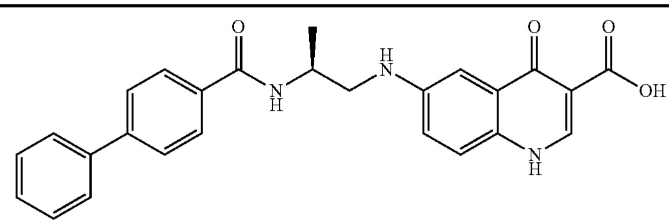 | MS: 440 (M − H)$^−$ | 6.2 |

TABLE 3-continued

Examples 75-98

| Compound | Structure | Analytical Data | IC$_{50}$ (μm) |
|---|---|---|---|
| 76 | 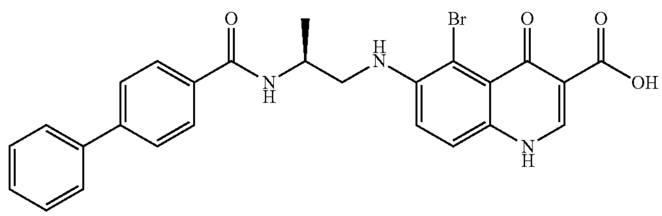 [SMILES: C[C@@H](CNc1ccc2[nH]cc(C(=O)O)c(=O)c2c1Br)NC(=O)c1ccc(-c2ccccc2)cc1] | MS: 518 (M − H)$^-$ | 2.1 |
| 77 | 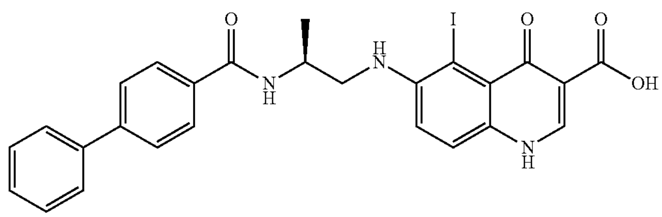 [SMILES: C[C@@H](CNc1ccc2[nH]cc(C(=O)O)c(=O)c2c1I)NC(=O)c1ccc(-c2ccccc2)cc1] | MS: 566 (M − H)$^-$ | n.d. |
| 78 | 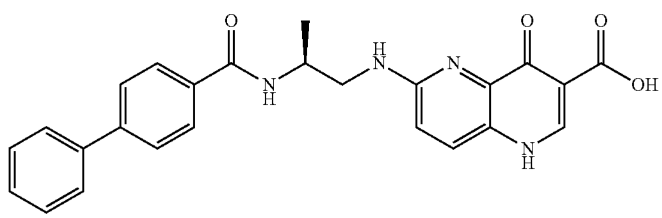 [SMILES: C[C@@H](CNc1ccc2[nH]cc(C(=O)O)c(=O)c2n1)NC(=O)c1ccc(-c2ccccc2)cc1] | MS: 441 (M − H)$^-$ | n.d. |
| 79 | 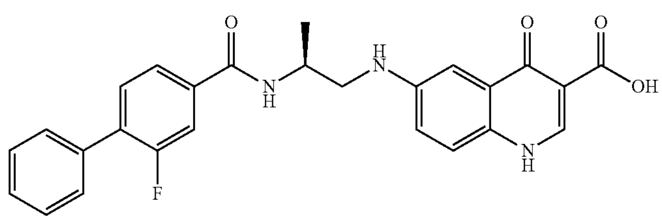 [SMILES: C[C@@H](CNc1ccc2[nH]cc(C(=O)O)c(=O)c2c1)NC(=O)c1ccc(-c2ccccc2)c(F)c1] | MS: 458 (M − H)$^-$ | n.d. |
| 80 | 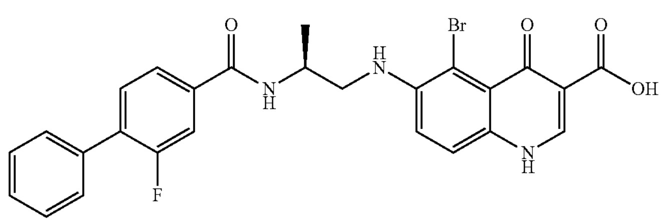 [SMILES: C[C@@H](CNc1ccc2[nH]cc(C(=O)O)c(=O)c2c1Br)NC(=O)c1ccc(-c2ccccc2)c(F)c1] | MS: 536 (M − H)$^-$ | n.d. |
| 81 | 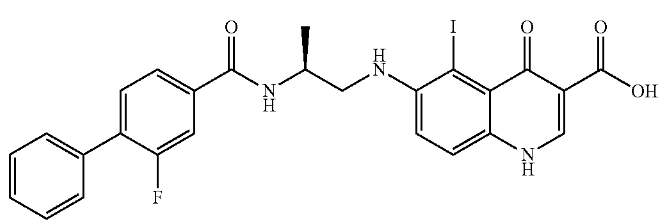 [SMILES: C[C@@H](CNc1ccc2[nH]cc(C(=O)O)c(=O)c2c1I)NC(=O)c1ccc(-c2ccccc2)c(F)c1] | MS: 584 (M − H)$^-$ | n.d. |
| 82 | 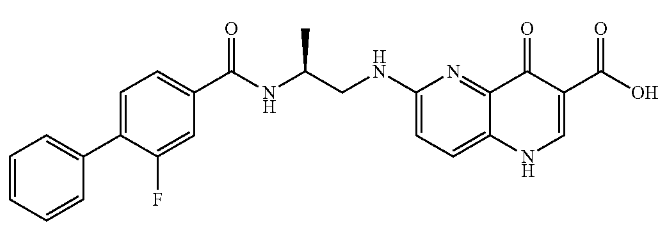 [SMILES: C[C@@H](CNc1ccc2[nH]cc(C(=O)O)c(=O)c2n1)NC(=O)c1ccc(-c2ccccc2)c(F)c1] | MS: 459 (M − H)$^-$ | n.d. |

TABLE 3-continued

Examples 75-98

| Compound | Structure | Analytical Data | IC$_{50}$ (μm) |
|---|---|---|---|
| 83 | 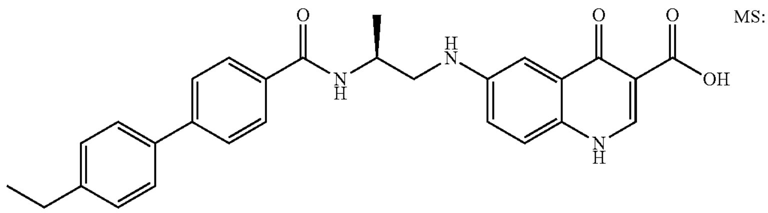 | MS: 468 (M − H)⁻ | n.d. |
| 84 | 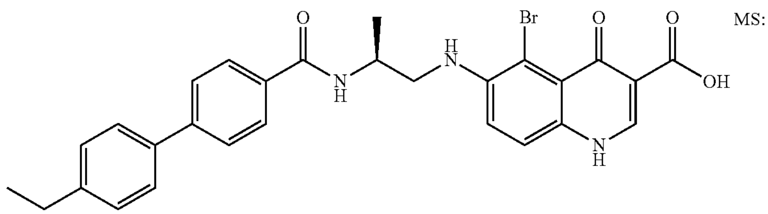 | MS: 546 (M − H)⁻ | n.d. |
| 85 | 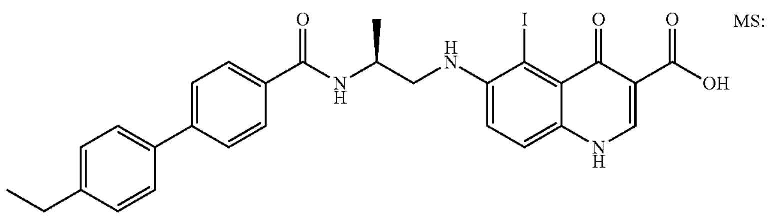 | MS: 594 (M − H)⁻ | n.d. |
| 86 | 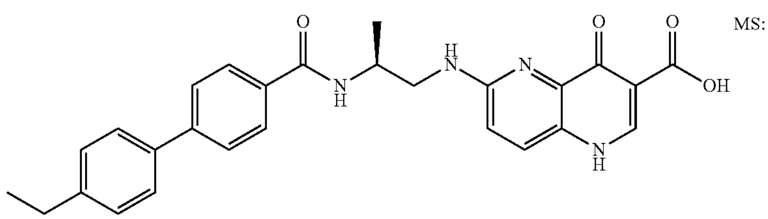 | MS: 569 (M − H)⁻ | n.d. |
| 87 | 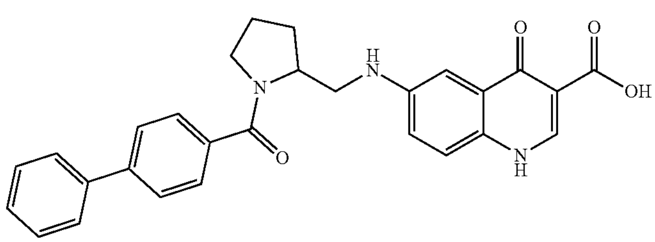 [SMILES: O=C(O)c1c[nH]c2ccc(NCC3CCCN3C(=O)c3ccc(-c4ccccc4)cc3)cc2c1=O] | MS: 566 (M − H)⁻ | 4.0 |
| 88 | 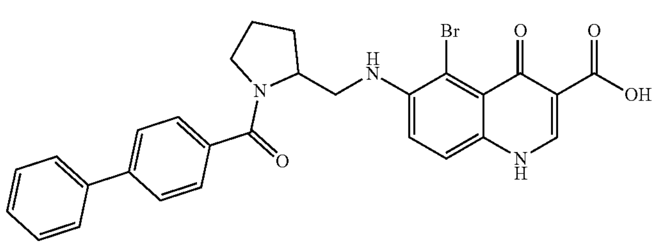 [SMILES: O=C(O)c1c[nH]c2ccc(NCC3CCCN3C(=O)c3ccc(-c4ccccc4)cc3)c(Br)c2c1=O] | MS: 544 (M − H)⁻ | 1.8 |

TABLE 3-continued

Examples 75-98

| Compound | Structure | Analytical Data | IC$_{50}$ (μm) |
|---|---|---|---|
| 89 | 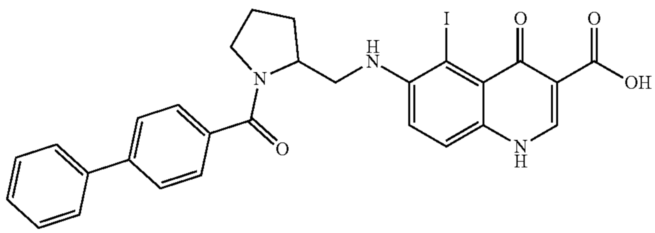 [SMILES: O=C(O)c1c[nH]c2ccc(NCC3CCCN3C(=O)c3ccc(-c4ccccc4)cc3)c(I)c2c1=O] | MS: 592 (M − H)$^-$ | n.d. |
| 90 | 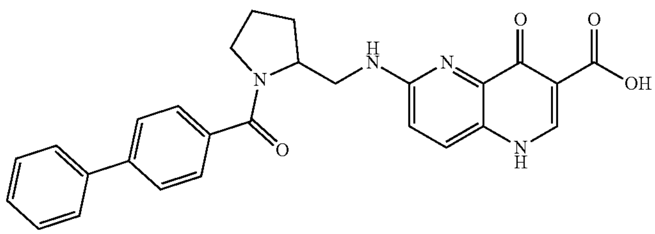 [SMILES: O=C(O)c1c[nH]c2ccc(NCC3CCCN3C(=O)c3ccc(-c4ccccc4)cc3)nc2c1=O] | MS: 467 (M − H)$^-$ | n.d. |
| 91 | 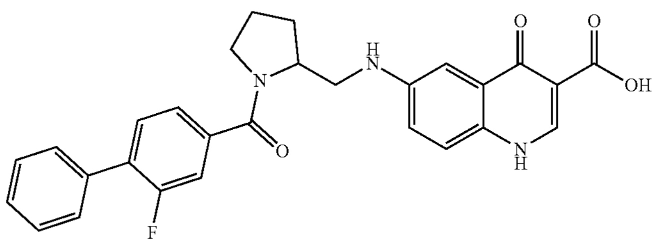 [SMILES: O=C(O)c1c[nH]c2ccc(NCC3CCCN3C(=O)c3ccc(-c4ccccc4)c(F)c3)cc2c1=O] | MS: 484 (M − H)$^-$ | n.d. |
| 92 | 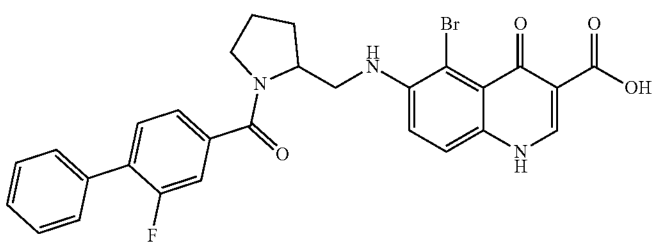 [SMILES: O=C(O)c1c[nH]c2ccc(NCC3CCCN3C(=O)c3ccc(-c4ccccc4)c(F)c3)c(Br)c2c1=O] | MS: 562 (M − H)$^-$ | n.d. |
| 93 | 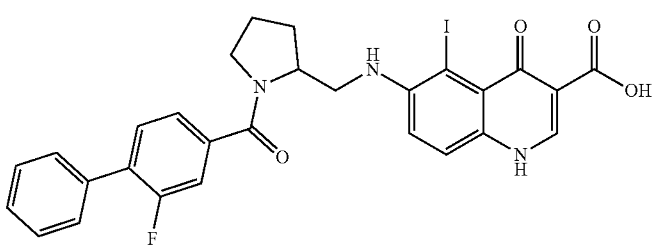 [SMILES: O=C(O)c1c[nH]c2ccc(NCC3CCCN3C(=O)c3ccc(-c4ccccc4)c(F)c3)c(I)c2c1=O] | MS: 610 (M − H)$^-$ | n.d. |
| 94 | 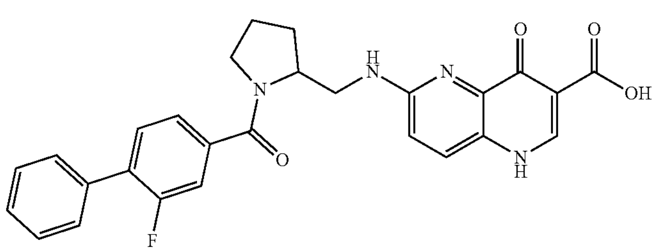 [SMILES: O=C(O)c1c[nH]c2ccc(NCC3CCCN3C(=O)c3ccc(-c4ccccc4)c(F)c3)nc2c1=O] | MS: 485 (M − H)$^-$ | n.d. |

TABLE 3-continued

Examples 75-98

| Compound | Structure | Analytical Data | IC$_{50}$ (μm) |
|---|---|---|---|
| 95 | 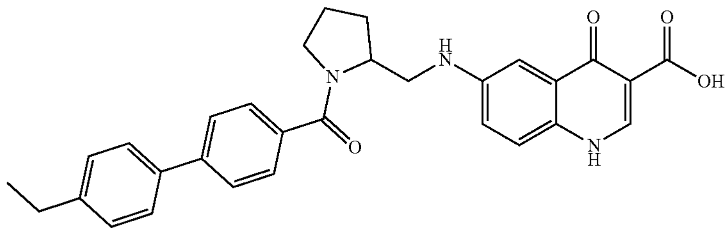 [SMILES: CCc1ccc(-c2ccc(C(=O)N3CCCC3CNc3ccc4[nH]cc(C(=O)O)c(=O)c4c3)cc2)cc1] | MS: 494 (M − H)⁻ | n.d. |
| 96 | 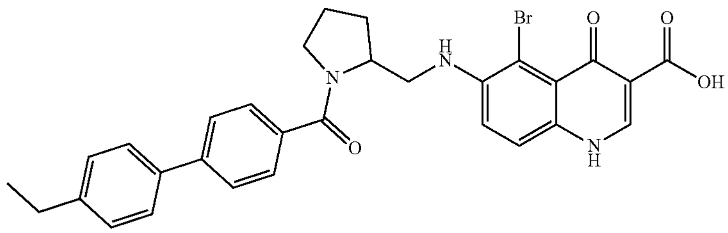 [SMILES: CCc1ccc(-c2ccc(C(=O)N3CCCC3CNc3ccc4[nH]cc(C(=O)O)c(=O)c4c3Br)cc2)cc1] | MS: 572 (M − H)⁻ | n.d. |
| 97 | 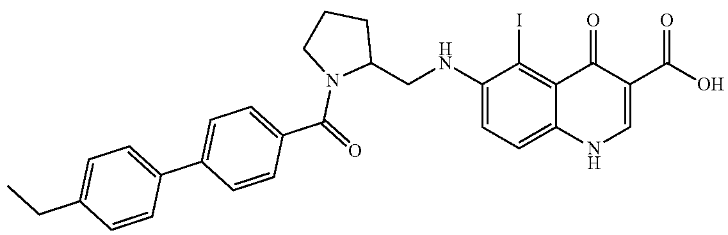 [SMILES: CCc1ccc(-c2ccc(C(=O)N3CCCC3CNc3ccc4[nH]cc(C(=O)O)c(=O)c4c3I)cc2)cc1] | MS: 620 (M − H)⁻ | n.d. |
| 98 | 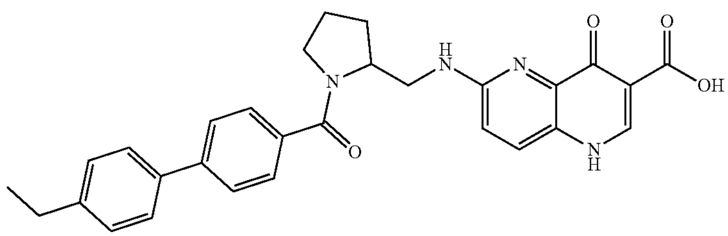 [SMILES: CCc1ccc(-c2ccc(C(=O)N3CCCC3CNc3ccc4[nH]cc(C(=O)O)c(=O)c4n3)cc2)cc1] | MS: 495 (M − H)⁻ | n.d. |

Assays

Compounds of the invention were assessed for their ability to selectively inhibit LYP activity. The inhibitory properties of the compounds of the invention described herein can be evidenced by testing in any one of the following assays.

Expression and Purification of the LYP Catalytic Domain

N-terminal (His)$_6$-tagged LYP catalytic domain (residues 1-303) was subcloned into pET28a. For protein expression, the LYP expressing construct was transformed into *Escherichia coli* BL21-(DE3). Transformed cells were grown at 37° C. in Luria broth (LB) containing 100 μg/mL ampicillin for 4 h until the OD600 reached 0.6 and then induced for growth overnight at room temperature with 0.4 mM IPTG. Cells were harvested by centrifugation (6000 rpm for 15 min at 4° C.), and the cell pellets from 1.5 L of LB medium were suspended in 30 mL of ice-cold lysis buffer consisting of 5 mM imidazole, 500 mM NaCl, 20 mM Tris-HCl (pH 7.9), 0.05 mg/mL trypsin inhibitor, and 0.1 mM PMSF. The suspensions were passed twice through a French press at 1000 psi, and the cell lysates were centrifuged at 4° C. for 30 min at 15000 rpm. The supernatants were mixed with 2 mL of Ni-NTA agarose (His*Bind Resin) (Qiagen) at 4° C. for 1 h, and then the mixture was transferred to an empty column. The column was washed with 200 mL of binding buffer (5 mM imidazole, 500 mM NaCl, 20 mM Tris-HCl (pH 7.9)), followed by 20 mL of wash buffer (20 mM imidazole, 500 mM NaCl, 20 mM Tris-HCl (pH 7.9)), and then eluted with 20 mL of elution buffer (200 mM imidazole, 500 mM NaCl, 20 mM Tris-HCl (pH 7.9), 5 mM DTT). The elution was dialyzed for 6 h at 4° C. against 1 L buffer A (50 mM NaCl, 20 mM MES (pH 5.8), 1 mM EDTA) and then loaded onto a Mono S column equilibrated at 4° C. with buffer A. The column was washed with 10 mL of buffer A and then eluted with a 40 mL of linear gradient of 0-1 M NaCl in buffer A. The column fractions were analyzed by measuring the absorbance at 280 nm and by carrying out SDS-PAGE analysis. The fractions were combined, concentrated at 4° C. to <1 mL using an Amicon concentrator, and then loaded onto a gel filtration column Superdex 75. The column was eluted with buffer A, and then the fractions which contained protein were combined and concentrated to 8 mg/mL and stored at −80° C. The LYP preparation was shown to be homogeneous by SDS-PAGE analysis.

Enzyme Kinetic Assay

PTP activity was assayed using p-nitrophenyl phosphate (pNPP) as a substrate in 3,3-dimethylglutarate buffer (50 mM 3,3-dimethylglutarate, pH 7.0, 1 mM EDTA, 150 mM NaCl) at 25° C. The assays were performed in 96-well plates. Normally, to determine the $IC_{50}$ values for LYP, the reaction was initiated by the addition of enzyme (final concentration at 20 nM) to a reaction mixture (0.2 mL) containing 5.0 mM ($K_m$ for the substrate against Lyp) pNPP with serial dilutions. To determine the $IC_{50}$ values for other PTPs, the assays were carried out under the same conditions used for LYP except that the concentration of the pNPP was set at the corresponding $K_m$ value for each PTP. All PTPs used in the study were recombinant proteins prepared in-house. Concentration of compounds used to determine IC50 values ranged from 0.2- to 5-fold of the $IC_{50}$ values. The reaction rate was measured using a SpectraMax Plus 384 microplate spectrophotometer (Molecular Devices). To determine the mode of inhibition, the reactions were initiated by the addition of LYP (final concentration at 5 nM) to the reaction mixtures (0.2 mL) containing various concentrations of pNPP and inhibitor L-1 (Example 1). Data were fitted using SigmaPlot Enzyme Kinetics Module (Systat Software, Inc.).

Pharmacokinetics Study

Example 1 is a novel PTPN22 inhibitor with $IC_{50}$ as low as 1.4±0.2 µM. In order to study the effects of Example 1 in mouse model, pharmacokinetics data is required to understand its absorbance/distribution/metabolism/elimination (ADME) properties. The detailed experimental procedures and resulting pharmacokinetics parameters are present below.

Animal Dosing and Sample Collection for Pharmacokinetic Studies

Example 1 was first dissolved in DMSO to make a 20 mg/ml solution. Then the solution was further diluted to a 2 mg/ml solution for which the formulation is 10% DMSO-85% PBS-5% Cremophor EL (CrEL). Each mouse was administered a single IP dose of 10 mg/kg. The volume of each injection was about 100 µL according to the weight of mouse. At different time points (1 h, 1.5 h, 2 h, 2.5 h, 3 h, 6, 24 h), blood samples (50 µL) were collected and centrifuged to get the serum. The serum (10 µL) were then mixed with acetonitrile (20 µL) and centrifuged. The supernatant was collected and subjected to Liquid Chromatography/Mass Spectrometry analysis.

Liquid Chromatography/Mass Spectrometry Analysis

The Liquid Chromatography/Mass Spectrometry (LC/MS) analysis was carried out on a Agilent 1260 analytic HPLC system and an Agilent 6470 Triple Quadrupole MS detector, equipped with a Kinetex 2.6 um C18 column (3 mm×50 mm), eluted with 0-100% MeOH—H$_2$O with 0.1% (w/v) formic acid at 0.7 mL/min flow-rate (gradient method: 1.2 min 0-10% MeOH linear gradient, 1.5 min 10-90% MeOH linear gradient, followed by 1.3 min 90-100% MeOH, followed by 2.5 min 100% MeOH), MS detector were set at single ion mode (SIM), monitoring the negative charge 454.2 (M-1). The detection limit for Example 1 is 100 nM at 4 µL sample injection.

Data Analysis

Figure 3:
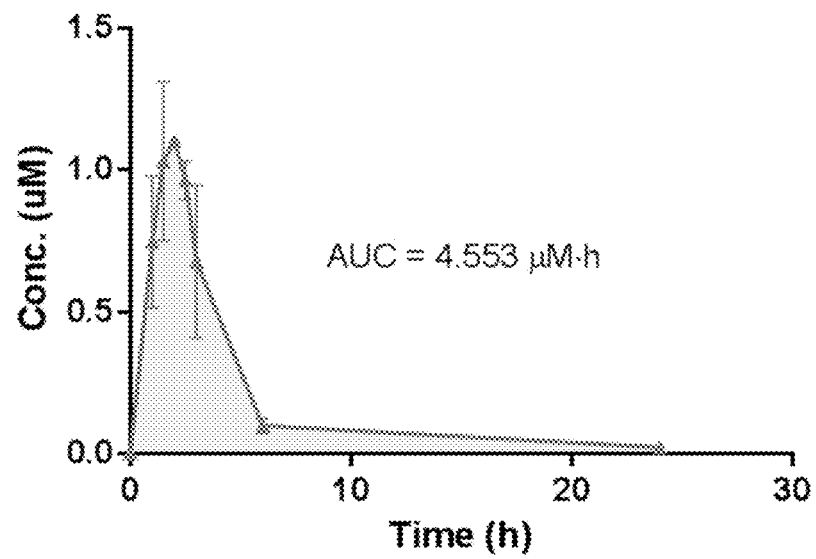
FIG. 3 and FIG. 4 illustrate in vivo pharmacokinetics data based on mass spectrometry quantification at 0 h, 1.0 h, 1.5 h, 2.0 h, 2.5 h, 3.0 h, 6.0 h, and 24.0 h from time of intraperitoneal injection of Example 1 for three mice are shown.
Figure 4:
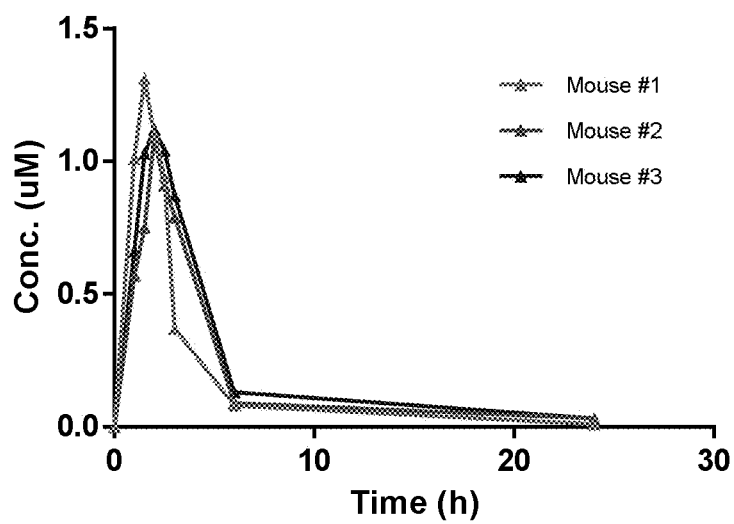

The pharmacokinetic parameters were calculated in GraphPad Prism 6, and the results are shown in Table 4 below. The pharmacokinetic curve for Example 1 is shown in FIGS. 3&4.

TABLE 4

The Pharmacokinetic Data for Example 1

| Mouse | Conc. | formulation | IP dose | $C_{max}$ (µM) | $t_{max}$ (h) | $k_e$ | $t_{1/2}$ (h) |
|---|---|---|---|---|---|---|---|
| #1 | 2 mg/ml | 10% DMSO-85% PBS-5% CrEL | 10 mg/kg | 1.31 | 1.5 | 0.583 | 1.189 |
| #2 | 2 mg/ml | 10% DMSO-85% PBS-5% CrEL | 10 mg/kg | 1.09 | 2 | 0.259 | 2.681 |
| #3 | 2 mg/ml | 10% DMSO-85% PBS-5% CrEL | 10 mg/kg | 1.12 | 2 | 0.285 | 2.428 |
| Average | 2 mg/ml | 10% DMSO-85% PBS-5% CrEL | 10 mg/kg | 1.11 | 2 | 0.341 | 2.031 |

Figure 5:
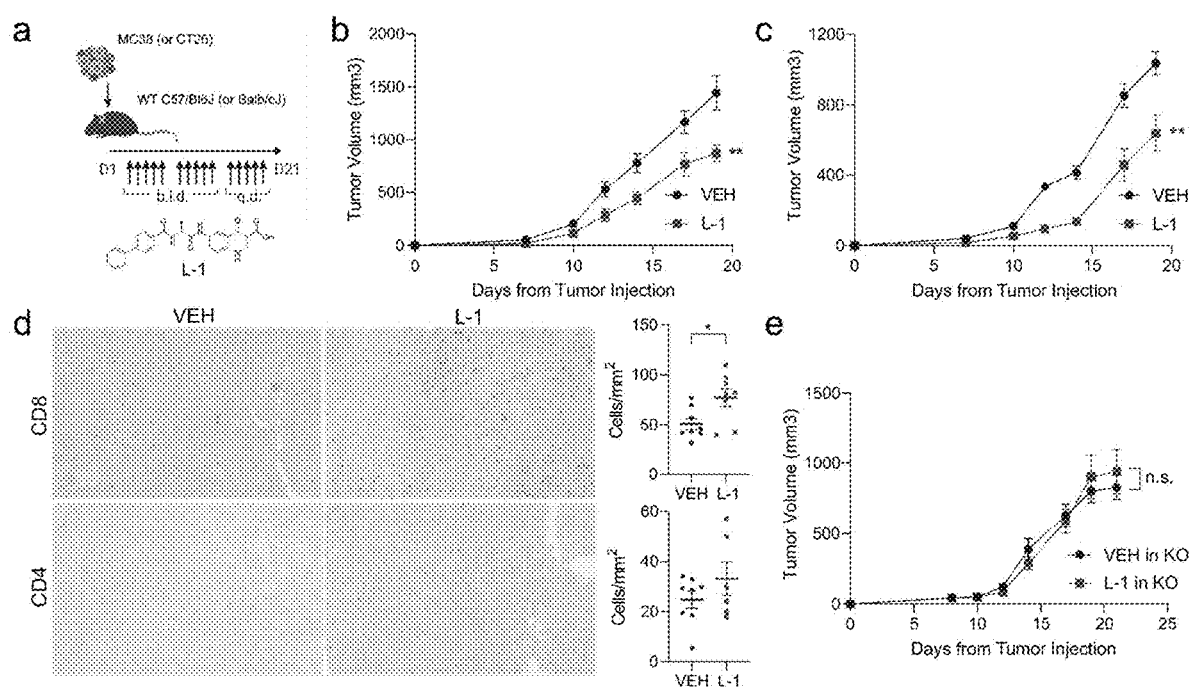
FIG. 5 illustrates that Example 1 displays efficacious in vivo activity in mouse model for cancer immunotherapy.

LYP Inhibitor Example 1 Displays Efficacious In Vivo Activity in Mouse Model for Cancer Immunotherapy FIG. 5 illustrates that Example 1 displays efficacious in vivo activity in mouse model for cancer immunotherapy. As observed in the PTPN22 (LYP) KO model, treatment of WT mice with Example 1 (a) led to significantly reduced MC38 tumor growth compared to the vehicle-injected control group (b). We further tested the effect of Example 1 on another syngeneic immunocompetent model, CT26 in Balb/c mice, which showed similar antitumor effects (c). Analysis of the MC38 tumors with immunohistochemistry demonstrated that Example 1 induced increased infiltration of CD4+ and CD8+ T cells (d). Moreover, profiling both MC38 and CT26 tumor immune infiltrates showed significantly improved presence of multiple immune cell types and T cell subtypes in Example 1 treated tumors. To test whether the effects of Example 1 treatment could be attributable to off-target effects, we treated MC38 tumors in PTPN22 KO mice with either vehicle or Example 1 injection. No significant differences in tumor growth were noted, suggesting that the Example 1-mediated protective effects against tumor growth were PTPN22 (LYP)- and host-specific (e).

In conclusion, Example 1 exhibits strong in vivo antitumor activity which closely phenocopies the PTPN22 KO mice, indicating little off-target activities.

In one embodiment, the present disclosure provides a compound of formula I:

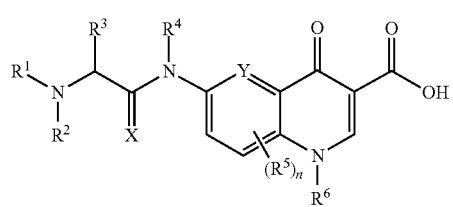

I or a stereoisomer, tautomer, solvate, derivative, pharmaceutically acceptable salt thereof, wherein:

$R^1$ and $R^2$ independently represents hydrogen, optionally substituted alkyl, optionally substituted cycloalkyl, optionally substituted cycloalkylalkyl, alkylcarbonyl provided that said alkylcarbonyl is not methylcarbonyl, optionally substituted cycloalkylcarbonyl, optionally substituted cycloalkylalkylcarbonyl, optionally substituted aryl, optionally substituted aralkyl, optionally substituted arylcarbonyl, optionally substituted aralkylcarbonyl, optionally substituted alkoxyalkyl, optionally substituted hydroxyalkyl, optionally substituted heterocyclyl, optionally substituted heterocyclylalkyl, optionally substituted heterocyclycarbonyl, optionally substituted heterocyclyalkylcarbonyl, optionally substituted carbocyclyl, optionally substituted carbocyclylalkyl, optionally substituted amino, optionally substituted alkyl-SO$_2$—, optionally substituted aryl-SO$_2$—, optionally substituted heterocyclyl-SO$_2$—, optionally substituted amino-SO$_2$—, or R$^1$ and R$^2$ together with the N atom to which they are attached form a 5-10 membered heterocyclic ring which optionally comprise a second heteroatom selected from nitrogen or oxygen and, wherein the heterocyclic ring is optionally substituted;

R$^3$ is H, optionally substituted alkyl, optionally substituted alkenyl, optionally substituted alkynyl, optionally substituted cycloalkyl, optionally substituted aryl, optionally substituted heteroaryl, or optionally substituted heterocyclyl;

R$^4$ and R$^6$ independently represents hydrogen, optionally substituted alkyl, optionally substituted cycloalkyl, optionally substituted heterocycloalkyl, optionally substituted aryl and heteroaryl; optionally substituted aralkyl, or optionally substituted heteroaralkyl;

(R$^5$)$_n$, when n is 1 or 2, represents 1 to 2 —H, —F, —Cl, —Br, —I, —CFH$_2$, —CF$_2$H, —CF$_3$, —CN, —OH, —NO$_2$, —NH$_2$, —SO$_2$CH$_3$, SO$_2$NH$_2$, —SO$_2$NHCH$_3$, optionally substituted —CO$_2$-alkyl, optionally substituted NH(alkyl) or N(alkyl)$_2$, optionally substituted alkyl, optionally substituted alkenyl, optionally substituted alkoxy, optionally substituted S-alkyl, optionally substituted cycloalkyl, optionally substituted heterocycle, optionally substituted aryl or optionally substituted heteroaryl;

X is O or H, wherein —C=X— is —CH$_2$— when X is H, and wherein at least one of R$^1$ and R$^2$ is optionally substituted arylcarbonyl when X is H, and one of R$^1$ and R$^2$ can join R$^3$ to form a ring; and Y is C—R$^5$ or N.

In one embodiment of the present disclosure regarding the compound of formula I, wherein X is O.

In one embodiment of the present disclosure regarding the compound of formula I, wherein X is H to make —C=X— a CH$_2$ group.

In one embodiment of the present disclosure regarding the compound of formula I, wherein Y is CH, C—F, C—Cl, C—Br, C—I or N.

In one embodiment of the present disclosure regarding the compound of formula I, wherein R$^4$ is H.

In one embodiment of the present disclosure regarding the compound of formula I, wherein R$^6$ is H.

In one embodiment of the present disclosure regarding the compound of formula I, wherein R$^3$ is an optionally substituted C$_1$-C$_4$ alkyl.

In one embodiment of the present disclosure regarding the compound of formula I, wherein R$^4$ and R$^6$ are H, and R$^3$ is an optionally substituted C$_1$-C$_4$ alkyl.

In one embodiment of the present disclosure regarding the compound of formula I, wherein at least one of R$^1$ and R$^2$ is H.

In one embodiment of the present disclosure regarding the compound of formula I, wherein R$^4$ and R$^6$ are H, R$^3$ is an optionally substituted C$_1$-C$_4$ alkyl, and at least one of R$^1$ and R$^2$ is H.

In one embodiment of the present disclosure regarding the compound of formula I, wherein one of R$^1$ and R$^2$ is an optionally substituted arylcarbonyl, optionally substituted aralkylcarbonyl, optionally substituted heterocyclycarbonyl, optionally substituted heterocyclyalkylcarbonyl, and one of R$^1$ and R$^2$ is H.

In one embodiment of the present disclosure regarding the compound of formula I, wherein one of R$^1$ and R$^2$ is an optionally substituted biphenylcarbonyl or phenylcarbonyl, and one of R$^1$ and R$^2$ is H.

In one embodiment of the present disclosure regarding the compound of formula I, wherein R$^1$-R$^6$, X. Y, and n can be any combination of the specific R$^1$-R$^6$, X. Y, and n in all the exemplified Examples 1-98.

In one embodiment of the present disclosure regarding the compound of formula I, the COOH groups of compounds can form derivatives such as but are not limited to esters amide, carbamates. The alkyl and aralkyl derivatives are examples of suitable esters amide, or carbamates. The methyl, ethyl, propyl, butyl and benzyl esters are preferred esters amide, or carbamates. The methyl and ethyl esters amide, or carbamates are especially preferred. Further examples of pharmaceutically suitable esters are compounds of formula I, wherein the hydroxyl groups can be esterified. Examples of such esters are formate, acetate, propionate, butyrate, isobutyrate, valerate, 2-methylbutyate, isovalerate and N, N-dimethylaminooacetate. Preferred esters are acetate and N, N-dimethylaminoacetate.

In one embodiment of the present disclosure regarding the compound of formula I, wherein the compound is selected from the group consisting of:

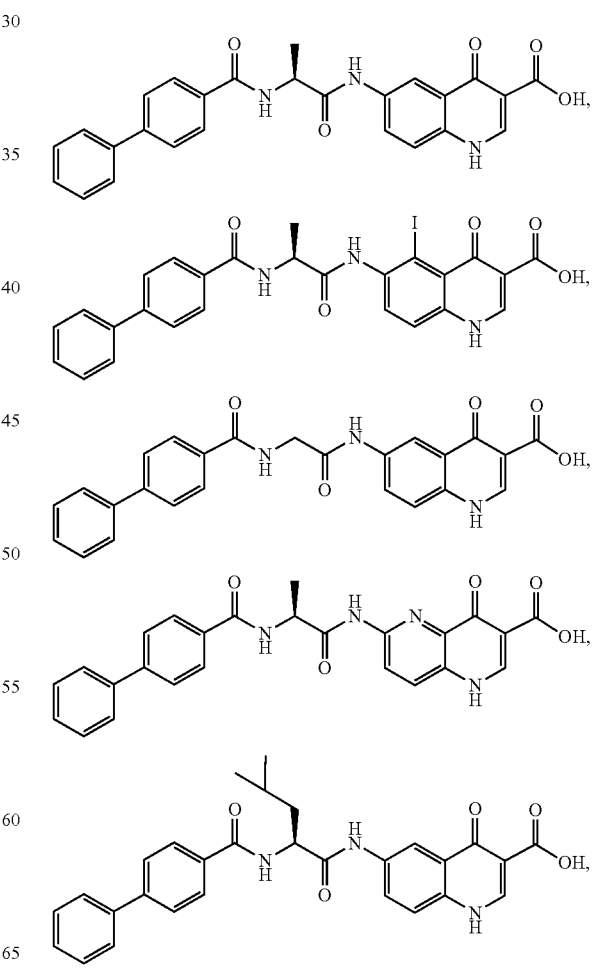

55
-continued
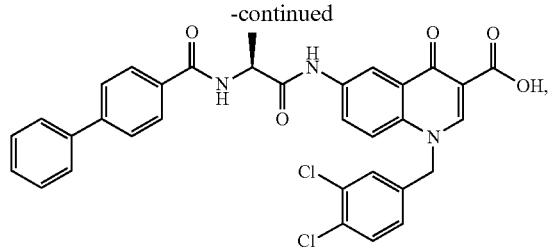
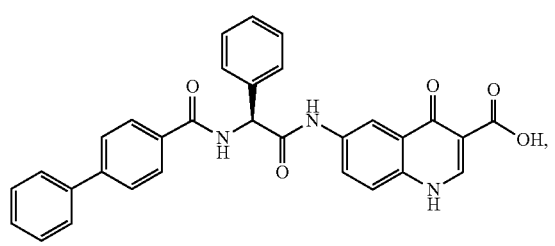
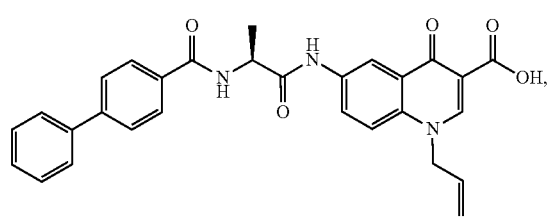
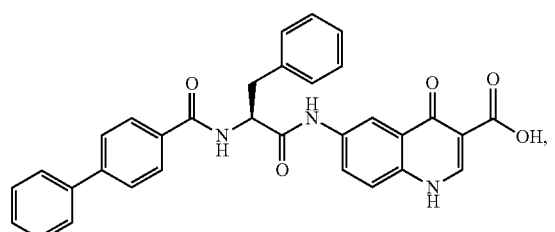
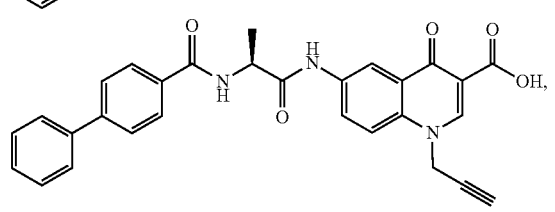
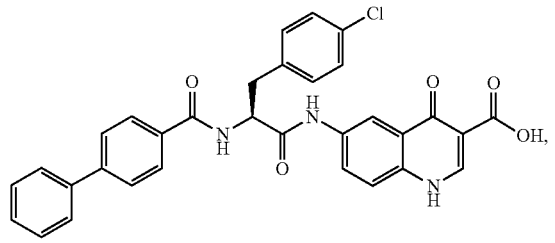
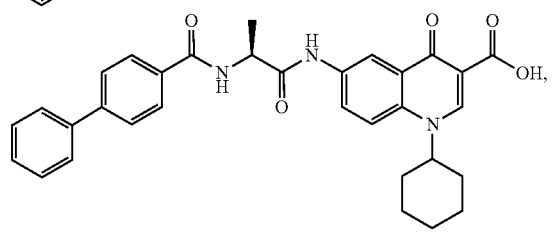
56
-continued
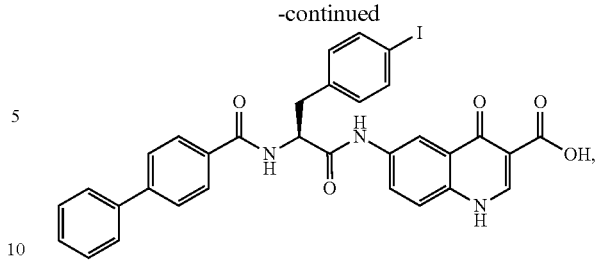
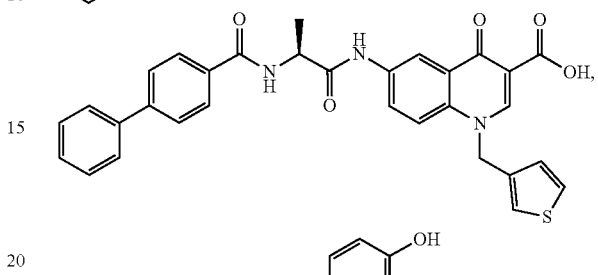
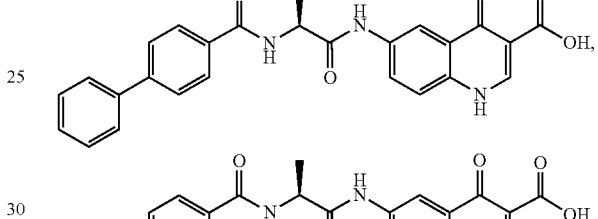
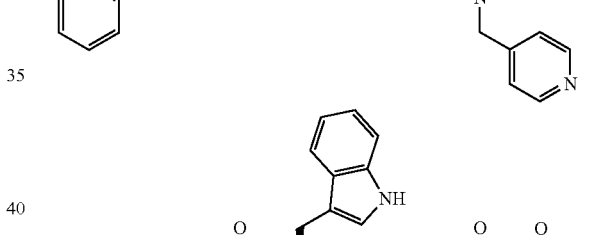
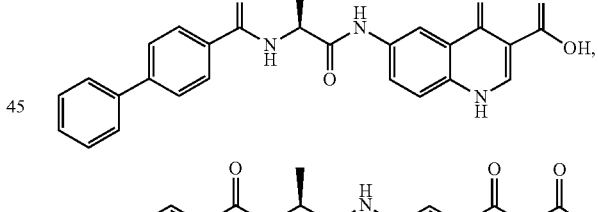
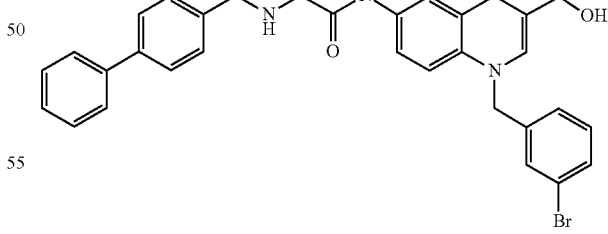
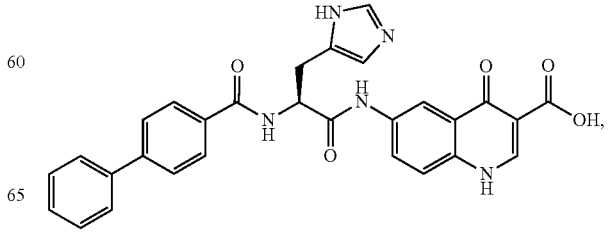

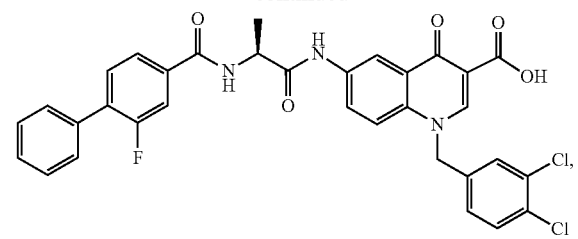
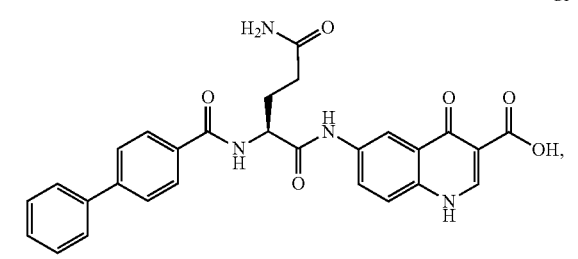
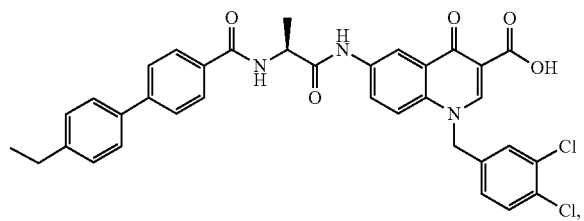
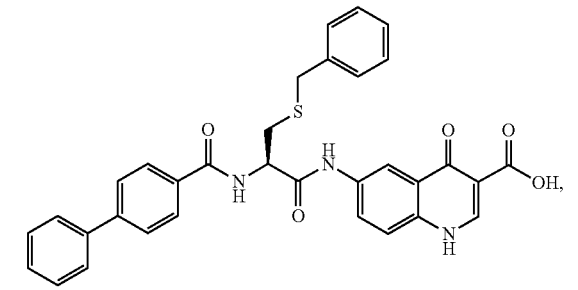
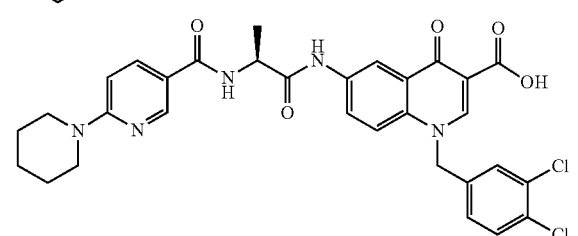
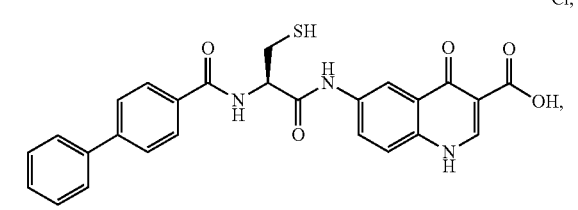
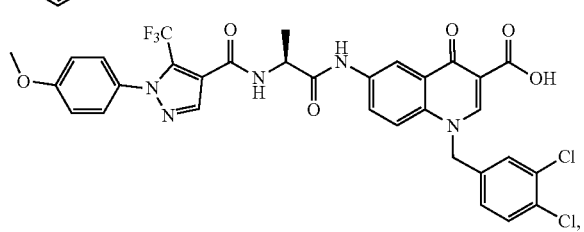
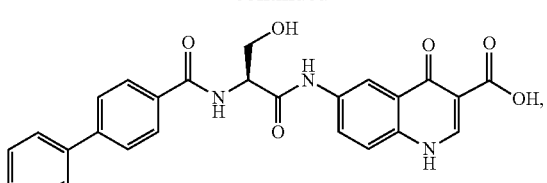
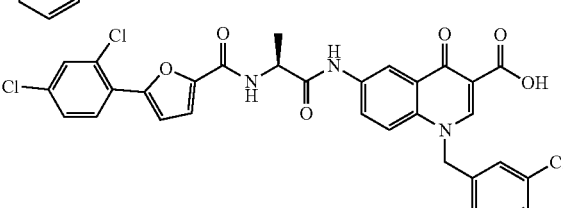
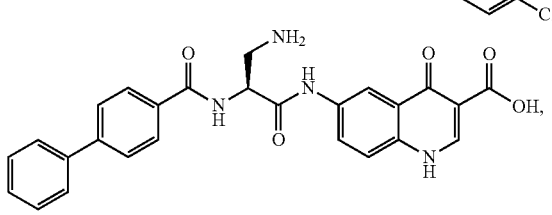
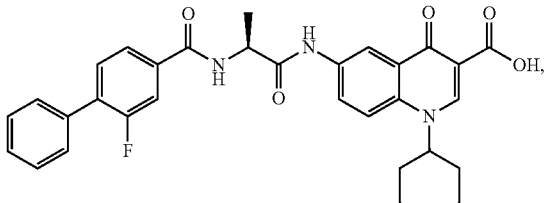
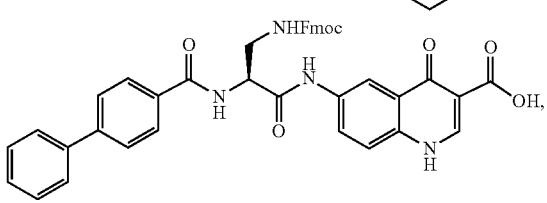
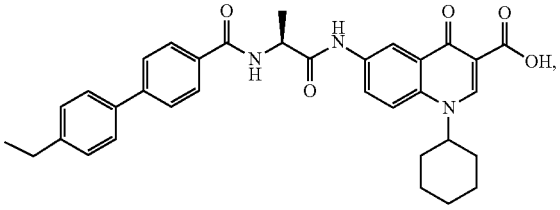
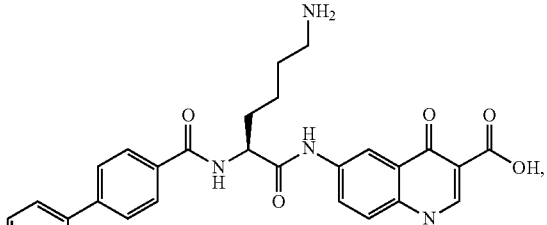

-continued
59
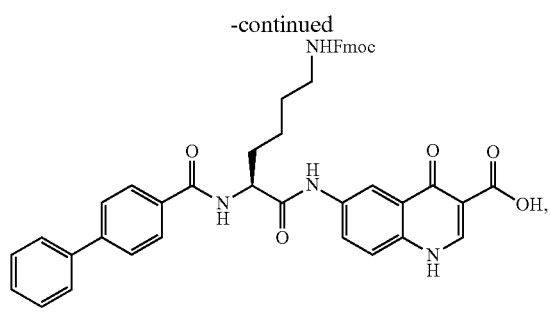
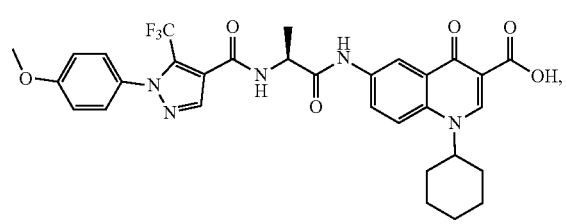
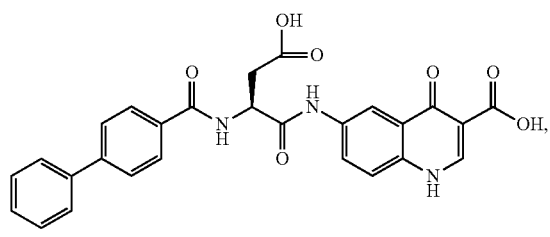
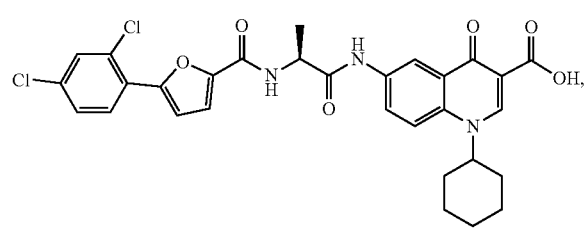
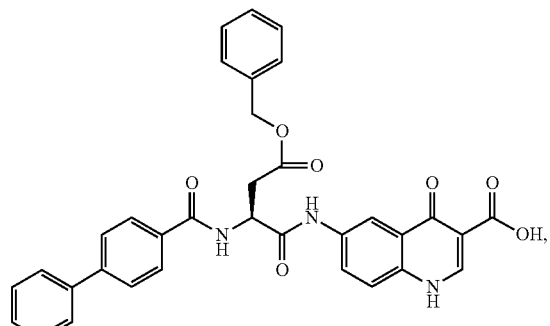
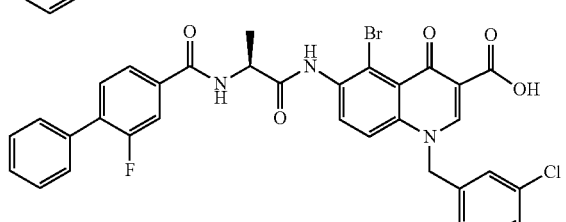
-continued
60
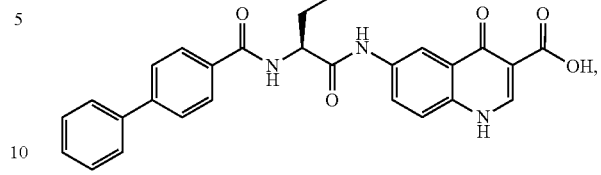
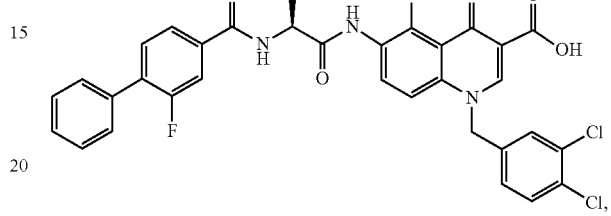
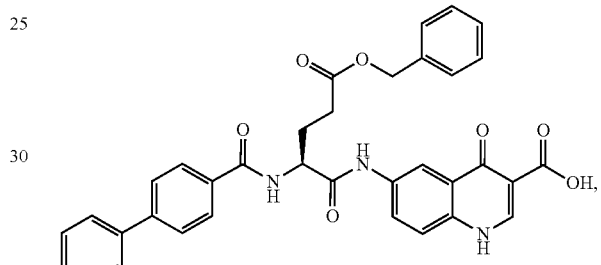
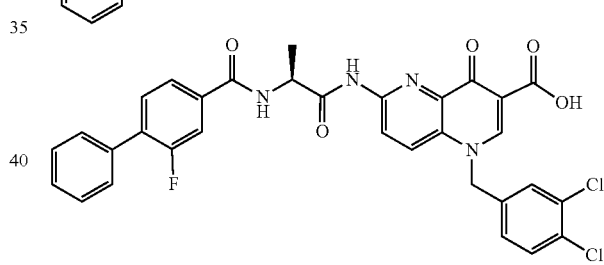
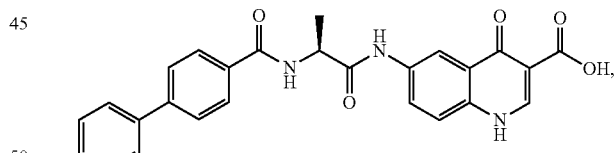
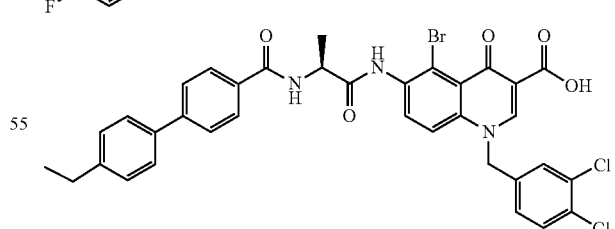
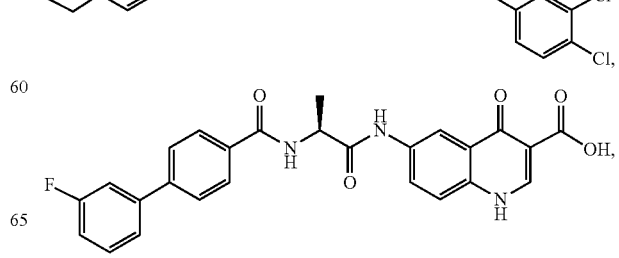

-continued
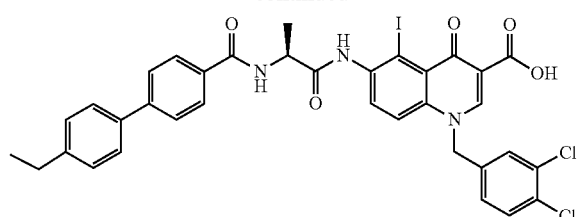
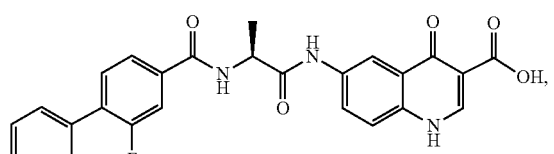
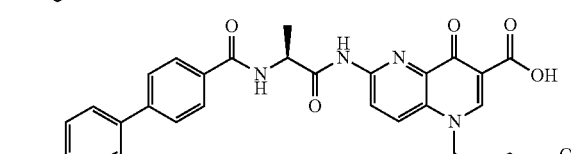
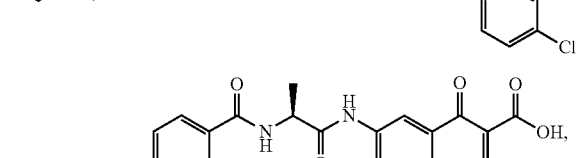
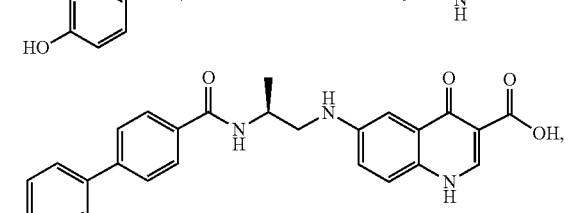
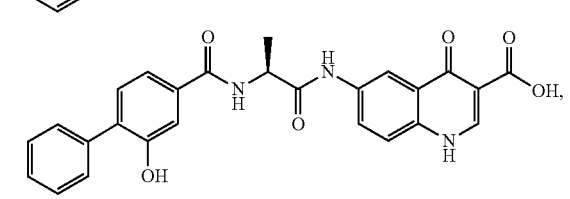
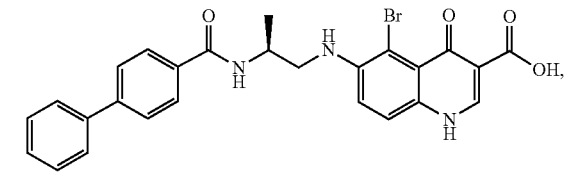
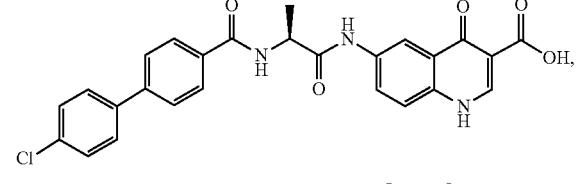
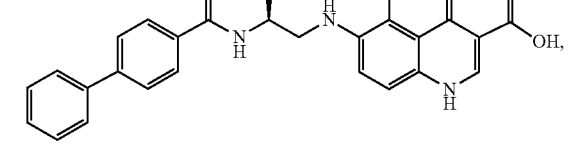
-continued
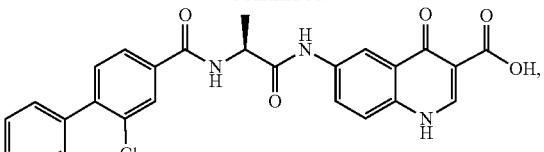
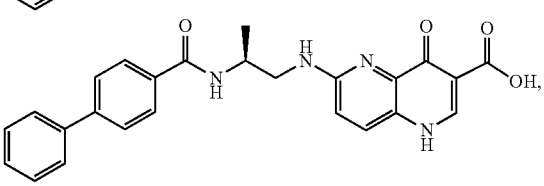
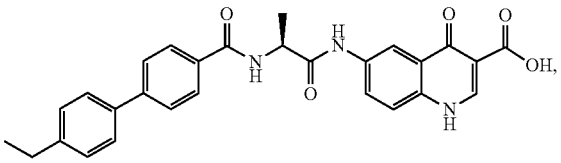
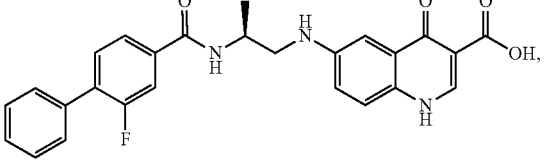
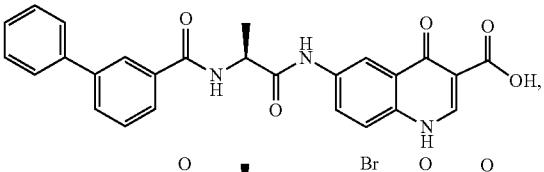
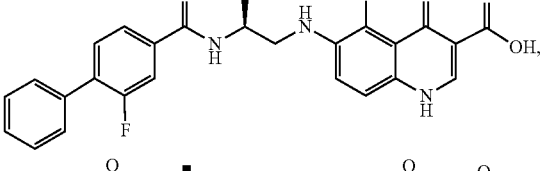
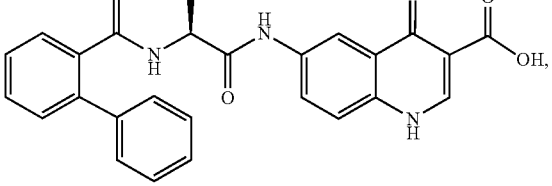
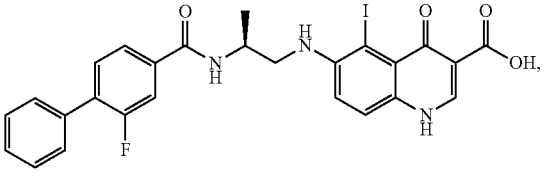
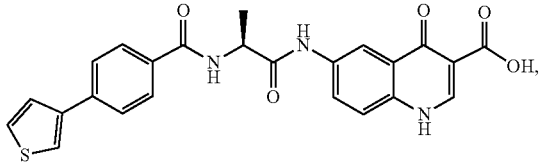
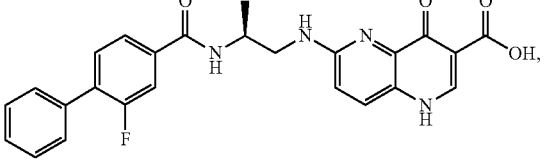

63
-continued
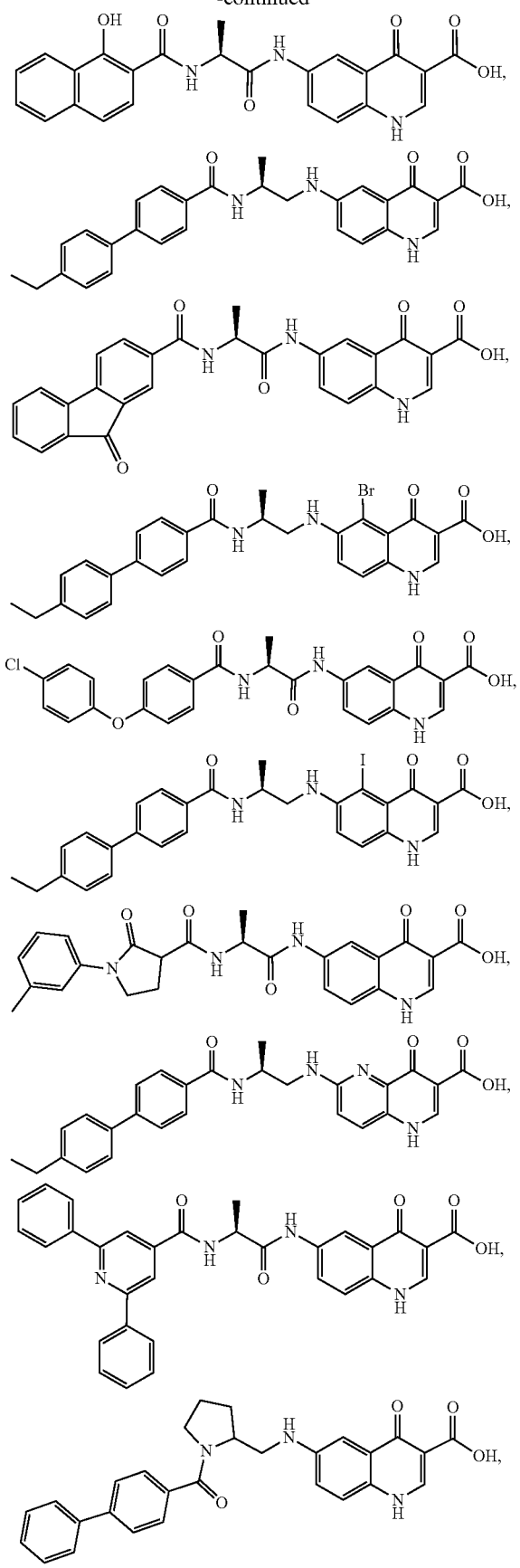
64
-continued
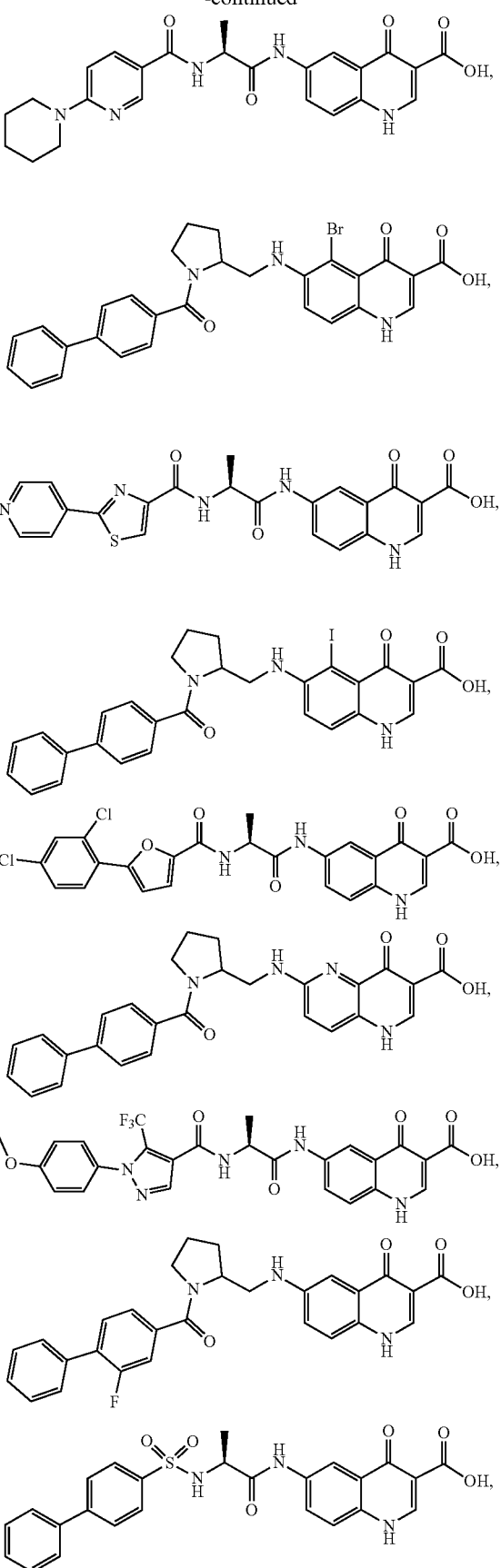

-continued

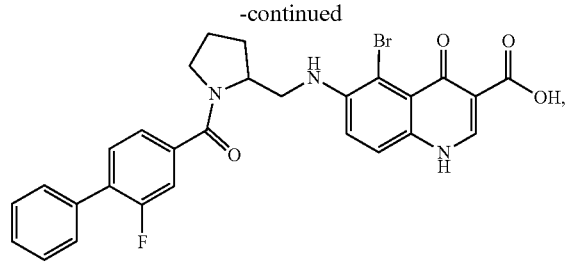
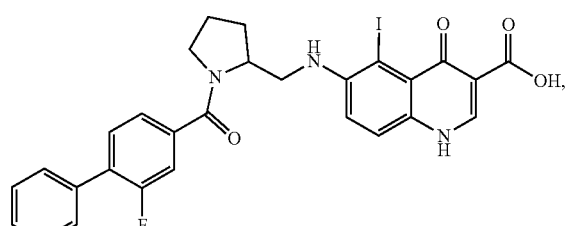
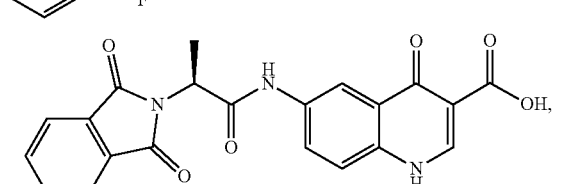
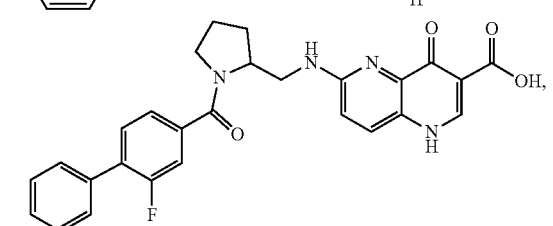
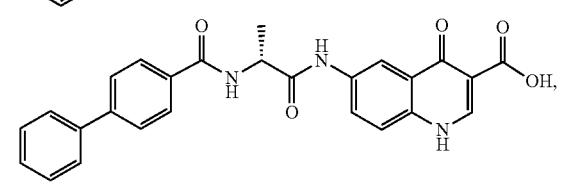
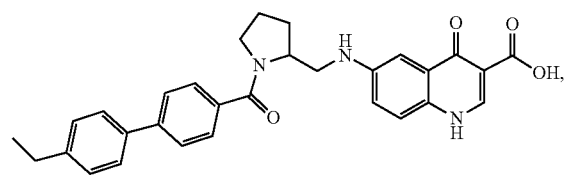
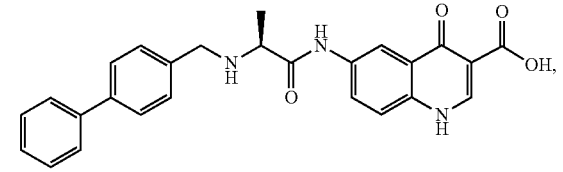

-continued

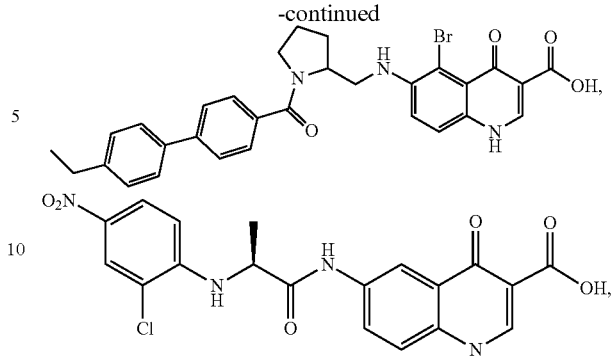
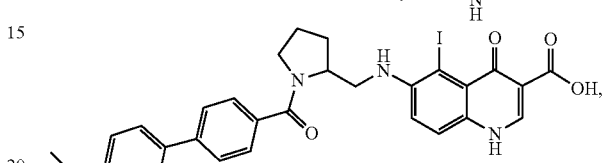
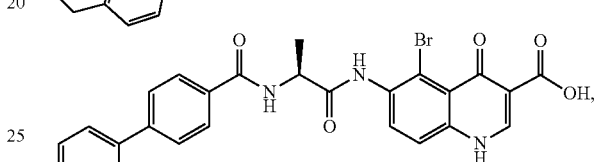
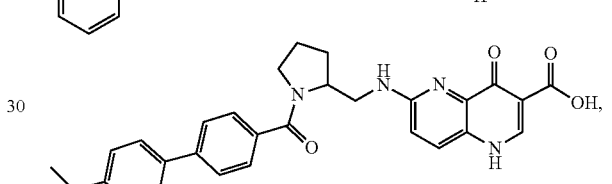

and a stereoisomer, tautomer, solvate, derivative, pharmaceutically acceptable salt thereof.

In one embodiment, the present disclosure provides a method of inhibiting LYP in a subject in need thereof, the method comprising administering to the subject a therapeutically effective amount of the compound of formula I, a therapeutically suitable a stereoisomer, tautomer, solvate, or salt thereof.

In one embodiment, the present disclosure provides a method of treating a patient having a disease or disorders associated with PTPN22 genetic polymorphism, including but is not limited to type 1 diabetes, rheumatoid arthritis, systemic lupus erythematosis, Graves' disease, Addison's disease, vitiligo, juvenile arthritis, Hashimoto thyroiditis, and other rarer diseases, with a therapeutically effective amount of the compound of formula I, a therapeutically suitable a stereoisomer, tautomer, solvate, or salt thereof.

In one embodiment, the present disclosure provides a method of cancer immunotherapy by inhibiting LYP activity, comprising administering to the subject a therapeutically effective amount of a compound of formula I, or a stereoisomer, tautomer, solvate, pharmaceutically acceptable salt thereof.

In one embodiment, the present disclosure provides a pharmaceutical composition comprising a compound of formula I, or a stereoisomer, tautomer, solvate, pharmaceutically acceptable salt thereof, and a pharmaceutically acceptable carrier.

In one embodiment of the present disclosure regarding the method of treating a patient treating diseases or disorders, the compound of formula I, or a stereoisomer, tautomer, solvate, pharmaceutically acceptable salt thereof, can be injected or orally administered.

Those skilled in the art will recognize that numerous modifications can be made to the specific implementations described above. The implementations should not be limited to the particular limitations described. Other implementations may be possible.

We claim:
1. A compound of formula I:

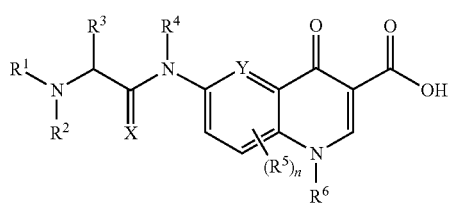

I or a stereoisomer, tautomer, pharmaceutically acceptable salt thereof, wherein:
$R^1$ and $R^2$ independently represents a group selected from hydrogen, optionally substituted ($C_1$-$C_4$) alkyl, optionally substituted ($C_4$-$C_8$) cycloalkyl, optionally substituted ($C_2$-$C_4$) alkylcarbonyl, optionally substituted ($C_4$-$C_8$) cycloalkylcarbonyl, optionally substituted aryl, optionally substituted arylcarbonyl, optionally substituted heterocyclyl, wherein the heterocyclyl ring is 5-7 membered ring containing 1 to 4 heteroatoms selected from O, S, and N, optionally substituted heterocyclylcarbonyl, optionally substituted ($C_1$-$C_4$) alkyl-$SO_2$-, optionally substituted aryl-$SO_2$-;
wherein the said groups are substituted by hydrogen, halogen, hydroxy, amino, nitro, $CF_3$, cyano, ($C_1$-$C_4$) alkyl, ($C_1$-$C_4$) alkoxy, or ($C_1$-$C_4$) alkyl-amino;
$R^3$ represents a group selected from H, optionally substituted ($C_1$-$C_4$) alkyl, optionally substituted ($C_1$-$C_4$) alkenyl, optionally substituted ($C_1$-$C_4$) alkynyl, optionally substituted ($C_4$-$C_8$) cycloalkyl, optionally substituted aryl, optionally substituted heteroaryl, or optionally substituted heterocyclyl, wherein the heteroaryl and heterocyclyl are 5-7 membered rings with 0-3 sites of unsaturation containing 1 to 4 heteroatoms selected from O, S, and N and, wherein the said groups are substituted by hydrogen, halogen, hydroxy, amino, nitro, $CF_3$, cyano, $C_1$-$C_4$ alkyl, $C_1$-$C_4$ alkoxy, or $C_1$-$C_4$ alkyl-amino;
$R^4$ and $R^6$ independently represents a group selected from hydrogen, optionally substituted ($C_1$-$C_4$) alkyl, optionally substituted ($C_4$-$C_8$) cycloalkyl, optionally substituted aryl or optionally substituted heteroaryl, wherein the heteroaryl is 5-7 membered ring containing 1 to 4 heteroatoms selected from O, S, and N and, wherein the said groups are substituted by hydrogen, halogen, hydroxy, amino, nitro, $CF_3$, cyano, $C_1$-$C_4$ alkyl, $C_1$-$C_4$ alkoxy, or $C_1$-$C_4$ alkyl-amino;
$(R^5)n$ represents a group selected from —H, —F, —Cl, —Br, —I, —$CFH_2$, —$CF_2H$, —$CF_3$, —CN, —OH, —$NO_2$, —$NH_2$, —$SO_2CH_3$, $SO_2NH_2$, —$SO_2NHCH_3$, —$CO_2$-($C_1$-$C_4$) alkyl, NH($C_1$-$C_4$) (alkyl) or N($C_1$-$C_4$) (alkyl)$_2$, ($C_1$-$C_4$) alkyl, ($C_1$-$C_4$) alkenyl, ($C_1$-$C_4$) alkoxy, ($C_4$-$C_8$) cycloalkyl; wherein n is 1 or 2;
X is O or H, wherein —C=X— is —$CH_2$— when X is H; and
Y is C—$R^5$ or N, wherein $R^5$ is as defined above.

2. The compound of claim 1, wherein $R^4$ and $R^6$ are H, and $R^3$ is $C_1$-$C_4$ alkyl.

3. The compound of claim 1, wherein at least one of $R^1$ and $R^2$ is H.

4. The compound of claim 1, wherein $R^4$ and $R^6$ are H, $R^3$ is $C_1$-$C_4$ alkyl, and at least one of $R^1$ and $R^2$ is H.

5. The compound of claim 1, wherein one of $R^1$ and $R^2$ is an optionally substituted biphenylcarbonyl or optionally substituted phenylcarbonyl, wherein the biphenylcarbonyl or phenylcarbonyl are substituted by hydrogen, halo, hydroxy, amino, nitro, $CF_3$, cyano, $C_1$-$C_4$ alkyl, $C_1$-$C_4$ alkoxy or $C_1$-$C_4$ alkyl-amino.

6. The compound of claim 1, wherein X is O.

7. The compound of claim 1, wherein Y is —C—H, C—F, C—Cl, C—Br, C—I, Or N.

8. The compound of claim 1, wherein the compound is selected from the group consisting of:

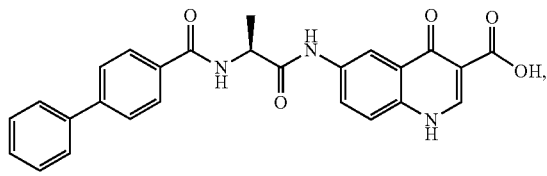

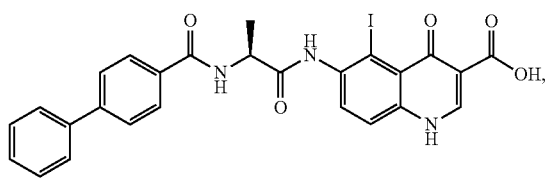

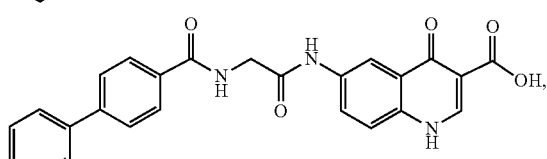

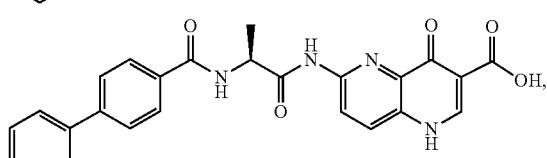

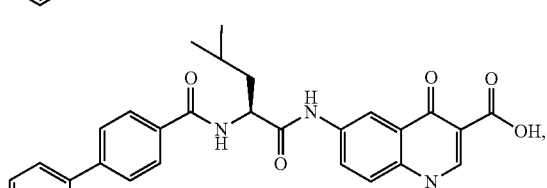

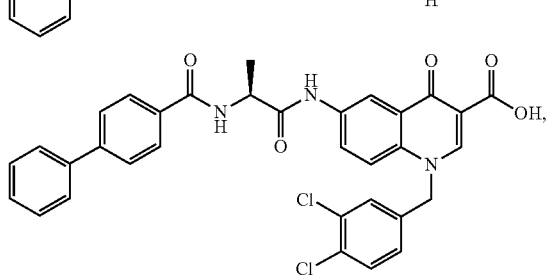

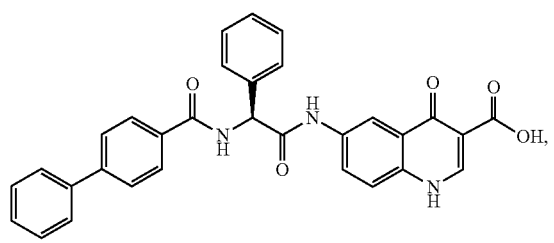
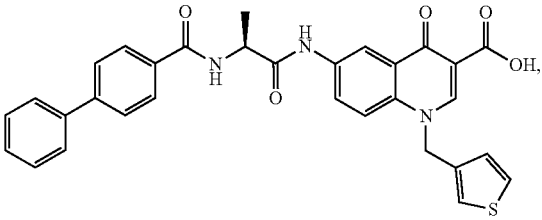
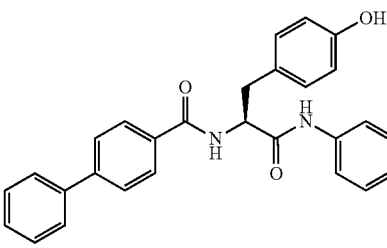
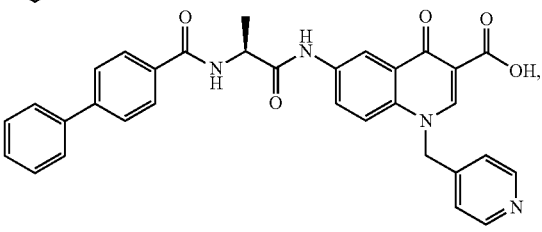
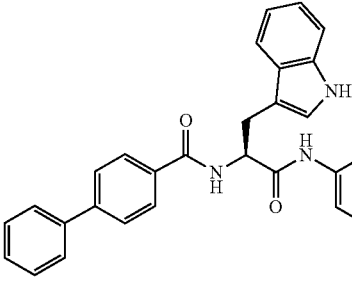
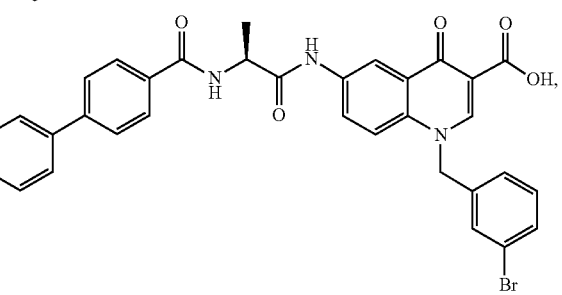
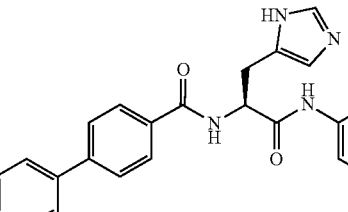
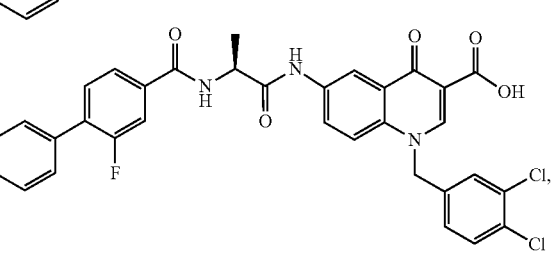

-continued
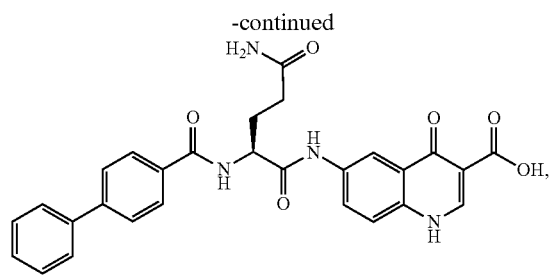
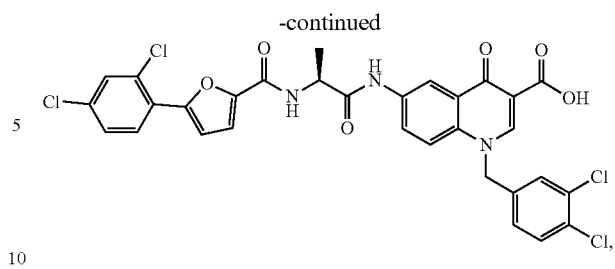
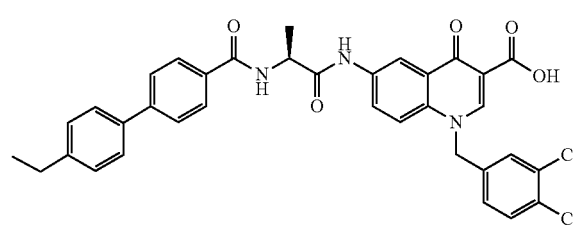
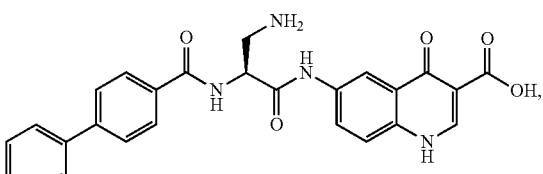
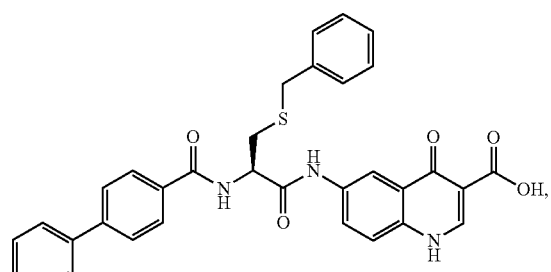
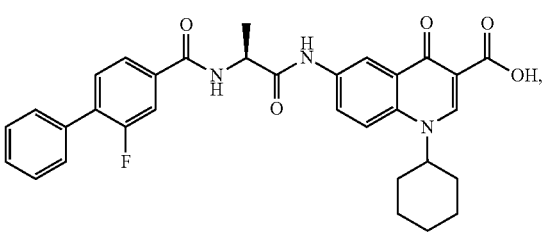
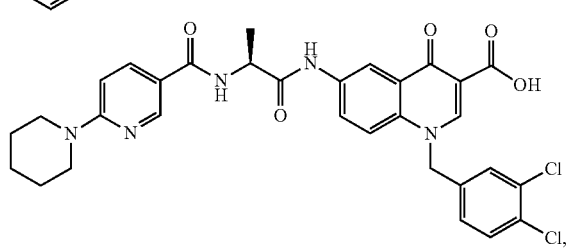
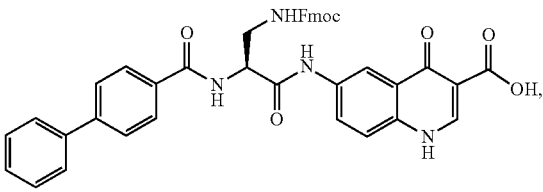
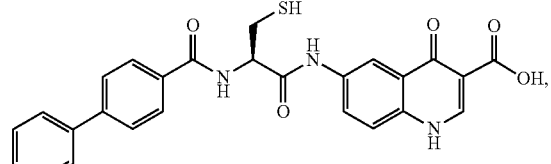
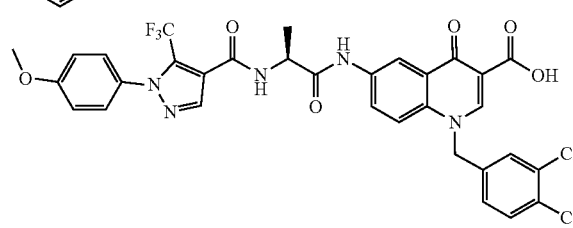
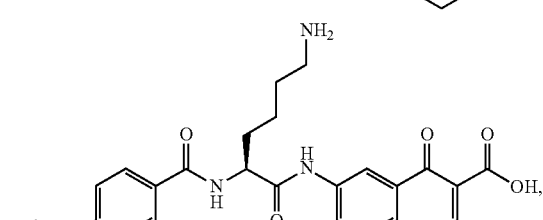
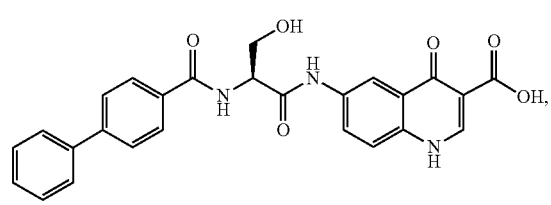
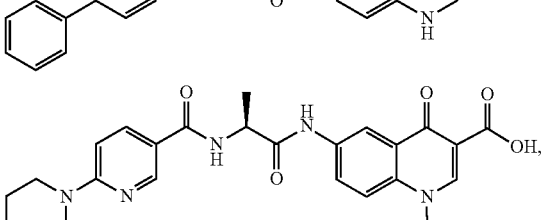
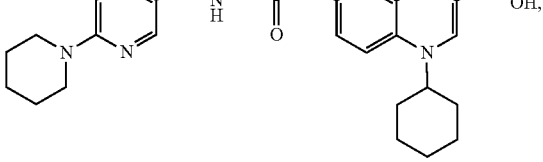

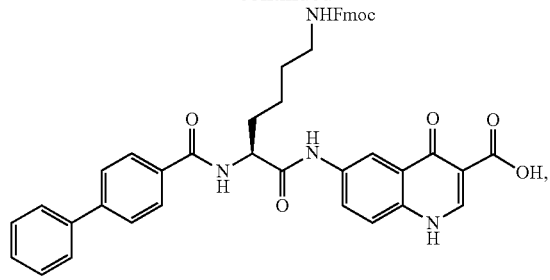
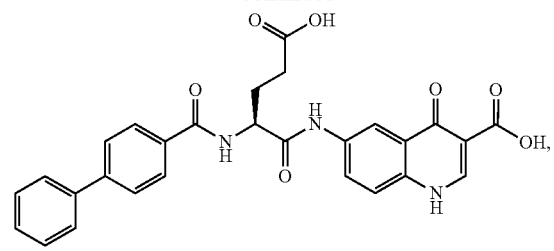
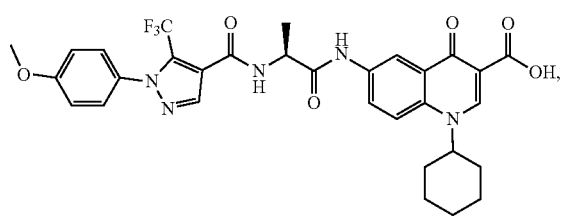
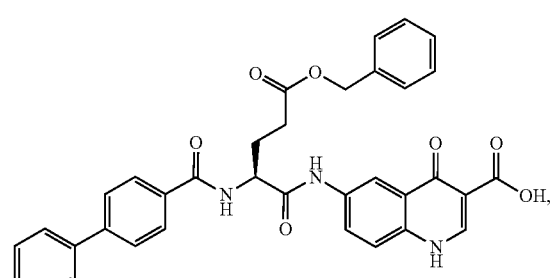
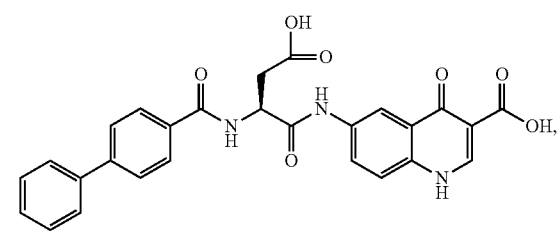
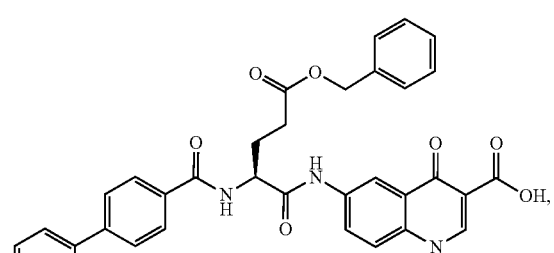
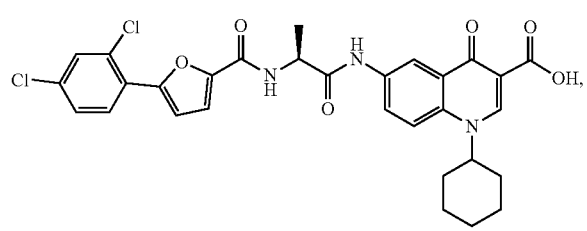
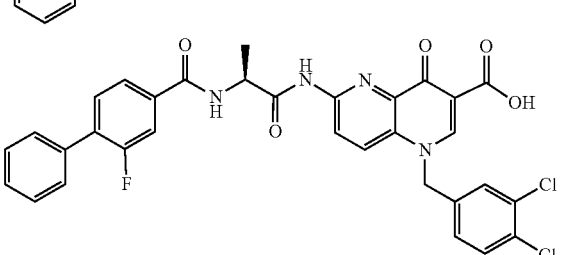
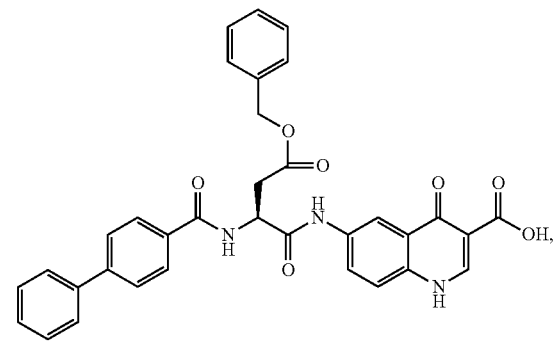
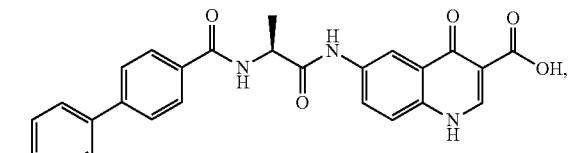
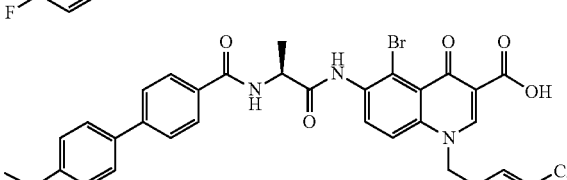
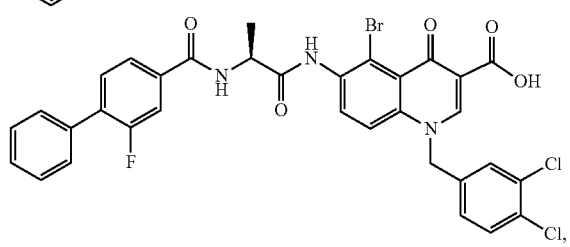
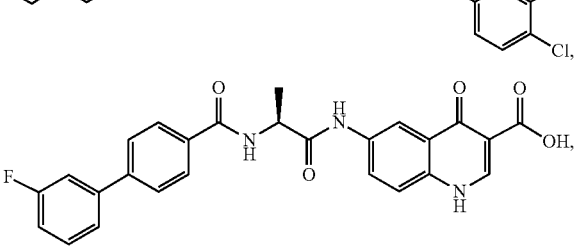

-continued
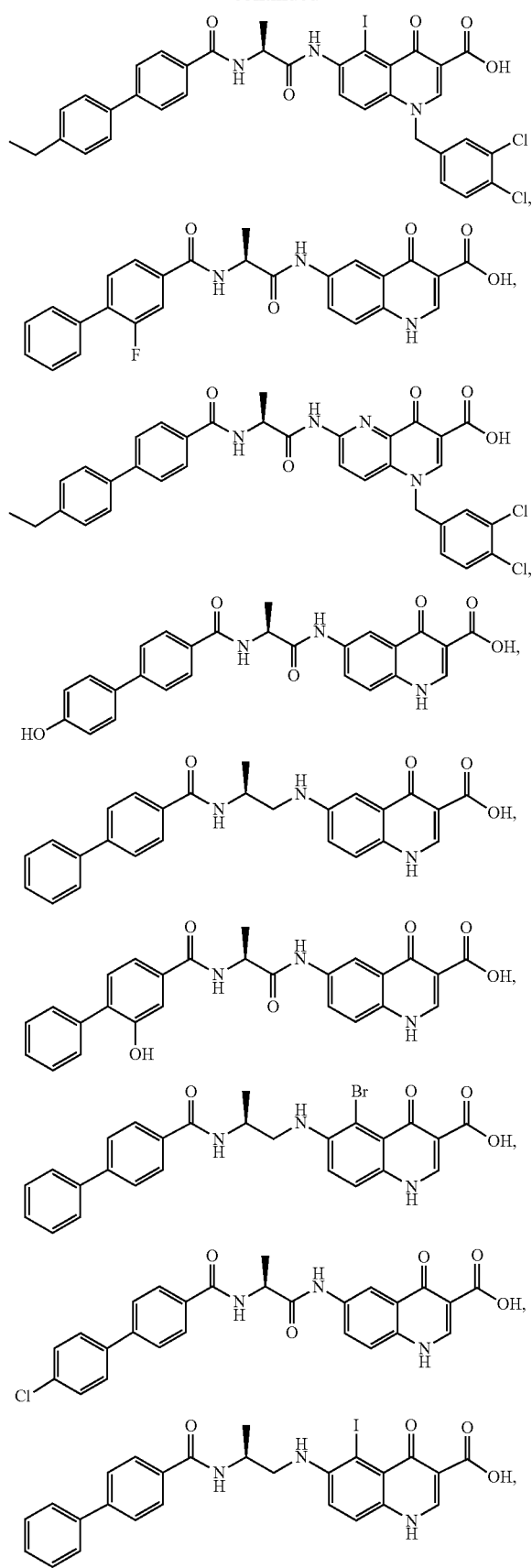
-continued
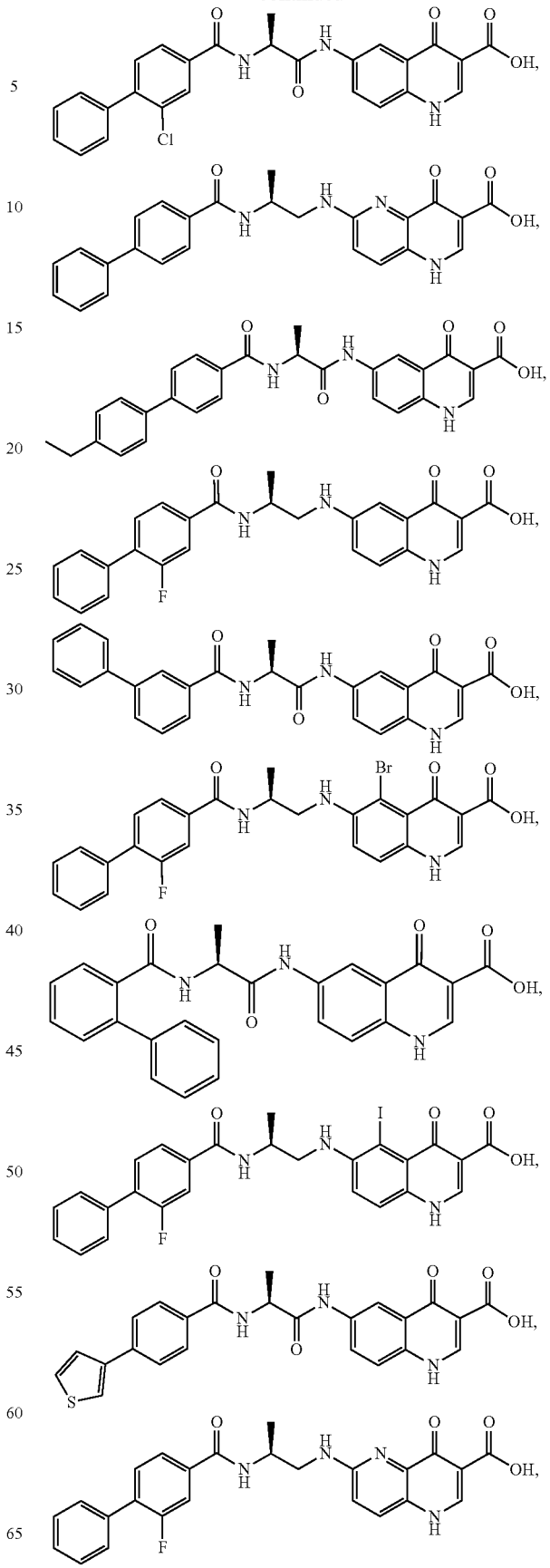

77
-continued
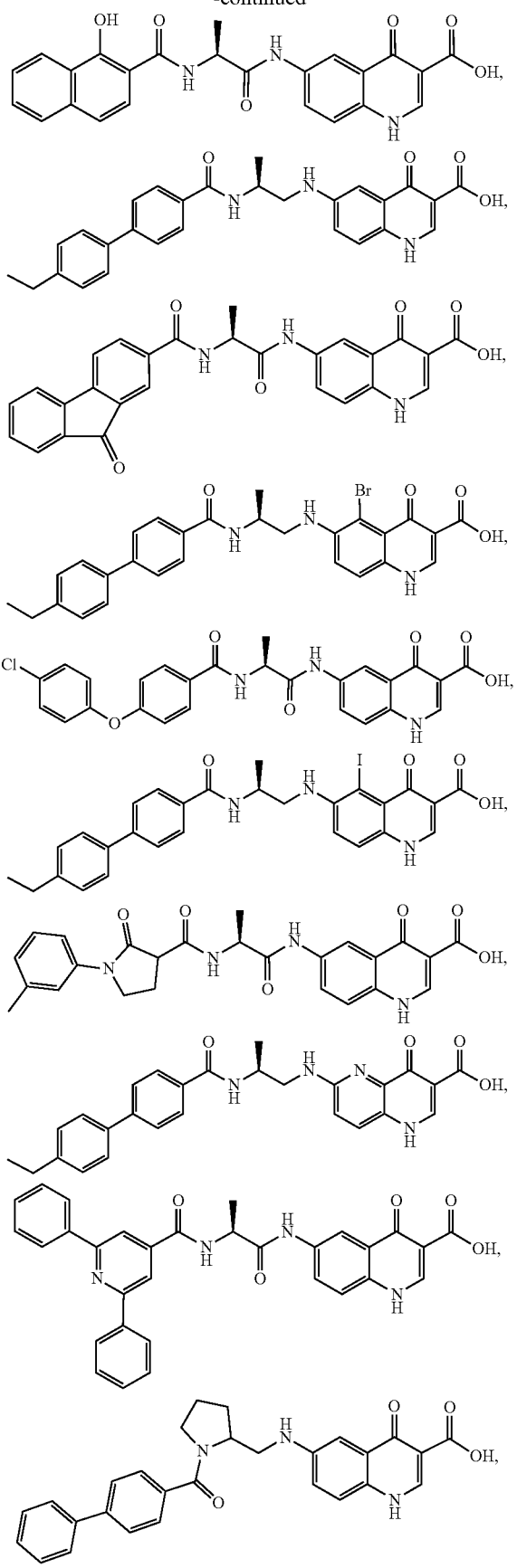
78
-continued
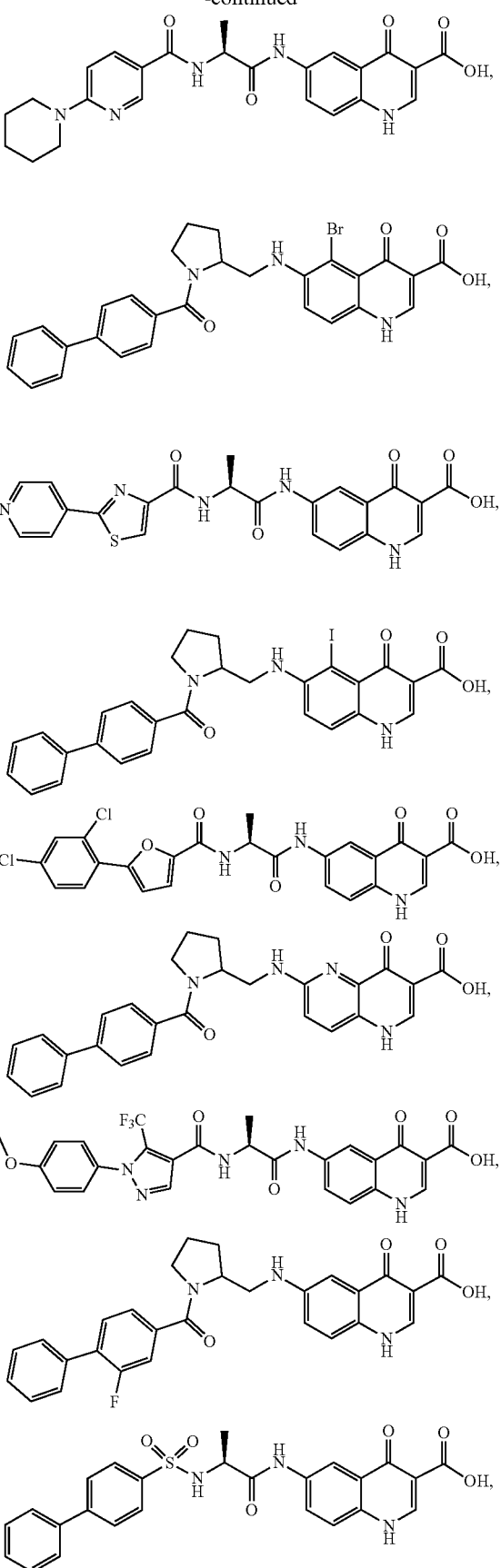

-continued

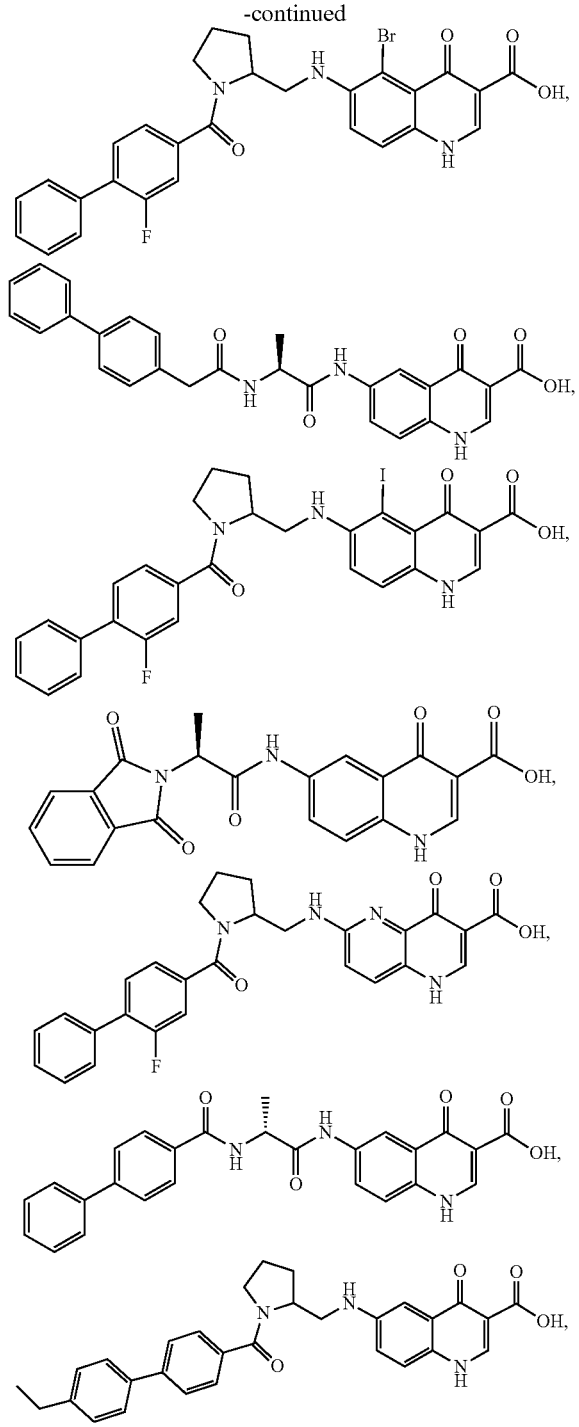

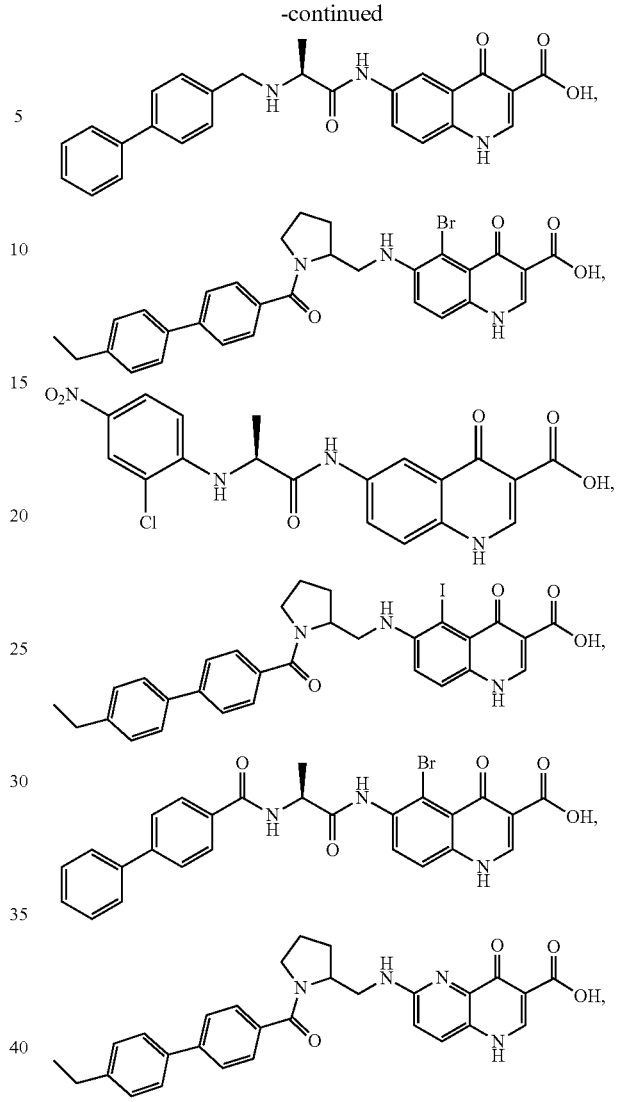

and any stereoisomer, tautomer, or pharmaceutically acceptable salt thereof.

9. A method of treating a patient in need of cancer immunotherapy for colon cancer which method comprises administering to the patient a therapeutically effective amount of the compound of claim 1, or a stereoisomer, tautomer, pharmaceutically acceptable salt thereof.

10. The method of claim 9, wherein the therapeutically effective amount is administered orally or intravenously.

* * * * *